Figure 4:
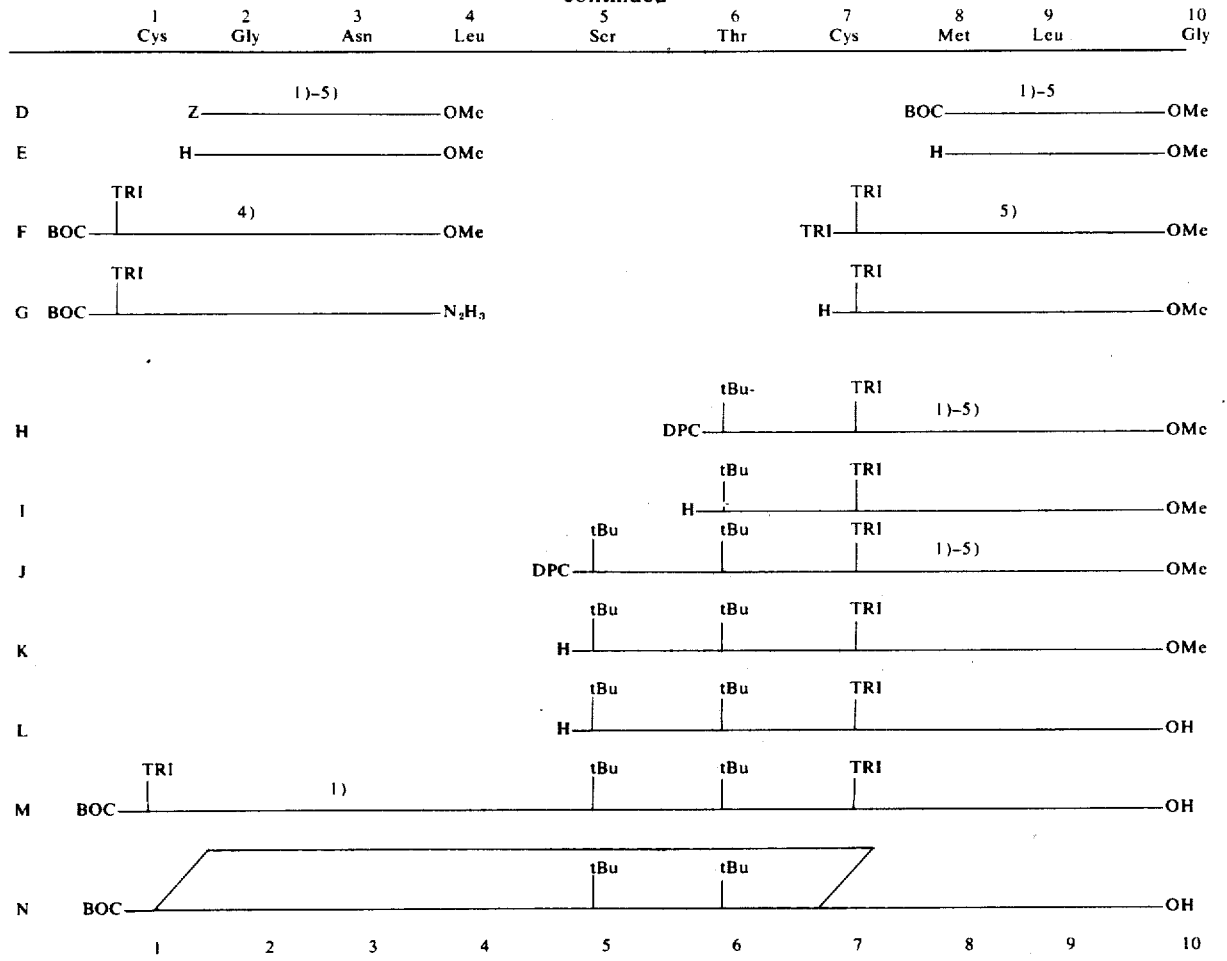

United States Patent [19]

Rittel et al.

[11] 3,934,008

[45] Jan. 20, 1976

[54] N-ACYL AND DESAMINO HUMAN CALCITONIN AND ANALOGS THEREOF

[75] Inventors: Werner Rittel, Basel; Max Brugger, Birsfelden; Bruno Kamber, Basel; Bernhard Riniker, Frenkendorf; Peter Sieber, Reinach, all of Switzerland; Hendrik Marie Greven, Heesch, Netherlands

[73] Assignee: Ciba-Geigy Corporation, Ardsley, N.Y.

[22] Filed: July 14, 1972

[21] Appl. No.: 271,873

Related U.S. Application Data

[63] Continuation of Ser. No. 850,254, Aug. 14, 1969, abandoned.

[30] Foreign Application Priority Data

| Aug. 23, 1968 | Switzerland | 12691/68 |
| Aug. 27, 1968 | Switzerland | 12811/68 |
| Aug. 30, 1968 | Switzerland | 13067/68 |
| Oct. 10, 1968 | Switzerland | 15147/68 |
| Nov. 19, 1968 | Switzerland | 17235/68 |

[52] U.S. Cl.............................. 424/177; 260/112.5 T
[51] Int. Cl.².................A61K 37/00; C07C 103/52; C07G 7/00
[58] Field of Search................................ 260/112.5

[56] References Cited
UNITED STATES PATENTS

| 2,978,444 | 4/1961 | Schwyzer et al. | 424/177 |
| 3,091,569 | 5/1963 | Sheffner | 424/177 |
| 3,509,120 | 4/1970 | Bodanszky | 260/112.7 |
| 3,528,960 | 9/1970 | Haas | 260/112.7 |
| 3,647,775 | 3/1972 | Marquarding et al. | 260/112.5 |
| 3,652,531 | 3/1972 | Miyoshi et al. | 424/177 |
| 3,684,791 | 8/1972 | Geiger et al. | 260/112.7 |
| 3,749,703 | 7/1973 | Guttmann et al. | 260/112.5 |
| 3,823,125 | 9/1974 | Grant et al. | 260/112.7 |

OTHER PUBLICATIONS

Barrett et al., J. Clin. Endocrin. Metab., 28, 734–739, (1968).
Aliapoulios et al., J. Clin. Endocrin. Metab., 26, 897–901, (1966).
Milhaud et al., C. R. Acad. Sci. Paris, Ser. D., 266, 608–610, (1968).
Neher et al., Helv. Chim. Acta, 51, 1900–1905, (1968).
Sieber et al., Helv. Chim. Acta, 51, 2057–2061, (1968).

*Primary Examiner*—Lewis Gotts
*Assistant Examiner*—Reginald J. Suyat
*Attorney, Agent, or Firm*—Joseph G. Kolodny; John J. Maitner; Theodore O. Groeger

[57] ABSTRACT

The new hypocalcaemically active peptides of formula I

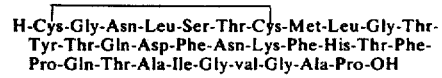

and corresponding compounds in which one or more of the asparagine and glutamic acid radicals are replaced by the aspartic acid or glutamic acid radical and/or the aspartic acid radical is replaced by the asparagine radical, their dimers, especially those in which 2 identical peptide sequences (1–32 and 1'–32') are joined in an anti-parallel arrangement via the cysteine radicals 1,7' and 7,1' by means of a disulfide bond, and derivatives are useful as hypocalcaemic agents and are prepared by splitting off groups protecting at least one amino or one carboxyl group or oxidizing the corresponding sulfides to the disulfides or condensing together adequate peptides.

19 Claims, No Drawings

N-ACYL AND DESAMINO HUMAN CALCITONIN AND ANALOGS THEREOF

CROSS-REFERENCE TO RELATED APPLICATION

This is a continuation of application Ser. No. 850,254 filed Aug. 14, 1969 (now abandoned).

The subject of the invention are the new hypocalcaemically active peptides of formula I

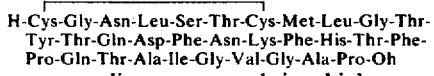

```
H-Cys-Gly-Asn-Leu-Ser-Thr-Cys-Met-Leu-Gly-Thr-
  Tyr-Thr-Gln-Asp-Phe-Asn-Lys-Phe-His-Thr-Phe-
  Pro-Gln-Thr-Ala-Ile-Gly-Val-Gly-Ala-Pro-Oh        I
``` and corresponding compounds in which one or more of the asparagine and glutamic acid radicals are replaced by the aspartic acid or glutamic acid radical and/or the aspartic acid radical is replaced by the asparagine radical, their dimers, especially those in which 2 identical peptide sequences (1-32 and 1'-32') are joined in an anti-parallel arrangement via the cysteine radicals 1,7' and 7,1' by means of a disulfide bond, and derivatives, and processes for the manufacture of these compounds.

Derivatives are for example amides, especially N-unsubstituted C-terminal amides.

Further derivatives of the compounds mentioned are those in which at least the α-amino group is acylated, as well as corresponding desamino$^1$-peptides.

Acyl groups for the acylation of the amino groups, especially for the acylation of $N^\alpha$ -amino groups are the radicals of carboxylic acids such as aliphatic, aromatic, araliphatic, heterocyclic and heterocyclyl-aliphatic carboxylic acids, especially of lower monobasic or dibasic alkane-acids or alkene-acids such as formic acid, acetic acid, propionic acid, butyric acids, acrylic acid or succinic acid, of alicyclic carboxylic acids such as cycloalkylcarboxylic acids, of monobasic or dibasic monocyclic aromatic carboxylic acids such as unsubstituted and substituted benzoic acid of phthalic acid of unsubstituted and aryl-substituted aryl-lower alkylcarboxylic or aryl-lower alkenylcarboxylic acids such as phenylacetic acid, of unsubstituted or substituted monobasic or dibasic 5-membered to 6-membered heterocyclic acids containing nitrogen, sulfur and/or oxygen as hetero-atoms such as pyridinecarboxylic acids or thiophenecarboxylic acids, or of heterocyclyl-lower alkane-acids such as pyridylacetic acid or imidazolylacetic acid, wherein the substitutents of the rings are for example halogen atoms, nitro groups, lower alkyl groups or lower alkoxy groups or lower carbalkoxy groups. Further, acyl radicals of aminoacids, especially α-amino-acids, such as for example the pyroglutamyl radical, should above all be mentioned as acyl radicals, as should acyl radicals which are derived from carbonic acid or thiocarbonic acid or their esters or amides, for example lower alkyloxycarbonyl groups such as ethoxycarbonyl and tert.-butyloxycarbonyl, and also unsubstituted benzoyloxycarbonyl and benzoyloxycarbonyl substituted as mentioned above, carbamoyl and thiocarbamoyl as well as N-substituted carbamoyl and thiocarbamoyl, for example N-lower alkylcarbamoyl, N-phenylcarbamoyl and N-phenylthiocarbamoyl.

As acid addition salts, salts of therapeutically usable acids such as hydrochloric acid, acetic acid, sulfuric acid, phosphoric acid and sulfonic acids such as lower alkanesulfonic acids, benzenesulfonic acid or toluenesulfonic acid should especially be mentioned.

By complexes there are to be understood the compounds of as yet unclarified structure, which are produced on adding certain inorganic or organic substances to long-chain peptides and which impart a prolonged action to these. Such substances are for example described for insulin and for ACTH and other adrenocorticotropically active peptides. Compounds to be mentioned are for example inorganic compounds which are derived from metals such as calcium, magnesium, aluminum, cobalt and especially zinc, above all sparingly soluble salts such as phosphates, pyrophosphates and polyphosphates as well as hydroxides of these metals, optionally in combination with acid organic substances, for example polysaccharides containing acid groups, such as carboxymethylcellulose, or tannic acid, polyglutamic acid or partially hydrolyzed gelatin, and also alkali metal polyphosphates such as for example "Calgon N", "Calgon 322", "Calgon 188" or "Polyron B 12". Organic substances which cause a prolongation of the action are for example non-antigenic gelatines, for example polyhydroxy gelatines, polyvinylpyrrolidone and carboxymethylcellulose, and also sulfonic acid or phosphoric acid esters of alginic acid, dextran, polyphenols and polyalcohols, above all polyphoretine phosphate and phytic acid, as well as polymers and copolymers of aminoacids, for example protamine or polyglutamic acid.

The new compounds have a hypocalcaemic action. Thus the C-terminal amide of the compound of the formula I shows in the test on rats described by Kumar et al, J. Endocrynology 33, [1965], 470, an activity of about 100–200 MRC units per mg (peptide). The new compounds lower the plasma calcium and phosphate content of the blood of mammals, as has been demonstrated by experiments with rats weighing 50–150 g.

In patients with increased bone metabolism they lower the calcium level of the blood on intravenous, intramuscular or subcutaneous administration of 0.01 to 5 mg, for example in 0.1-molar acetate buffer of pH 4.6. They can therefore be used for the treatment of hypocalcaemia and of bone diseases such as Paget's disease or of osteoporosis.

The compound of the formula I having a free C-terminal carboxyl group is itself but little active, but it can be used as starting or intermediate product in the manufacture of active compounds. For Example, it can be converted into the corresponding Asp$^{15}$, Pro$^{32}$-diamide which is as active as calcitonine M, for example by converting the product of the formula I into the $N^\alpha$ ,$N^\epsilon$ -di-BOC-protected product by means of tertiary butyloxycarbonylazide, and then forming the diamide with ammonia in the presence of dicyclohexylcarbodimide and hydroxysuccinimide, and finally splitting off the BOC groups with acid, for example hydrochloric acid or trifluoracetic acid.

The process according to the invention for the manufacture of the new monomeric or dimeric peptides, their derivatives, their acid addition salts and complexes is characterized in that 1. the protective group or groups are split off from compounds of formula I or the quoted analogues or derivatives or dimers of these compounds, in which compounds at least one amino group or one carboxyl group is protected by a removable protective group or 2. compounds of formula II H-Cys-Gly-Asn-Leu-Ser-Thr-Cys-Met-Leu-Gly-Thr-
Tyr-Thr-Gln-Asp-Phe-Asn-Lys-Phe-His-Thr-Phe-
Pro-Gln-Thr-Ala-Ile-Gly-Val-Gly-Ala-Pro-OH   II or the quoted analogues or derivatives wherein the mercapto groups are free or protected by the trityl group, are oxidised to disulphides or 3. compounds of formula III or IV

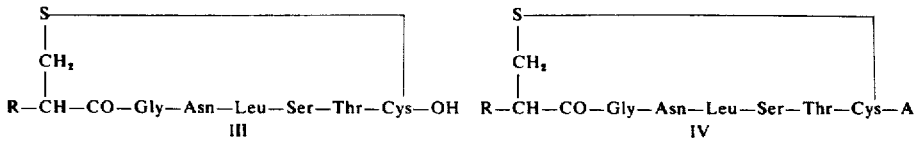

wherein A represents 1 to 21 of the aminoacid residues which follow the cysteine[7] having an optionally protected side-chain amino group, and R represents hydrogen or an acylated amino group, are condensed according to methods known in peptide synthesis, with the remaining C-terminal sequence of the peptide having an optionally protected side-chain amino group up to the C-terminal aminoacid (L-proline), with the proviso that a method which starts from an activated carboxylic acid group, such as the azide method, the anhydride method or the method of activated esters is employed if the C-terminal sequence has a free carboxyl group and that, if desired, the resulting monomeric compounds are converted to their dimers or the free monomeric or dimeric peptides are converted to their derivatives and/or acid addition salts or complexes.

In the manufacture of the starting substances for the 1st. variant of the process according to the invention and also of all intermediates required in the 3 process variants, possible protective groups are especially those known from the synthesis of long-chain peptides as well as some new protective groups which can be easily split off, for example by hydrolysis, reduction, aminolysis or hydrazinolysis.

Thus for example protective groups used for amino groups are acyl or aralkyl groups such as formyl, trifluoroacetyl, phthaloyl, benzenesulphonyl, p-toluenesulphonyl, o-nitrophenylsulphenyl, 2,4-dinitrophenylsulphenyl groups (these sulphenyl groups can also be split off by the action of nucleophilic reagents, for example sulphites or thiosulphates, compare British Pat. No. 1,104,271), benzyl or diphenyl or triphenylmethyl groups which are optionally substituted, such as for example by lower alkoxy groups, especially o- or p-methoxy groups or of groups which are derived from carbonic acid, such as arylmethyloxycarbonyl groups which are optionally substituted in the aromatic rings, for example by halogen atoms such as chlorine or bromine, nitro groups, lower alkyl or lower alkoxy groups or chromophoric groups, for example azo groups, in which the methylene group may be substituted by a further aryl residue and/or by one or optionally two lower alkyl residues, such as benzyl-, benzhydryl- or 2-phenyl-isopropyloxycarbonyl groups, for example carbobenzoxy, p-bromocarbobenzoxy or p-chlorocarbobenzoxy, p-nitrocarbobenzoxy or p-methoxycarbobenzoxy, p-phenylazo-benzyloxycarbonyl and p-(p'-methoxy-phenylazo)-benzyloxycarbonyl, 2-tolylisopropyloxycarbonyl and especially 2-(p-biphenylyl)-isopropyloxycarbonyl [compare Application G. No. 1073/67 (Case 6106)] as well as aliphatic oxycarbonyl groups such as adamantyloxycarbonyl, cyclopentyloxycarbonyl, trichlorethyloxycarbonyl, tert. amyloxycarbonyl or above all tert.-butyloxycarbonyl.

The amino groups can also be protected by the formation of enamines obtained by reaction of the amino group with 1,3-diketones, for example benzoylacetone, acetylacetone or dimedone.

Carboxyl groups are for example protected by amide or hydrazide formation or by esterification. The amide and hydrazide groups can optionally be substituted, the amide group for example by the 3,4-dimethoxybenzyl- or bis-(p-methoxyphenyl)-methyl group and the hydrazide group for example by the carbobenzoxy group, the trichlorethyloxycarbonyl group, the trifluoracetyl group, the trityl group, the tert.-butyloxycarbonyl group or the 2-(p-biphenylyl)-isopropyloxycarbonyl group. Suitable compounds for esterification are for example lower optionally substituted alkanols such as methanol, ethanol, cyanomethyl alcohol, benzoylmethyl alcohol or especially tert.-butanol, and also aralkanols such as aryl-lower alkanols, for example benzyl or benzhydryl alcohols which are optionally substituted by lower alkyl or lower alkoxy groups or halogen atoms, such as p-nitrobenzyl alcohol, p-methoxybenzyl alcohol or 2,4,6-trimethylbenzyl alcohol, phenols or thiophenols which are optionally substituted by electron-attracting substituents such as thiophenol, thiocresol, p-nitrothiophenol, 2,4,5- and 2,4,6-trichlorophenol, pentachlorophenol, p-nitrophenol, 2,4-dinitrophenol, p-cyanophenol or p-methanesulphonylphenol, and also, for example, N-hydroxysuccinimide, N-hydroxyphthalimide, N-hydroxypiperidine and 8-hydroxyquinoline.

The hydroxyl groups of the serine, threonine and tyrosine residues can for example be protected by esterification or etherification. Suitable acyl residues for the esterification are for example lower alkanoyl residues such as acetyl, aroyl residues such as benzoyl or above all residues derived from carbonic acid such as benzyloxycarbonyl or ethyloxycarbonyl. Suitable groups for the etherification are for example benzyl, tetrahydropyranyl or tert. butyl radicals. Further groups which are suitable for the protection of the hydroxyl groups are the 2,2,2-trifluoro-1-tert.-butyloxycarbonylaminoethyl or -1-benzyloxycarbonylaminoethyl groups (Weygand) described in Ber. 100 (1967), 3838–3849. It is however not necessary to protect the hydroxyl groups.

The mercapto groups of the cystein radicals are for example protected by acylation or alkylation. The acetyl or benzoyl radical, a lower alkylcarbamoyl radical, for example the ethylcarbamoyl radical or the optionally substituted carbobenzoxy radical is for example suitable for the acylation. The tert.-butyl or benzylthiomethyl radical or optionally substituted arylmethyl groups such as benzyl, p-nitrobenzyl, diphenylmethyl, dimethoxybenzhydryl or trityl, and also phenylcyclohexyl, thienyl(2)-cyclohexyl and others, compare Ber. 101, (1968), 681, are for example suitable for the alkylation. It is not essential to protect the imino group of the histidine but it can be advantageous to protect it, for example by benzyl, trityl, carbobenzoxy, adamantyloxycarbonyl or the abovementioned Weygand groups.

Preferably, in the 1st. variant of the process according to the invention, the carboxyl group of the side-chain and optionally the terminal carboxyl group are protected by the tert.-butyl ester group, the amino group of the side-chain is protected by the tert.-butyloxycarbonyl group, the hydroxyl groups of the serine, threonine and tyrosine radical, to the extent that these are protected at all, are protected by the tert.-butyl ether group and, if desired, the imino group of the histidine is protected by the 2,2,2-trifluoro-1-tert.-butyloxycarbonylaminoethyl group. All these protective groups may, if desired, be split off in one stage by acid hydrolysis, for example by means of trifluoracetic acid or hydrochloric acid. In the synthesis of the protected dotriacontapeptides used as the starting material in the 1st. process variant, using protective groups which can be split off with trifluoracetic acid or hydrochloric acid, the mercapto groups are preferably protected by benzyl or trityl. The S-trityl groups can be split off selectively from the protected peptide in organic solution (whilst retaining the groups which can be split off with trifluoracetic acid) by means of mercuric acetate and hydrogen sulphide. The S-benzyl groups can be selectively split off from the protected peptide by means of sodium in liquid ammonia. In both cases the protected peptide with free mercapto groups is obtained. This can be oxidized to the protected disulphide, for example with iodine in glacial acetic acid, with diiodoethane or dithiocyanogen in organic solvents or with atmospheric oxygen in liquid ammonia. It is particularly advantageous to protect the mercapto groups by trityl groups and to remove these from the protected peptide with simultaneous formation of the disulphide bridge by means of iodine in methanol, compare Swiss Application No. 6999/68 (Case 6461). The formation of the disulphide ring can be carried out at the stage of a part-sequence containing the two cysteine residues, for example at the stage of the decapeptide 1–10, or at the stage of the dotriacontapeptide.

In the 2nd. process variant of the process according to the invention the open-chain peptide used as the starting material can preferably again be manufactured with the protective groups mentioned for variant 1). The S-trityl groups can be removed with trifluoracetic acid and the free open-chain peptide can be oxidised in a known manner by means of potassium ferricyanide in aqueous solution or by means of iodine or with air in liquid ammonia. It is however also possible to remove the trityl groups in accordance with the abovementioned process by means of iodine and methanol with simultaneous disulphide formation.

In the manufacture of the N-acyl derivatives the acyl group can be used as an amino-protective group.

The resulting monomeric peptides can, in a manner which is in itself known, subsequently be converted to their dimers or vice versa and/or the monomeric or dimeric peptides can be converted to their derivatives, acid addition salts and/or complexes. The subsequent conversions can be carried out in an appropriate sequence, either individually or in combination.

The conversion of resulting monomeric compounds to dimeric compounds is for example effected by treatment with mercapto compounds in a neutral or weakly acid medium, for example by treatment with cysteine hydrochloride. The dimeric compounds can be converted to the monomeric compounds under basic conditions, for example with dilute ammonia.

In order to manufacture acyl deivatives the free peptide can be N-acylated in the usual manner, for example by reaction with a mixed anhydride or acid azide containing the acyl residue in question or above all with an activated ester such as a phenyl or substituted phenyl ester. The acylation can, if desired, be carried out selectively so that only the α-amino group is acylated.

The formation of acid addition salts is performed in a known manner.

The formation of complexes also takes place according to known methods or methods equivalent to these.

Complexes with inorganic substances such as sparingly soluble metal compounds, for example aluminum or zinc compounds, are preferably manufactured in an analogous manner to that known for insulin or ACTH, for example by reaction with a soluble salt of the metal in question, for example zinc chloride or zinc sulphate, and precipitation with an alkali metal phosphate and/or alkali metal hydroxide. Complexes with organic compounds such as polyhydroxy gelatines, carboxymethylcellulose, polyvinylpyrrolidone, polyphloretine phosphate, polyglutamic acid and the like are obtained by mixing these substances with the peptide in aqueous solution. Insoluble compounds with alkali metal polyphosphates can also be manufactured in the same manner.

The invention also relates to those embodiments of the process which start from an intermediate obtainable at any process stage and carry out the missing stages or in which the process is stopped at any stage and/or a starting substance is formed in situ and/or is used in the form of a salt.

The peptides used as starting substances are obtained by linking the aminoacids, whilst using easily removable protective groups if necessary or desired, in the sequence mentioned, either one at a time or after prior formation of smaller peptide units, with the disulphide bridge optionally being formed at a suitable stage of the synthesis. It is appropriate to work in accordance with the linking methods suitable for the manufacture of long-chain peptides, taking the disulphide bridge into account, such as are known from the literature.

The linkage of the aminoacid and/or peptide units is therefore for example performed in such a manner that an aminoacid or a peptide having a protected α-amino group and an activated terminal carboxyl group is reacted with an aminoacid or a peptide having a free α-amino group and free or protected, for example esterified or amidised, terminal carboxyl group, or that an aminoacid or a peptide having an activated α-amino group and a protected terminal carboxyl group is reacted with an aminoacid or a peptide having a free terminal carboxyl group and a protected α-amino group. The carboxyl group can for example be activated by conversion to an acid azide, acid anhydride, acid imidazolide or an activated ester, such as cyanomethyl ester, thiophenyl ester, p-nitrothiophenyl ester, thiocresyl ester, p-methanesulphonylphenyl ester, p-nitrophenyl ester, 2,4-dinitrophenyl ester, 2,4,5- or 2,4,6-trichlorophenyl ester, pentachlorophenyl ester, N-hydroxysuccinimide ester, N-hydroxyphthalimide ester, 8-hydroxyquinoline ester, or N-hydroxypiperidine ester or by reaction by means of a carbodiimide (optionally with the addition of N-hydroxysuccinimide) or N,N'-carbonyldiimidazole or isoxazolium salt, for example Woodward reagent, and the amino group can for example be activated by reaction with a phosphite. As the most usual methods there should be mentioned the carbodiimide method, the method according to Weygand-Wünsch (carbodiimide in the presence of N-hydroxysuccinimide), the azide method, the method of activated esters and the anhydride method, and also the Merrifield method and the method of N-carboxyanhydrides or N-thiocarboxyanhydrides.

Alongside the manufacture of the end products, the manufacture of the starting substances, above all of the peptide fragment containing the disulphide bridge and its linkage with the remaining part of the peptide also represents a special subject of the invention. It has been found that it is advantageous to start from a sequence which comprises the first 10 N-terminal aminoacids and to condense the entire remaining sequence with this N-terminal section.

It is however also possible to link the N-terminal sequence mentioned with the fragment up to the 28th. aminoacid (glycine) having a free C-terminal carboxyl group and to condense the octacosapeptide with the tetrapeptide of the aminoacids 29–32. This procedure is in particular also suitable for the manufacture of C-terminal esters, for example esters which are derived from long-chain alkanols or for the manufacture of N-substituted C-terminal amides. The condensation is for example carried out according to the Weygand-Wünsch method. If the condensation of sequence 1–10 with the C-terminal sequence 11–32 is carried out, the carbodiimide method or the method according to Weygand-Wünsch are preferably used. The manufacture of the N-terminal decapeptide (1–10) is explained in more detail below.

Figure 5:
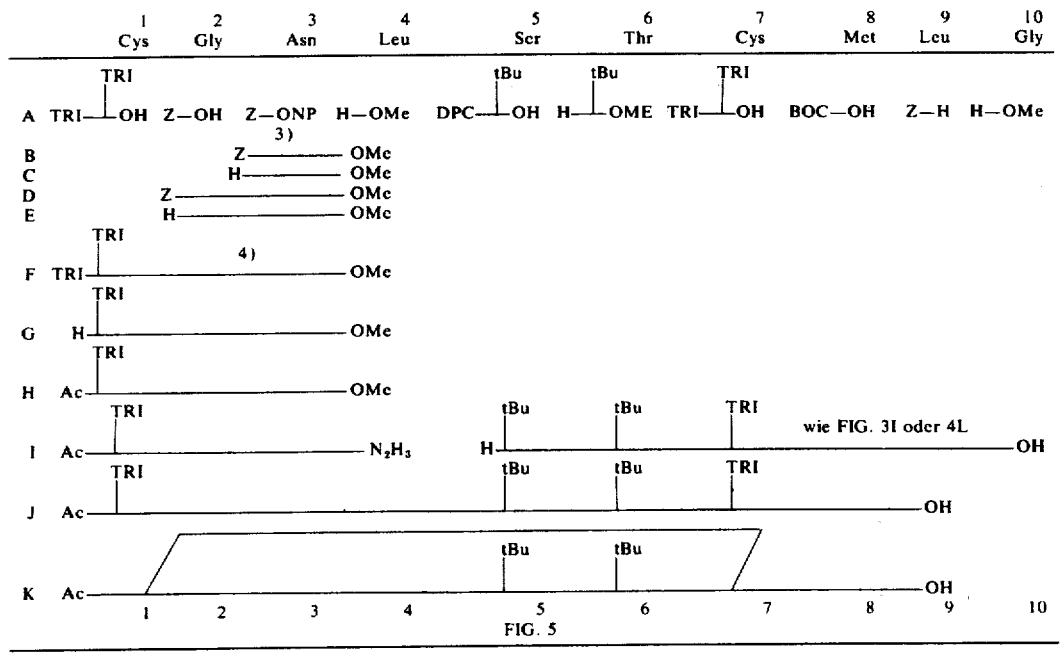

It can for example be synthesised from the sequences 1–4 and 5–10 or 1–5 and 6–10 or 1–6 and 7–10 or 1–7 and 8–10, as can be seen from figures 1–8; it is however also possible to use other fragments to synthesise the sequence 1–10. The protective group used for the α-amino group at the cysteine[1] is preferably the tert.-butyloxycarbonyl group or an equivalent group which can be split off by acid hydrolysis, or, if a $N^\alpha$-acylated dotriacontapeptide is to be manufactured, the corresponding acyl group, for example acetyl group. Alongside this, it is appropriate to use, as mercapto protective groups, such groups as can be selectively split off relative to the $N^\alpha$-amino protective group which can be split off by acid hydrolysis (for example the tert.-butyloxycarbonyl group), for example the benzyl or trityl group. It is not essential to protect the terminal carboxyl group of the decapeptide, for example it is not necessary if condensations are carried out by the azide or anhydride method. This group can however also be protected by esterification, as specified above, for example by esterification with methanol or ethanol (splitting-off the ester group with dilute sodium hydroxide solution) or with benzyl alcohol or analogues (splitting off the ester group with, for example, sodium in liquid ammonia). The amino groups of the intermediates are protected by means of the usual protective groups, for example carbobenzoxy, trityl, tert.-butyloxycarbonyl or 2-(p-biphenylyl)-isopropyloxycarbonyl. The carboxyl groups of the intermediates are, if necessary, esterified in the usual manner. The hydroxyl groups of the serine and threonine residue can be protected by etherification, for example with tert.-butanol or equivalent substances.

In the figures which follow, and in the examples, the symbols have the following significance:

1. the azide method
2. the method of mixed anhydrides
3. the method of activated esters, especially p-nitrophenyl ester (ONP) or hydroxysuccinimide-ester (OSU)
4. the carbodiimide method
5. the method according to Weygand-Wünsch BOC tert.-butyloxycarbonyl
DPC 2-(p-biphenylyl)-isopropylcarbonyl,
Z carbobenzoxy
TRI trityl
Bzl benzyl
OtBu tert.-butyl ester
OBzl benzyl ester
ONB p-nitrobenzyl ester
ONP p-nitrophenyl ester
OMe methyl ester
OEt ethyl ester
OCP 2,4,5-trichlorophenyl ester
tBu tert.-butyl ether
Ac acetyl
Bmp β-mercaptopropionyl
TFA trifluoracetic acid The p-nitrobenzyl ester and benzyl ester groups are, in sequences containing methionine, split off with sodium in liquid ammonia, and in other cases by hydrogenolysis in the presence of palladium on charcoal, the carbobenzoxy group is also split off by hydrogenolysis, the N-trityl group with aqueous acetic acid, the tert.-butyloxycarbonyl group with trifluoracetic acid and the diphenylisopropyloxycarbonyl group with aqueous acetic acid or for example with a mixture of glacial acetic acid, formic acid (82.8 % strength) and water (7:1:2) as described in Swiss Application G. No.1073/67 (Case 6106). The p-nitrobenzyl ester or methyl ester can be converted to the hydrazide by means of hydrazine hydrate. The methyl ester group is hydrolysed with dilute sodium hydroxide solution. The tert.-butyl ester is decomposed with trifluoracetic acid as is the tert.-butyl ether. The S-trityl groups are removed with mercuric acetate and hydrogen sulphide, and the S-benzyl group is removed with sodium in liquid ammonia, in the course of which benzyl or p-nitrobenzyl ester groups which may be present are simultaneously split off. Ring closure to give the disulphide is for example effected by oxidation with 1,2-diiodoethane, and that of the S-trityl-protected compounds with iodine in methanol.

Figures 8, 9, 10:
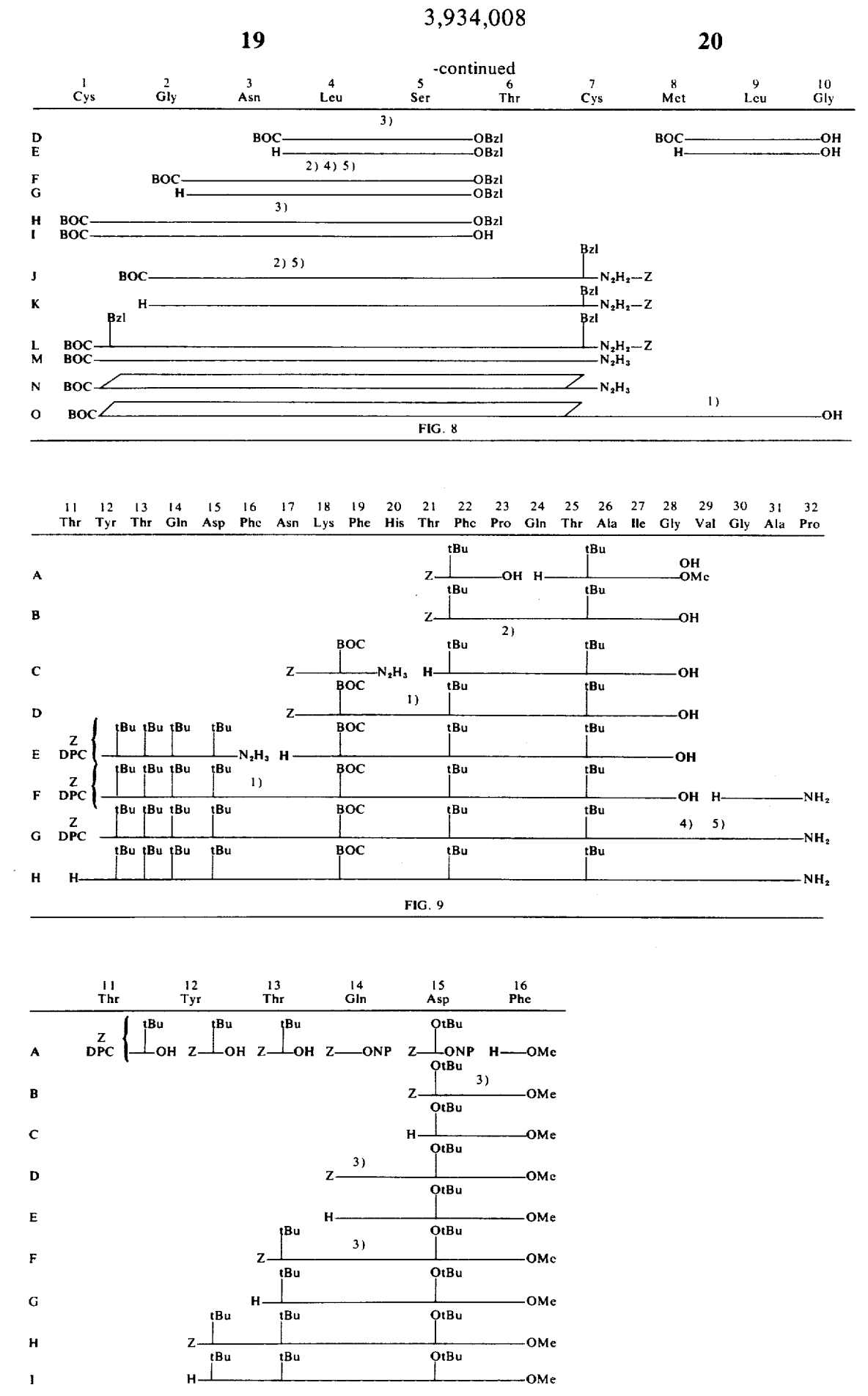

The C-terminal sequence, comprising the 11th. to 32nd. or 11th. to 28th. aminoacid, to be linked to the N-terminal sequence, is for example synthesised from sequences 11–16, 17–20, 21–28 and 29–32, as indicated by FIG. 9.

In this scheme, the hydroxyl groups of the threonine residues and of the tyrosine residue are protected; this is not absolutely essential. It is also possible to combine other partial sequences with one another and to use other protective groups.

FIG. 10 shows the synthesis of the hexapeptide (in the form of the hydrazide) of the aminoacids 11–16. It can be linked to the sequence 17–28 or 17–32 by the azide method.

The sequence 17–28 can be synthesised from the fragments 17–20 and 21–28 by the azide method.

FIG. 11 shows the synthesis of the tetrapeptidehydrazide of the aminoacids 17–20, and FIG. 12 the synthesis of the octapeptide 21–28. After linking the two sequences the α-amino protective group is split off (the carbobenzoxy group by hydrogenolysis in the presence of palladium on charcoal) and the dodecapeptide with protected side-chains thus obtained is condensed with the hexapeptidehydrazide 11–16 (FIG. 10) by the azide method.

The sequence 11–28 thus obtained can be linked to the tetrapeptide-amide of the aminoacids 29–32, the manufacture of which is shown in FIG. 13, for example by the method of Weygand-Wünsch. The protected docosapeptide-amide 11–32 is then obtained. The α-amino protective group can be split-off from this (carbobenzoxy for example hydrogenolytically, DPC with 90 % strength acetic acid or glacial acetic acidformic acid (82.8 % strength) - water (7:1:2)) and the compound thus obtained having a free α-amino group, can, after removal of the acetic acid be linked to the N-terminal decapeptide (FIGS. 1–8), for example by the method of mixed anhydrides, the method of activated esters (OSU) or according to Weygand-Wünsch.

It is however also possible to link the sequence 11–28 having a free C-terminal carboxyl group, after splitting-off the α-amino protective group in the manner mentioned, with the N-terminal decapeptide by the method of mixed anhydrides and to condense the product thus obtained with the tetrapeptide-amide 29–32, for example according to Weygand-Wünsch.

A further possibility for the synthesis of the C-terminal sequence 11–32 for example consists of building it up from the partial sequences 11–19 and 20–32 which are shown in FIGS. 14 and 15, preferably by the method of mixed anhydrides or according to Weygand-Wünsch.

According to the scheme in FIG. 15 it is also possible to manufacture the C-terminal sequence with a free carboxyl group. In this case, for example, the tert. butyl ester group present at the aminoacid 32 is not split off and converted to the amide group, but is retained up to stage J. The condensation of sequence 20–32 having a C-terminal free carboxyl group with the sequence 11–19 of FIG. 14 is for example effected by the method of mixed anhydrides, as is the linkage of the sequence 11–32 thus obtained with the N-terminal sequence 1–10.

The protective groups are split off from the protected dotriacontapeptide-amide, for example by means of trifluoracetic acid or with concentrated hydrochloric acid.

The dotriacontapeptide with free or trityl-protected SH— groups which is to be used for the process according to variant (2) can be manufactured in an analogous manner to the protected dotriacontapeptide described above, with the difference that the protected SH-groups are retained up to the end of the synthesis. Only after all other protective groups have been removed from the protected dotriacontapeptide are the SH-protective groups split off or is the trityl-protected compound directly oxidised as mentioned above.

The process according to variant (3) is particularly suitable for the manufacture of end products in which the α-amino group and the side-chain amino group are acylated. The $N^\alpha$ -acylated decapeptide can for example be manufactured according to FIG. 5 K; it is however also possible from the start to choose the acyl group to be retained as the amino protective group. The methods of synthesis correspond to those described above.

Depending on the procedure, the new compounds are obtained in the form of bases or of their salts. The bases can be obtained from the salts in a manner which is in itself known. In turn, salts can be obtained from the bases by reaction with acids which are suitable for the formation of therapeutically usable salts, such as for example salts with inorganic acids such as hydrogen halide acids, for example hydrochloric acid or hydrobromic acid, perchloric acid, nitric acid or thiocyanic acid, sulphuric or phosphoric acids, or organic acids such as formic acid, acetic acid, propionic acid, glycollic acid, lactic acid, pyruvic acid, oxalic acid, malonic acid, succinic acid, maleic acid, fumaric acid, malic acid, tartaric acid, citric acid, ascorbic acid, hydroxymaleic acid, dihydroxymaleic acid, benzoic acid, phenylacetic acid, 4-aminobenzoic acid, 4-hydroxybenzoic acid, anthranilic acid, cinnamic acid, mandelic acid, salicylic acid, 4-aminosalicylic acid, 2-phenoxybenzoic acid, 2-acetoxybenzoic acid, methanesulphonic acid, ethanesulphonic acid, hydroxyethanesulphonic acid, benzenesulphonic acid, p-toluenesulphonic acid, naphthalenesulphonic acid or sulphanilic acid.

The peptides obtained in accordance with the process may be employed in the form of pharmaceutical preparations. These contain the peptides mixed with a pharmaceutical, organic or inorganic excipient suitable for enteral or parenteral application. Possible excipients are such substances as do not react with the polypeptides such as for example gelatines, lactose, glucose, sodium chloride, starch, magnesium stearate, talc, vegetable oils, benzyl alcohols, gum, polyalkylene glycols, white petroleum jelly, cholesterol or other known medicinal excipients. The pharmaceutical preparations can for example be in the form of a lyophilisate or in a liquid form as solutions, suspensions or emulsions. They are optionally sterilised and/or contain auxiliary substances such as preservatives, stabilisers, wetting agents or emulsifiers. They may also furthermore contain other therapeutically valuable substances.

The invention is described in the examples which follow.

The following systems are used in the thin layer chromatography:

System 37: n-butanol-pyridine-water (46:31:23)
System 43A: tert.-amyl alcohol-isopropanol-water (100:40:10)
System 43C: tert. amyl alcohol-isopropanol-water (51:21:28)
System 43E: tert. amyl alcohol-isopropanol-water (32:32:36)
System 45: sec. butanol-3% strength aqueous ammonia (70:30)
System 52: n-butanol-glacial acetic acid-water (75:7.5:21)
System 52A: n-butanol-glacial acetic acid-water (67:10:23)
System 53: n-butanol-formic acid-water (60:0.75:39)
System 70: ethyl acetate-pyridine-water (40:20:40)
System 79: n-butanol-pyridine-water (34:33:33)
System 87: isopropanol-formic acid-water (77:4:19)
System 96: sec. butanol-glacial acetic acid-water (67:10:23)
System 100: ethyl acetate-pyridine-glacial acetic acid-water (62:21:6:11)

System 101: n-butanol-pyridine-glacial acetic acid-water (38:24:8:30)
System 101A: n-butanol-pyridine-glacial acetic acid-water (42:23:4:30)
System 102A: ethyl acetate-methyl ethyl ketone-formic acid-water (50:30:10:10)
System 102E: ethyl acetate-methyl ethyl ketone-glacial acetic acid-water (50:30:10:10)
System 104: chloroform-methanol-17% strength aqueous ammonia (41:41:18)
System 107: ethyl acetate-pyridine-water (49:24:27:)
System 110: ethyl acetate: n-butanol-pyridine-glacial acetic acid-water (42:21:21:6:10)
System 115: ethyl acetate-pyridine-formic acid-water (63:21:10:6)
System 121: isopropanol-ammonia (26% strength)-water (85:5:10)

System 1: benzene-ethanol (8:20)
System 2: benzene-ethanol (90:10)
System 3: benzene-ethanol (95:5)
System 4: n-amyl alcohol-formic acid-water (70:20:10)
System 5: n-butanol-acetic acid-water (66.6:16.7:16.7)
System 6: n-butanol-pyridine-acetic acid-water (66.6:12.5:4.2:16.7)
System 7: n-amyl alcohol-pyridine-water (50:30:20)
System 8: chloroform-methanol-glacial acetic acid (87.4:9.7:2.9)
System 9: benzene-ethanol (70:30).

Thin-layer chromatography is performed on silica gel or alumina ("Alox" D-O of Messrs. Camag with 8% of gypsum) or on "Selecta 1440" cellulose (of Messrs. Schleicher und Schüll).

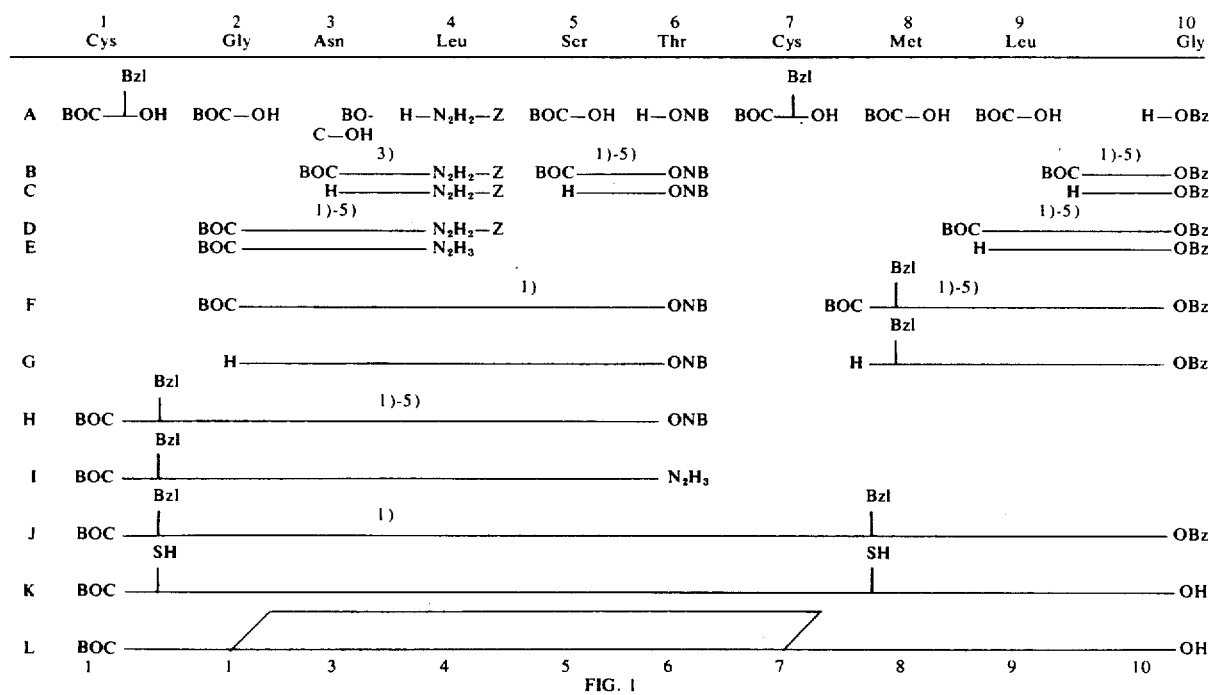

FIG. 1

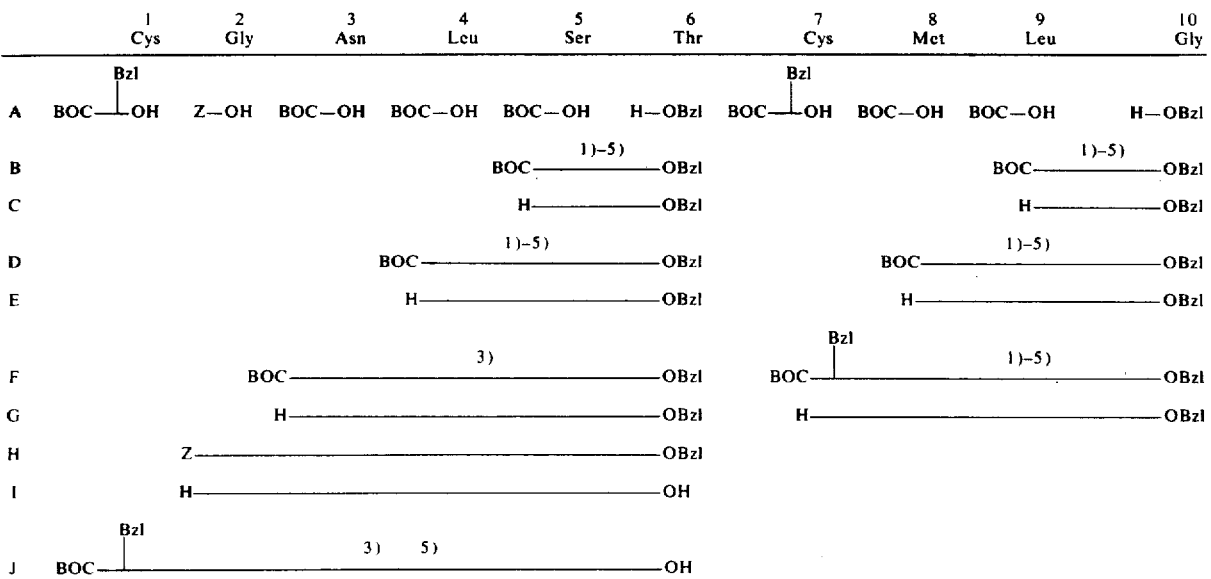

FIG. 2

FIG. 3

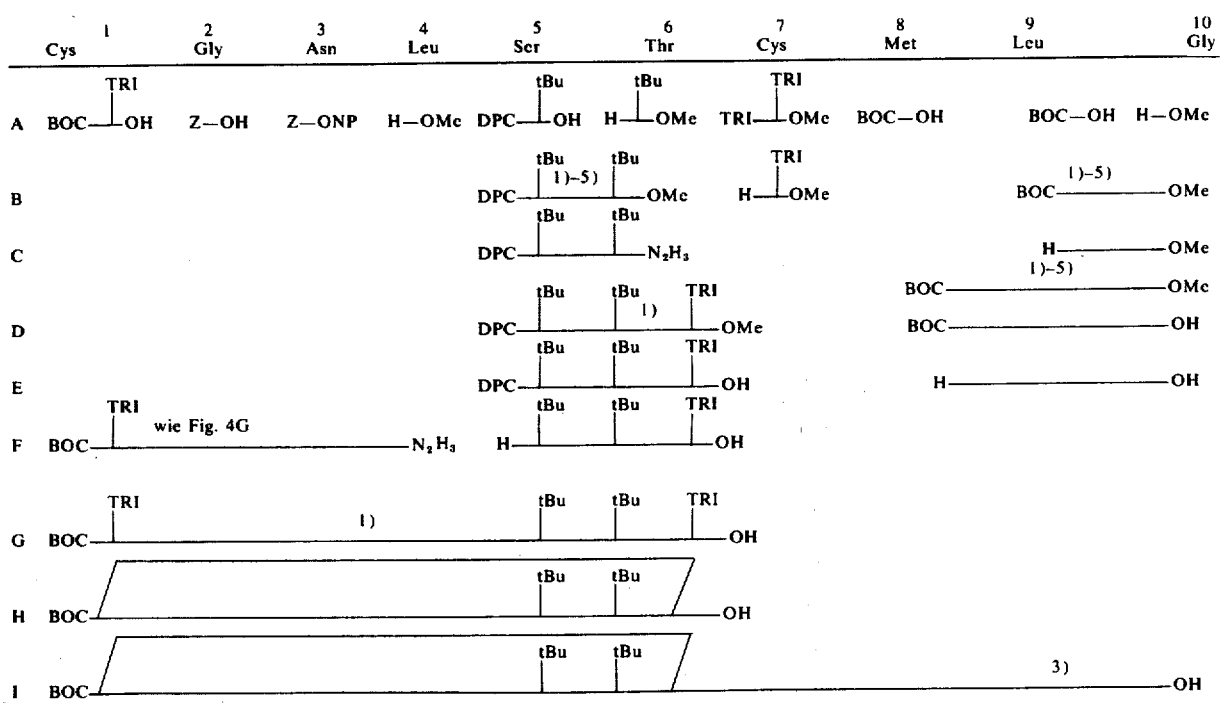
Fig. 6
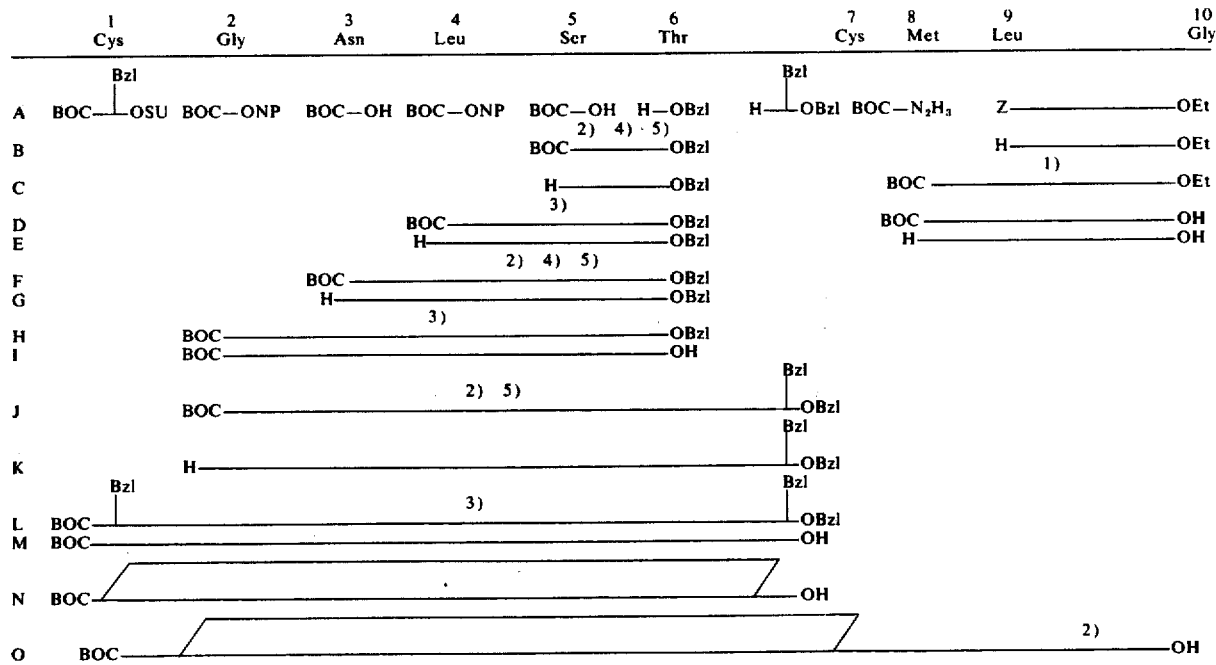
Fig. 7
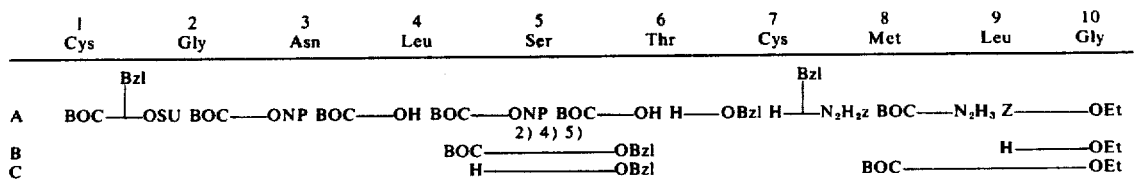

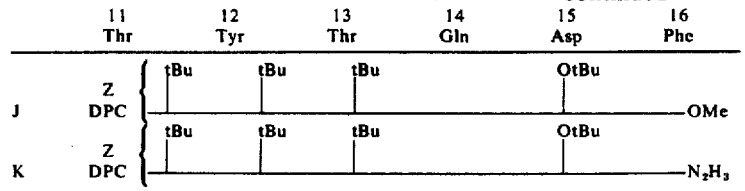
FIG. 10
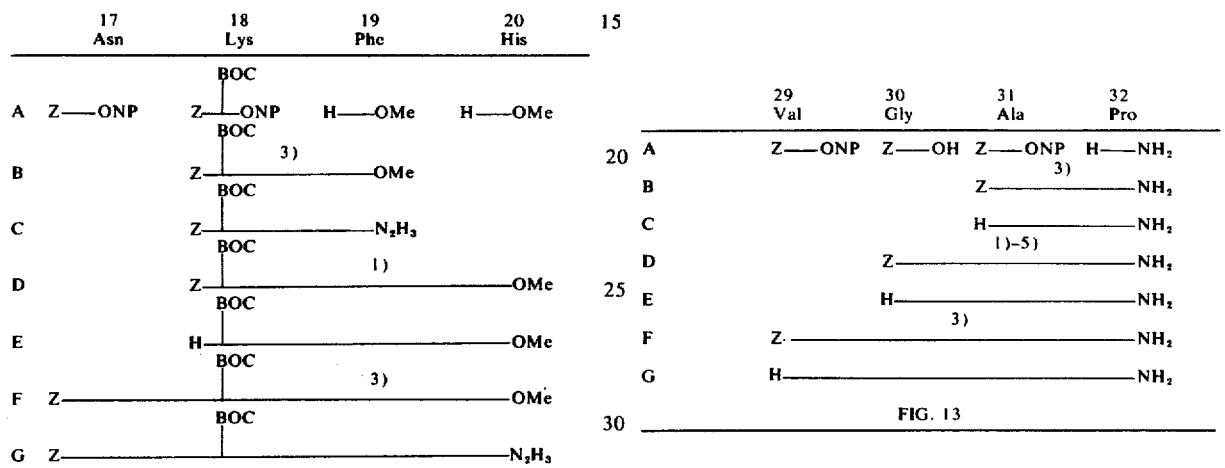
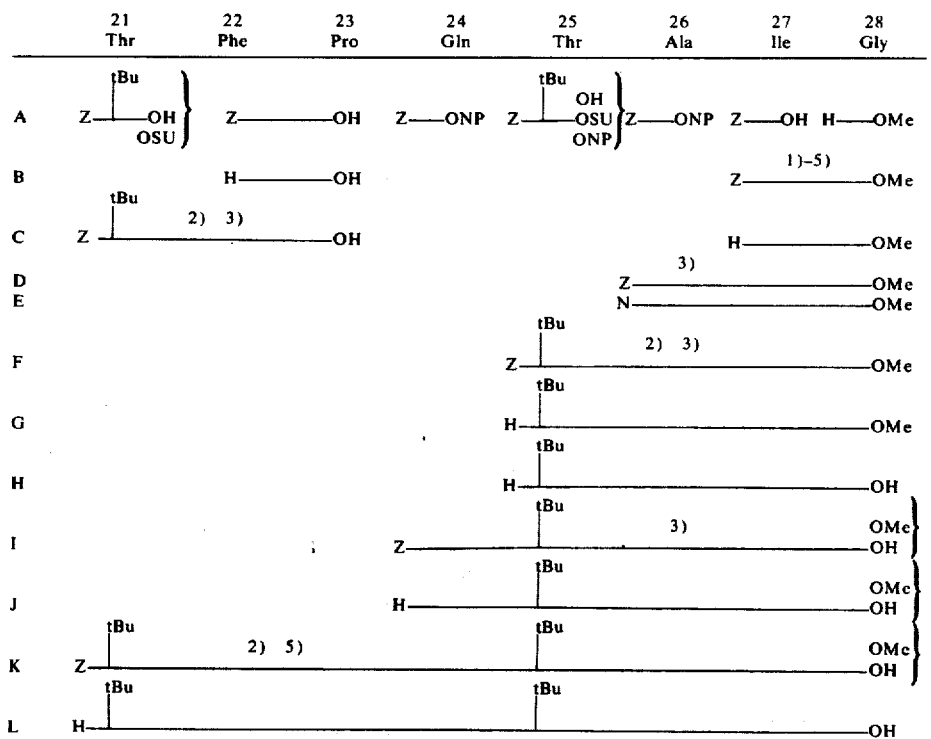

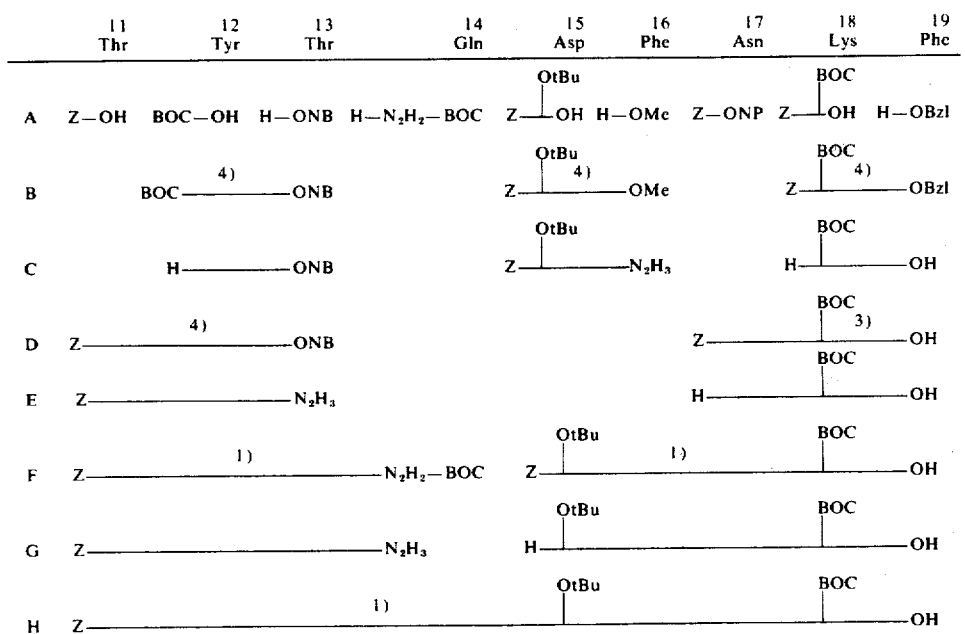

FIG. 14

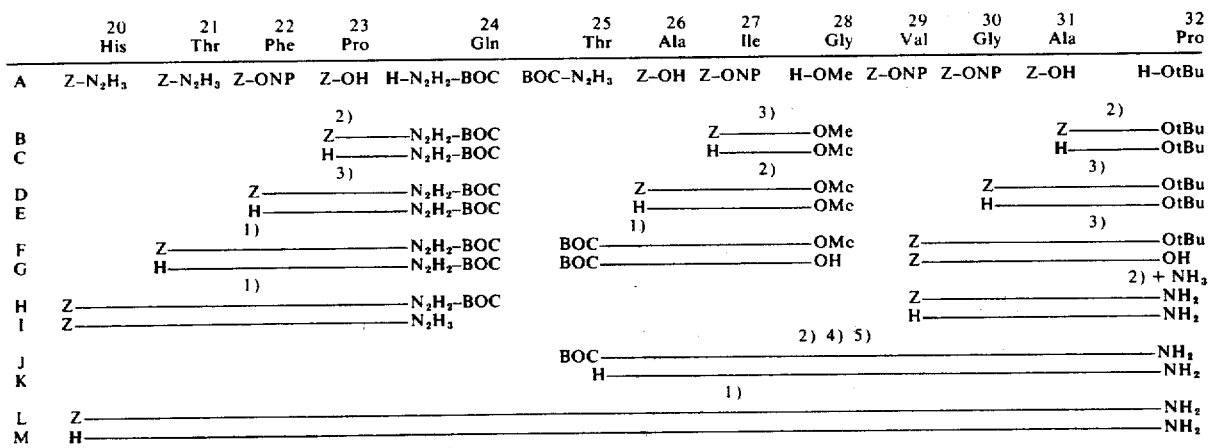

FIG. 15

EXAMPLE 1

H-Cys-Gly-Asn-Leu-Ser-Thr-Cys-Met-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala-Pro-NH₂
(Calcitonine M)

150 mg of

BOC-Cys-Gly-Asn-Leu-Ser(tBu)-Thr(tBu)-Cys-Met-Leu-Gly-Thr(tBu)-Tyr(tBu)-Thr(tBu)-Gln-Asp(OtBu)-Phe-Asn-Lys-(BOC)-Phe-His-Thr(tBu)-Phe-Pro-Gln-Thr(tBu)-Ala-Ile-Gly-Val-Gly-Ala-Pro-NH₂ are dissolved in 3 ml of 95 % strength trifluoracetic acid, flushed with nitrogen and allowed to stand for 90 minutes at 25°C. The trifluoroacetate of the liberated dotriacontapeptide-amide is then precipitated as an amorphous powder by adding 60 ml of absolute and peroxide-free ether, centrifuged off, suspended in 10 ml of fresh ether, again centrifuged, and the residue dried at 30°C. In order to convert it to the acetate, the trifluroacetate is dissolved in 3 ml of water and filtered through a column of weakly basic ion exchanger (for example Merck No. II; $\phi = 7.5$ mm; $l = 20$ cm) which has been equilibriated with 0.02 N acetic acid. The column is washed with 0.02 N acetic acid until it gives a negative Folin reaction, and the eluate is concentrated to a volume of about 5 ml and filtered through a column of Bio-Gel P 6, equilibriated in 0.1 N acetic acid (volume of the gel bed = 200 ml). The eluate analysed by thin layer chromatography (Alox, System 52). The main fractions, (maximum at about 100 - 120 ml) are combined, concentrated to dryness in a rotational evaporator (internal temperature not exceeding 20°C), again dissolved in 5 ml of water and lyophilised. The product thus obtained is, for the purpose of final purification, subjected to a Craig distribution through 500 stages in the solvent system n-butanol-glacial acetic acid-water (4:1:5, by volume) using phase volumes of 3 ml each. The chromatographically and electrophoretically homogenous dotriacontapeptide-amide is isolated as a white amorphous powder from distribution elements No. 141-180 (maximum at No. 162; K = 0.48) on evaporation to dryness (rotational evaporator, internal temperature at most 20°C), dissolving in 0.1 N acetic acid and lyophilising.

In thin layer chromatography the product has the following Rf-values:

| | |
|---|---|
| on "Alox" D-O (Messrs. Camag; aluminium oxide with 8% of gypsum) | Rf (52) = 0.56<br>Rf (79) = 0.66<br>Rf (45) = 0.45 |
| on cellulose "Selecta" 1440 (of Messrs. Schleicher and Schuell, ready-to-use plates) | Rf (45) = 0.51<br>Rf (101A) = 0.60 |

Electrophoresis on cellulose "Selecta" 1440
pH 1.9, 1½ hours, 280 V:
Migration distance = 3.5 cm to the cathode.
pH 7.1, 1½ hours, 280 V:
Migration distance = 1.3 cm to the cathode.
The starting material can be manufactured as follows:

1. Z-Asn-Leu-OMe 16.7 g of H-Leu-OMe and 46.0 g of Z-Asn-ONP are dissolved in 100 ml of freshly distilled dimethylformamide. The solution is allowed to stand for 19 hours at 25°C. Thereafter 1.2 liters of water are added and the crystalline precipitate is filtered off. The dipeptide derivative is dried at 40°C in vacuo and is then twice recrystallised from methanol-water. Melting point 180°-181°C; $[\alpha]^{20}_D = +9°$ (c = 2.05 in chloroform).

2. H-Asn-Leu-OMe 15.0 g of Z-Asn-Leu-OMe are dissolved in 400 ml of t-butanol-water (9:1) and are hydrogenated in the presence of 2 g of palladium on charcoal (10 % Pd). After completion of the hydrogenation the catalyst is filtered off and the filtrate evaporated at 40°C. The residue is directly used further.

3. Z-Gly-Asn-Leu-OMe 4.4 mmols of H-Asn-Leu-OMe are dissolved in 15 ml of dimethylformamide and 5.5 mmols of Z-Gly-p-nitrophenyl ester are then added. The clear yellow solution is left for 18 hours at 27°C. It is then evaporated in a high vacuum at 40°C, dried, and the residue mixed with ethyl acetate, whereupon it crystallises. After 1 hour at 0°C the product is filtered off and dried. The product is then again suspended in 25 ml of ethyl acetate, triturated, filtered off and dried; melting point 154°C.

4. H-Gly-Asn-Leu-OMe 1.3 g of Z-Gly-Asn-Leu-OMe are dissolved in 100 ml of methanol with warming and the solution, after having cooled to room temperature, is hydrogenated in the presence of 0.3 g of palladium on charcoal (10 % Pd). After completion of the hydrogen uptake the catalyst is filtered off and the filtrate evaporated to dryness. 760 mg of H-Gly-Asn-Leu-OMe are hereby obtained in an amorphous form.

5. BOC-Cys(TRI)-Gly-Asn-Leu-OMe 710 mg of H-Gly-Asn-Leu-OMe and 1.36 g of BOC-Cys(TRI)-OH are dissolved in 12 ml of acetonitrile and the solution, after having cooled to 0°C, is mixed with 820 mg of dicyclohexylcarbodiimide. After 30 minutes at 0°C and 60 hours at 28°C the dicyclohexylurea is filtered off and the filtrate is evaporated to dryness. The residue is mixed with petroleum ether, triturated, and the petroleum ether solution decanted and the insoluble product taken up in ethyl acetate. The ethyl acetate solution is washed at 0°C with dilute citric acid solution, water, sodium bicarbonate solution and water, dried with sodium sulphate and evaporated. The tetrapeptide derivative obtained as a colourless resin is repeatedly precipitated from acetone-ether in order to purify it. Yield: 1.2 g of powder which according to thin layer chromatography on silica gel is homogeneous; Rf = 0.39 in the system chloroform-methanol (9:1).

6. BOC-Cys(TRI)-Gly-Asn-Leu-NHNH₂

988 mg of BOC-Cys(TRI)-Gly-Asn-Leu-OMe are dissolved in 20 ml of methanol and 2 ml of hydrazine hydrate are added to the solution which has been cooled to 0°C. After 14 hours at 2°C 200 ml of ice-cold 0.5 N acetic acid are added and the precipitate which separates out is thoroughly triturated, filtered off, washed with ice water until neutral and dried in a vacuum desiccator overnight. The crude BOC-Cys(TRI)-Gly-Asn-Leu-hydrazide is purified by twice reprecipitating it from methanol-water. On thin layer chromatography on silica gel plates, Rf = 0.2 in the system chloroform-methanol (9:1).

7. BOC-Met-Leu-Gly-OMe 5 g of Z-Leu-Gly-OMe (J. Am. Chem. Soc. 78, 2126 (1956)) are dissolved in 200 ml of methanol and the solution which has been cooled to 0°C is hydrogenated at 0°C in the presence of 1 g of palladium on charcoal (10% Pd) with intensive stirring. After completion of the hydrogenation the catalyst is filtered off and the filtrate is evaporated in vacuo at 25°C bath temperature. The oily residue is, without drying, mixed with 4 g of BOC-methionine and the mixture is dissolved in 100 ml of acetonitrile. The solution is then concentrated in vacuo to a volume of 60 ml, cooled to 0°C, and 4.5 g of dicyclohexylcarbodiimide are added. After degassing with nitrogen the mixture is left for 30 minutes at 0°C and 18 hours at 25°C. The dicyclohexylurea which has separated out is then filtered off and the filtrate is concentrated to dryness. The residue is washed with petroleum ether with trituration, the petroleum ether solution is decanted and the insoluble product is dried. It is then dissolved in ethyl acetate and the solution is washed with dilute citric acid solution, water, sodium bicarbonate solution and water, dried with sodium sulphate and evaporated. In order to purify it, the residue is dissolved in the minimum quantity of peroxide-free acetone and precipitated by adding peroxide-free ether; hereupon the tripeptide derivative BOC-Met-Leu-Gly-OMe is obtained as a solid powder.

8. H-Met-Leu-Gly-OMe 3 g of the tripeptide derivative obtained under 7) are mixed with 60 ml of 0.4 N HCl in ethyl acetate and the reaction mixture is left for 90 minutes at 25°C. It is then evaporated to dryness and the residue (H-Met-Leu-Gly-OMe hydrochloride) is dried for 24 hours over sodium hydroxide at 0.01 mm Hg.

9. TRI-Cys(TRI)-Met-Leu-Gly-OMe 1.23 g of H-Met-Leu-Gly-OMe. HCl and 1.43 g of TRI-Cys (TRI)-OH are mixed with 15 ml of acetonitrile and 300 mg of N-methylmorpholine. After cooling to 0°C, 800 mg of dicyclohexylcarbodiimide are added and the reaction mixture is left for 1 hour at 0°C and 45 hours at 30°C under nitrogen. Solid material is then filtered off, the filtrate evaporated to dryness in vacuo and the residue triturated with petroleum ether. The petroleum ether solution is decanted and the residue is dried and dissolved in ethyl acetate. The ethyl acetate solution is washed at 0°C with citric acid solution, water, sodium bicarbonate solution and water, and is dried with sodium sulphate and evaporated. In order to purify it, the crude product (faintly yellowish resin) is dissolved in as little methanol as possible and the solution is chromatographed on a column of Sephadex LH-20 (2.5 + 90 cm) which has been prepared in methanol. Fractions of 4 ml each are collected, individually evaporated, and their purity checked by means of thin layer chromatography on silica gel plates in the system chloroform-methanol (99:1).

10a. H-Cys(TRI)-Met-Leu-Gly-OMe 1.11 g of the tetrapeptide derivative obtained under 9) are dissolved in 15 ml of 75 % strength acetic acid and left for 1 hour at 30°C. The solution is then evaporated to dryness in a high vacuum and the residue is triturated with peroxide-free ether. The solid powder thereby obtained (acetic acid salt of H-Cys(TRI)-Met-Leu-Gly-OMe) is filtered off, washed with ether and dried. Yield: 695 mg.

10b. H-Cys(TRI)-Met-Leu-Gly-OH 740 mg of H-Cys(TRI)-Met-Leu-Gly-OMe are dissolved in 10 ml of methanol and 1.3 ml of water with warming. 3.0 ml of 1.0 N sodium hydroxide solution are added dropwise at room temperature whilst flushing with nitrogen and the mixture is stirred for 25 minutes. It is then cooled to 0°C, 3.0 ml of 1.0 N hydrochloric acid and 20 ml of water are added and the flocculent precipitate is filtered off, washed with cold water and dried at room temperature over sodium hydroxide in a high vacuum to constant weight. $Rf_{70}$ = 0.40; $Rf_{121A}$ = 0.45.

11. H-Thr(tBu)-OMe 12.92 g (40 mmols) of Z-Thr(tBu)-OMe are hydrogenated in 200 ml of glacial acetic acid and 3 g of Pd on charcoal (10 %) at room temperature. The absorption of hydrogen is complete after 1 hour. The solution is freed of the catalyst by filtration and is evaporated under a waterpump vacuum at 35°C. After drying in a high vacuum at 35°C, 7.3 g of an oil result which according to a thin layer chromatogram is homogeneous and is directly used further.

12. DPC-Ser(tBu)-Thr(tBu)-OMe 19.3 g (38.6 mmols) of DPC-Ser(tBu)-OH.cyclohexylamine salt are taken up in 500 ml of chloroform and extracted at 0°C by shaking three times with 25 ml of 1 N citric acid and five times with 40 ml of half-saturated sodium chloride solution. The solution is dried over sodium sulphate and then evaporated and the resulting foam is taken up in 250 ml of ethyl acetate. 5.36 ml (38.6 mmols) of triethylamine are added and the solution is cooled to −10°C and mixed with 5.13 ml (38.6 mmols) of isobutyl chlorocarbonate whilst stirring. The mixture is stirred for 10 minutes at −10°C and a solution of 7.3 g (38.6 mmols) of H-Thr(tBu)-OMe in 100 ml of ethyl acetate, cooled to −12°C, is then added dropwise in such a way that the reaction temperature never exceeds −10°C. After completion of the addition the mixture is stirred for a further hour at − 10°C and is then left to stand overnight at room temperature. The solution is freed of the triethylamine hydrochloride which has separated out by filtering it and is washed at 0°C, three times with 20 ml at a time of 1 N citric acid and five times with saturated sodium chloride solution, dried and evaporated. Crude product (oil); 22.07 g. To purify it, 1 g is chromatographed on a silica gel column (2.5 cm, 30 cm). Using petroleum ether-ethyl acetate (1:1), 787 mg of pure product are eluted after a first run of 110 ml.

In a thin layer chromatogram on silica gel in toluene-acetone (7:3), Rf = 0.51.

13. DPC-Ser(tBu)-Thr(tBu)-NH-NH₂

4.253 g (7.4 mmols) of DPC-Ser(tBu)-Thr(tBu)-OMe in 18 ml of methanol are mixed with 5.55 ml (about 110 mmols) of hydrazine hydrate and left to stand for 10 hours at room temperature and 2 hours at 40°C. The reaction solution is taken up in 450 ml of ethyl acetate and washed 4 times with half-saturated sodium chloride solution. The solution is dried over sodium sulphate, concentrated to about 15 ml, and mixed with about 5 ml of petroleum ether. Overnight 3.17 g of a hydrazide of melting point 132°–134°C crystallise out.

In a thin layer chromatogram on silica gel in toluene-acetone (7:3) Rf = 0.40.

14a. DPC-Ser(tBu)-Thr(tBu)-Cys(TRI)-Met-Leu-Gly-OMe 900 mg of DPC-Ser(tBu)-Thr(tBu)-NHNH₂ in 12 ml of dimethylformamide are mixed at −20°C with 2.0 ml of C 2.0 N HCl in ethyl acetate and then with 210 mg of p-butyl nitrite. After 15 minutes at −10°C a solution, cooled to −10°C, of 680 mg of the acetic acid salt of H-Cys(TRI)-Met-Leu-Gly-OMe in 9 ml of dimethylformamide is added dropwise and 350 mg of N-methylmorpholine are then further added. The reaction temperature should not exceed −5°C during these additions. The mixture is then stirred for 1 hour at −5°C and 18 hours at 25°C. It is then evaporated in vacuo, and thereafter in a high vacuum, to a small volume, and the crude product is precipitated by adding ice water. The product is thoroughly triturated, the aqueous solution is decanted and the insoluble hexapeptide derivative is dried. In order to purify it, it is precipitated twice from methanol solution by adding water and then twice from ethyl acetate solution by adding petroleum ether. 480 mg of DPC-Ser(tBu)-Thr(tBu)-Cys(TRI)-Met-Leu-Gly-OMe are obtained.

14b. DPC-Ser(tBu)-Thr(tBu)-Cys(TRI)-Met-Leu-Gly-OH 857 mg of DPC-Ser(tBu)-Thr(tBu)-NH-NH₂ in 8.0 ml of dimethylformamide are mixed at −10°C with 1.87 ml of 2.0 N hydrogen chloride in ethyl acetate and 0.19 ml of t-butyl nitrite. After 15 minutes at −10°C a solution of 665 mg of H-Cys(TRI)-Met-Leu-Gly-OH and 0.665 ml of triethylamine in 7 ml of dimethylformamide is added dropwise whilst flushing with nitrogen. The mixture is stirred for a further hour at −10°C and is allowed to stand for 24 hours at 0°C. Concentration of the reaction mixture to about 3 ml (high vacuum, 30°C) and precipitation with 50 ml of water yields a flocculent product which is filtered off, washed with water and dried over sodium hydroxide in a high vacuum. Purification by reprecipitation from benzene-hexane. Rf = 0.36 in the system chloroform-methanol (7:3).

15. DPC-Ser(tBu)-Thr(tBu)-Cys(TRI)-Met-Leu-Gly-OH 2.3 g of the hexapeptide derivative manufactured according to 14a) are dissolved in 100 ml of dioxane-water (4:1) and 5 ml of 1 N sodium hydroxide solution are added. After 90 minutes at 27°C the excess sodium hydroxide solution is buffered by adding a little solid carbon dioxide, the solution is concentrated in vacuo to a volume of about 10 ml and 80 ml of ice-cold 2 % strength aqueous citric acid solution are then added. The precipitated hexapeptide derivative is thoroughly triturated, filtered off, washed with several portions of ice water and dried in a vacuum desiccator.

16. H-Ser(tBu)-Thr(tBu)-Cys(TRI-Met-Leu-Gly-OH (acetic acid salt)

870 mg of the hexapeptide derivative obtained under 15) are dissolved in 15 ml of 80 % strength acetic acid and the solution is left for 6 hours at 30°C. It is then evaporated to dryness in a high vacuum at 30°C, the residue is dried for 1 hour at 30°C and then mixed with peroxide-free ether, and the resulting powder is thoroughly triturated. It is filtered off, rinsed with a large amount of ether and dried.

17. BOC-Cys(TRI)-Gly-Asn-Leu-Ser(tBu)-Thr(tBu)-Cys(TRI)-Met-Leu-Gly-OH 1.0 g of BOC-Cys(TRI)-Gly-Asn-Leu-NHNH$_2$ is dissolved in 20 ml of dimethylformamide and the solution cooled to −10°C is mixed, whilst stirring, with 1.5 ml of 2.0 N HCl in ethyl acetate and 143 mg of t-butyl nitrite. After 15 minutes at −10°C a further 10 ml of dimethylformamide cooled to −10°C, 1.0 g of finely powdered H-Ser(tBu)-Thr(tBu)-Cys(TRI)-Met-Leu-Gly-OH (acetic acid salt) and 400 mg of N-methylmorpholine are added. The reaction mixture is stirred under nitrogen for 1 hour at −10°C and 48 hours at 28°C. It is then concentrated to a volume of about 6 ml in a high vacuum and the decapeptide derivative is precipitated by adding 100 ml of ice water. The resulting precipitate is triturated, filtered off and dried in a vacuum desiccator over sodium hydroxide. In a thin layer chromatogram on a silica gel plate the product shows Rf in chloroform-methanol (=7:3 = 0.60).

18. BOC-Cys-Gly-Asn-Leu-Ser(tBu)-Thr(tBu)-Cys-Met-Leu-Gly-OH 300 mg of BOC-Cys(TRI)-Gly-Asn-Leu-Ser(tBu)-Thr(tBu)-Cys(TRI)-Met-Leu-Gly-OH are dissolved in 100 ml of methanol and added dropwise, over the course of 1 hour, to an intensively stirred solution of 400 mg of iodine in 120 ml of methanol. After completion of the addition the solution is stirred for a further 45 minutes, and is then cooled to 0°C and decolorised with 1 N aqueous sodium thiosulphate solution. It is then concentrated in vacuo to a volume of about 10 ml and the decapeptide derivative is precipitated by adding 100 ml of ice-cold 1 % strength aqueous acetic acid solution. After triturating, filtering and washing with ice water, the product is dried in a desiccator over sodium hydroxide. In order to purify it, the product is subjected to a countercurrent distribution in the system methanol-buffer-chloroform-carbon tetrachloride (10 : 3 : 5 : 4) (buffer: 29 ml of glacial acetic acid, 19 g of ammonium acetate, made up to 1 liter with water); the fractions containing the pure decapeptide derivative are combined and the solution is evaporated. In order to remove ammonium acetate, the product is dissolved in chloroform and the solution is washed three times with dilute citric acid solution and three times with water and is then evaporated to dryness. Thin layer chromatogram on a silica gel plate Rf$_{100}$ = 0.45; Rf$_{121A}$ = 0.55; Rf$_{70}$ = 0.40; Rf$_{43C}$ = 0.35.

19. Z-Asp(OtBu)-Phe-OCH$_3$ 3.0 g of phenylalanine methyl ester hydrochloride together with 6.17 g of Z-Asp(OtBu)-ONP are dissolved in 25 ml of absolute N,N-dimethylformamide to give a clear solution and are mixed with 1.93 ml of triethylamine whilst stirring. The deep yellow solution is stirred overnight at room temperature, is then taken up in a large amount of ethyl acetate, and is washed 3 times with dilute aqueous citric acid solution, 5 times with dilute aqueous soda solution and finally with saturated aqueous sodium chloride solution until the wash liquid remains neutral. After drying over sodium sulphate the solution is evaporated and the resulting oil, which is soluble in ether and in chloroform, is purified by column chromatography on silica gel (the substance is eluted with toluene and toluene/ether, 4 : 1); a colourless oily product is obtained.

On silica gel, the R$_f$-value in chloroform-methanol (9:1) is 0.75; in chloroform-acetone (1:1) it is 0.67.

20. H-Asp(OtBu)-Phe-OCH$_3$. HCl 770 mg of the dipeptide Z-Asp(OtBu)-Phe-OMe are dissolved in 200 ml of methanol and are decarbobenzoxylated with hydrogen in a duck-shaped shaking flask at room temperature, in the presence of 0.60 ml of hydrogen chloride in dioxane (3.0 N, 1.8 mmols) and 200 mg of palladium on charcoal catalyst (10 %). After completion of the very rapid hydrogen uptake the mixture is filtered, the filtrate evaporated, the residue taken up in ethyl acetate and freed of a little insoluble matter by filtration, and the product precipitated with ether.

In a thin layer chromatogram on silica gel in the system chloroform-methanol (9:1) Rf = 0.60; Rf 43C = 0.63.

21. Z-Gln-Asp(OtBu)-Phe-OCH$_3$ 550 mg of H-Asp(OtBu)-Phe-OCH$_3$. HCl together with 574 mg of Z-Gln-ONP are dissolved in 2.5 ml of absolute N,N-dimethylformamide and stirred with 0.20 ml of triethylamine for 15 hours at 30°–33°C bath temperature. Thereafter the product is extracted by shaking with a large amount of ethyl acetate as described under 19 and the solution is dried and evaporated.

22. H-Gln-Asp(OtBu)-Phe-OCH$_3$. HCl 4.4 g of Z-Gln-Asp(OtBu)-Phe-OCH$_3$ are decarbobenzoxylated with hydrogen at room temperature in a duck-shaped shaking flask after adding 2.4 ml of hydrogen chloride in dioxane (3.0 N, 7.2 mmols) and 900 mg of 10 % strength palladium on charcoal catalyst. After completion of the hydrogen uptake the mixture is filtered and the filtrate evaporated to dryness in vacuo. The yellowish solid residue is twice triturated with ether and used for the next step without further purification.

23. Z-Thr(tBu)-Gln-Asp(OtBu)-Phe-OCH₃

3.68 g of Z-Thr(tBu)-OH. dicyclohexylammonium salt dissolved in ethyl acetate are 3 times shaken with dilute aqueous citric acid solution and three times with saturated aqueous sodium chloride solution, and the solution is dried over sodium sulphate and evaporated. The water-clear oil resulting therefrom is stirred with 3.34 g of H-Gln-Asp (OtBu)-Phe-OCH₃. HCl in 40 ml of methylene chloride, 0.9 ml of triethylamine are added and a solution of 1.54 g of dicyclohexylcarbodiimide in 10 ml of methylene chloride is added dropwise. After rinsing this down with 10 ml of methylene chloride the suspension is stirred for 14 hours at room temperature. It is then placed for 2 hours in a refrigerator and the solid precipitate is filtered off, washed with a little methylene chloride, and the filtrate extracted by shaking with a large amount of ethyl acetate as described in 19. The amorphous evaporation residue is triturated with ether-hexane (1:1) and dried.

24. H-Thr(tBu)-Gln-Asp(OtBu)-Phe-OCH₃

4.3 g of Z-Thr(tBu)-Gln-Asp(OtBu)-Phe-OCH₃ in 300 ml of methanol are hydrogenated with 1 g of 10 % strength palladium on charcoal catalyst in the usual manner and after completion of the hydrogen uptake the mixture is filtered and the filtrate evaporated. The evaporation residue, a solid colourless foam, is employed for the next stage without further purification.

25. Z-Tyr(tBu)-Thr(tBu)-Gln-Asp(OtBu)-Phe-OCH₃

The acid is liberated from 3.5 g of Z-Tyr(tBu)-OH. dicyclohexylammonium salt in ethyl acetate by means of citric acid as described under 23 and the resulting clear oil is stirred with 3.29 g of H-Thr(tBu)-Gln-Asp(OtBu)-Phe-OCH₃ in 80 ml of acetonitrile. 1.31 g of dicyclohexylcarbodiimide in the solid form are added thereto and the mixture is stirred for 24 hours at room temperature. The precipitated dicylohexylurea is now filtered off, washed with a little actonitrile, and the filtrate evaporated to dryness. The residue is dissolved in a large amount of chloroform and extracted by shaking, namely three times with dilute aqueous citric acid solution, three times with dilute aqueous soda solution and four times with saturated sodium chloride solution. After drying over sodium sulphate the solution is evaporated and the residue is dissolved in methanol-ethyl acetate, (1:8) and precipitated with petroleum ether in the cold. The precipitation is repeated. The protected pentapeptide results in the form of a finely granular powder.

26. H-Tyr(tBu)-Thr(tBu)-Gln-Asp(OtBu)-Phe-OCH₃

4.0 g of Z-Tyr(tBu)-Thr(tBu)-Gln-Asp(OtBu)-Phe-OCH₃ in 100 ml of absolute pre-hydrogenated N,N-dimethylformamide are decarbobenzoxylated with hydrogen at room temperature with the addition of 1.4 g of 10 % strength palladium on charcoal. After completion of the hydrogen uptake the mixture is diluted with 400 ml of methanol, filtered and evaporated in vacuo. The colourless solid residue is used for the next stage without further purification.

27. Z-Thr(tBu)-Tyr(tBu)-Thr(tBu)-Gln-Asp(OtBu)-Phe-OCH₃

The acid is liberated from 2.85 g of Z-Thr(tBu)-OH. dicyclohexylammonium salt in ethyl acetate by means of citric acid as described under 23 and the resulting oil consisting of Z-Thr (tBu)-OH is stirred with 3.33 g of H-Tyr(tBu)-Thr(tBu)-Gln-Asp (OtBu)-Phe-OCH₃ in 80 ml of acetonitrile at room temperature. 1.20 g of dicyclohexylcarbodiimide are added thereto in the solid form and the mixture is stirred for 23 hours at room temperature. After filtering off the precipitated dicyclohexylurea, which is washed with three portions of acetonitrile each of 7 ml, the solution is evaporated in vacuo and the residue is three times precipitated from ethyl acetate/alcohol solution by means of petroleum ether.

28. Z-Thr(tBu)-Tyr(tBu)-Thr(tBu)-Gln-Asp(OtBu)-Phe-NHNH₂

1.3 g of Z-Thr(tBu)-Tyr(tBu)-Thr(tBu)-Gln-Asp(OtBu)-Phe-OCH₃ are dissolved in 30 ml of methanol and mixed at 0°C with 0.6 ml of hydrazine hydrate. The mixture is left for 3 days in the refrigerator, in the course of which a jelly-like precipitate separates out. This is solidified by adding ether, filtered off, and the residue recrystallised from ethanol/ether.

29. Z-Lys(BOC)-Phe-OMe 25.0 g of Z-Lys(BOC)-ONP and 10.7 g of H-Phe-OMe. HCl in 70 ml of dimethylformamide are mixed with 6.9 ml of triethylamine at room temperature whilst stirring and the mixture stirred for a further 18 hours. After dilution with ethyl acetate the mixture is washed with potassium carbonate solution until free of nitrophenol, extracted by shaking with 0.1 M citric acid and water, dried over sodium sulphate and evaporated to dryness in vacuo. The protected dipeptide of melting point 78°–80°C crystallises from ethyl acetate-hexane. Rf = 0.45 in a thin layer chromatogram on silica gel in the system chloroform-acetone (8:2).

30. Z-Lys(BOC)-Phe-NH-NH₂

27 g of the above dipeptide methyl ester are dissolved in 135 ml of warm methanol, mixed at room temperature with 25 ml of hydrazine hydrate and allowed to stand for 16 hours. The crystalline product is mixed with 135 ml of water, filtered off and thoroughly washed with water. Melting point 173°–174°C after recrystallisation from methanol-water. Rf = 0.3 in a thin layer chromatogram on silica gel in the system chloroform-methanol (95:5).

31. Z-Lys(BOC)-Phe-His-OMe 5.4 g of Z-Lys(BOC)-Phe-NH-NH₂ in 40 ml of dimethylformamide are mixed at −16°C with 6.8 ml of 3.66 N HCl in dioxane and then with 1.5 ml of t-butyl nitrite. After 10 minutes at −10°C to −15°C, 3.5 ml of triethylamine are added. 3.64 g of H-His-OMe. 2 HCl are added in the solid form and 4.2 ml of triethylamine are thereafter added dropwise. The mixture is allowed to warm to 0°C over the course of 1 hour, with a pH of about 7 being set up by adding a total of 0.8 ml of triethylamine. After stirring overnight at 0°C the mixture is poured into 250 ml of water and the smeary product is obtained in the form of a powder by triturating with water. In a thin layer chromatogram on silica gel in chloroform-methanol (9:1) Rf = 0.4. Melting point 136°–137°C (from ethyl acetate).

32. H-Lys(BOC)-Phe-His-OMe 6.8 g of Z-Lys(BOC)-Phe-His-OMe in 140 ml of methanol are hydrogenated in the presence of 1 g of 10 % strength Pd on charcoal. After completion of the hydrogenation the catalyst is filtered off, the filtrate evaporated to dryness and the residue immediately processed further.

33. Z-Asn-Lys(BOC)-Phe-His-OMe

The tripeptide methyl ester (5.4 g) obtained under 32 and 4.5 g of Z-Asn-ONP in 20 ml of dimethylformamide are stirred for 20 hours at room temperature. The peptide derivative is precipitated by adding ether-hexane, filtered off, and washed with ether until free of nitrophenol. It is purified by reprecipitation from dimethylformamide-ether. The product is homogeneous according to a thin layer chromatogram.

34. Z-Asn-Lys(BOC)-Phe-His-NH-NH$_2$ 3.97 g of Z-Asn-Lys(BOC)-Phe-His-OMe are dissolved in 20 ml of boiling methanol. 2.5 ml of hydrazine hydrate are added to the solution whilst it is still at about 30°C and the mixture is allowed to stand for 20 hours at room temperature. The peptide-hydrazine is precipitated by adding water, filtered off and washed with water until free of hydrazine. The product is reprecipitated from dimethylformamide-water.

35. Z-Thr(tBu)-Phe-Pro-OH 4 g of Z-Phe-Pro-OH are dissolved in methanol-water (4:1) and hydrogenated in the presence of palladium on charcoal (10 % Pd). After completion of the hydrogen uptake the catalyst is filtered off, the filtrate evaporated to dryness and the residue (H-Phe-Pro-OH) dried. It is mixed with 1.1 g of N-methylmorpholine and sufficient water for the product just to dissolve. The solution is diluted with dimethylformamide to the point that a clear solution remains and is then cooled to −5°C. A solution of the mixed anhydride of Z-Thr(tBu)-OH, which is prepared as follows, is added thereto:

3.6 g of Z-Thr(tBu)-OH are dissolved in 40 ml of absolute tetrahydrofurane, 1.8 ml of absolute triethylamine are added and the solution cooled to −10°C is mixed with 1.7 g of chlorocarbonic acid isobutyl ester. After 5 minutes at −10°C the entire reaction mixture is, regardless of the triethylamine hydrochloride which has separated out, added to the above dipeptide solution. The mixture is left for 1 hour at −5°C and 18 hours at 5°C. Insoluble matter is then filtered off, the eluate is freed of tetrahydrofurane in vacuo and of dimethylformamide in a high vacuum and the residue is mixed with sodium bicarbonate solution. The insoluble constituents are removed by washing with ether and the aqueous phase is covered with ethyl acetate and acidified. The tripeptide derivative is extracted with ethyl acetate and the ethyl acetate solution is washed with water until neutral. After drying over sodium sulphate and evaporating, Z-Thr(tBu)-Phe-Pro-OH is obtained as a colourless resin-like product. It is repeatedly reprecipitated from benzene-petroleum ether in order to purify it.

36. Z-Ile-Gly-OMe 2.23 g of Z-Ile-OH-dicyclohexylammonium salt are suspended in ethyl acetate and acidified with 0.2 M citric acid. The resulting ethyl acetate solution is washed until neutral, dried and evaporated to dryness. The residue is dissolved in 15 ml of acetonitrile, and 750 mg of H-Gly-OMe.HCl are added to the solution followed at 0°C, with stirring, by 0.84 ml of triethylamine. After 10 minutes 1.24 g of dicyclohexylcarbodiimide are added and the mixture is stirred overnight at 0°C. The precipitate is filtered off, the filtrate evaporated to dryness, and the residue taken up in 30 ml of ethyl acetate and filtered. The ethyl acetate solution is washed with 0.2 M citric acid and saturated sodium bicarbonate solution, dried and concentrated to about 10 ml in vacuo. After adding 25 ml of hexane the protected dipeptide crystallises out; melting point 120°–122°C. Rf = 0.53 in the system chloroform-methanol (95:5) in a thin layer chromatogram on silica gel.

37. H-Ile-Gly-OMe 3.36 g of Z-Ile-Gly-OMe are dissolved in 100 ml of methanol and 10 ml of 1 N hydrochloric acid and hydrogenated in the presence of 0.5 g of Pd on charcoal (10 %). After filtering off the catalyst the solvent is completely evaporated. The resulting foam is homogeneous in a thin layer chromatogram on silica gel; Rf = 0.26 in chloroform-methanol (95:5).

38. Z-Ala-Ile-Gly-OMe 2.39 g of the above dipeptide ester hydrochloride and 3.78 g of Z-Ala-ONP in 40 ml of dimethylformamide are mixed with 1.4 ml of triethylamine whilst stirring and the resulting suspension is stirred overnight at room temperature. After dilution with ethyl acetate the mixture is washed with dilute potassium carbonate solution until free of nitrophenol and is subsequently further washed with 0.1 M citric acid and water. A part of the tripeptide derivative remains undissolved during the extraction by shaking, and is filtered off. The ethyl acetate solution is completely evaporated after drying. The residue also consists of pure product. Melting point 190°–191°C, Rf = 0.5 in a thin layer chromatogram on silica gel in the system chloroform-methanol (95:5).

39. H-Ala-Ile-Gly-OMe 2.0 g of Z-Ala-Ile-Gly-OMe are dissolved in 40 ml of methanol with gentle warming and then hydrogenated in the presence of 300 mg of Pd on charcoal (10 %). After completion of the hydrogenation the catalyst is filtered off and the filtrate completely evaporated to dryness. The residue, which is homogeneous in a thin layer chromatogram, is immediately processed further.

40. Z-Thr(tBu)-Ala-Ile-Gly-OMe 1.36 g of the above tripeptide ester and 2.6 g of Z-Thr (tBu)-ONP are stirred in 3 ml of dimethylformamide for 20 hours at room temperature. The tetrapeptide derivative is precipitated by means of ether, filtered off and washed with ether until free of nitrophenol. The product is purified by reprecipitation from dimethylformamide-ether.

41. H-Thr(tBu)-Ala-Ile-Gly-OMe 5.66 g of the above carbobenzoxy compound are hydrogenated in 50 ml of dimethylformamide and in the presence of 1 g of Pd on charcoal (10 %). After filtering off the catalyst by filtering through a layer of 2 g of Norite the dimethylformamide is completely evaporated in a high vacuum at 40°C. The amorphous residue is further processed in the crude state.

42. H-Thr(tBu)-Ala-Ile-Gly-OH 4.3 g of the tetrapeptide methyl ester are dissolved in 43 ml of methanol with gentle warming. After cooling to 20°C 12 ml of 1 N sodium hydroxide solution are added. After 5, 10 and 15 minutes 5 ml of water are added in each case. After 1 hour at room temperature 12 ml of 1 N hydrochloric acid are added and the mixture is freed of methanol in vacuo and extracted with n-butanol. The butanol solution is washed with water until free of chloride and is then, without drying, evaporated to dryness in vacuo. The residue is employed for the next stage without further purification.

43. Z-Gln-Thr(tBu)-Ala-Ile-Glv-OH

The tetrapeptide derivative (4.2 g) obtained above is stirred for 24 hours at room temperature together with 4.8 g of Z-Gln-ONP and 1.35 ml of triethylamine in 30 ml of dimethylformamide. The product is precipitated by adding ether and is then filtered off and washed with ether until free of nitrophenol. After dissolving in n-butanol saturated with water, the mixture is extracted by shaking at 0°C with 1 N hydrochloric acid, then washed with water until free of chloride and evaporated in vacuo at 40°C without drying. The product is obtained in the pure form by again reprecipitating it from dimethylformamide-ether. After drying in a high vacuum at 40°C over phosphorus pentoxide an equivalent weight of 693 is obtained on potentiometric titration with 0.1 N-NaOH in 80 % strength methanol; the calculated figure is 680.

44. H-Gln-Thr(tBu)-Ala-Ile-Gly-OH . HCl 3.40 g of Z-Gln-Thr(tBu)-Ala-Ile-Gly-OH are dissolved in 70 ml of warm dimethylformamide. After cooling to room temperature, 5 ml of 1 N hydrochloric acid and 500 mg of Pd on charcoal (10 %) are added and the product hydrogenated. After completion of the hydrogenation the catalyst is filtered off by filtering through 1 g of Norite and the filtrate is concentrated to about 10 ml in a high vacuum at 40°C. This solution is added dropwise to 100 ml of ether and the precipitated material is filtered off and washed with ether. The product is dried in a high vacuum at room temperature and on potentiometric titration with 0.1 N sodium hydroxide solution in 80 % methanol proves to have a content of 91 %.

45. Z-Thr(tBu)-Phe-Pro-Gln-Thr(tBu)-Ala-Ile-Gly-OH 2.8 g of Z-Thr(tBu)-Phe-Pro-OH and 0.77 ml of absolute triethylamine are dissolved in 30 ml of dry tetrahydrofurane and the solution, cooled to −10°C, is added dropwise to 700 mg of isobutyl chlorocarbonate, care being taken for the temperature not to exceed −5°C. The mixture is then left for 10 minutes at −10°C and is thereafter added to a solution, precooled to −20°C, of 2.5 g of H-Gln-Thr(tBu)-Ala-Ile-Gly-OH.HCl in 65 ml of dimethylformamide-water (9:1). 1.2 ml of triethylamine are then added dropwise and the mixture is left for 1 hour at −10°C and for 18 hours at 0°C. It is thereafter concentrated, in vacuo and then in a high vacuum at 40°C bath temperature, to a volume of about 15 ml and then precipitated by adding 100 ml of ice-cold 2 % strength acetic acid. The product is filtered off, washed with ice water, dried and twice reprecipitated from methanol-water to purify it; yield 3.9 g of octapeptide derivative.

46. H-Thr(tBu)-Phe-Pro-Gln-Thr(tBu)-Ala-Ile-Gly-OH 3.6 g of the Z-Thr(tBu)-Phe-Pro-Gln-Thr(tBu)-Ala-Ile-Gly-OH obtained under 45) are dissolved in 100 ml of 80 % strength acetic acid and the solution is hydrogenated in the presence of 0.5 g of palladium on charcoal (10 % Pd). After completion of the hydrogen uptake the catalyst is filtered off and the solution is evaporated to dryness. The acetic acid salt of the octapeptide derivative, which is obtained as a colourless firn, is dried in a high vacuum.

47. Z-Asn-Lys(BOC)-Phe-His-Thr(tBu)-Phe-Pro-Gln-Thr(tBu)-Ala-Ile-Gly-OH 1.60 g of Z-Asn-Lys(BOC)-Phe-His hydrazide are mixed with 25 ml of dimethylformamide, the mixture is thereafter cooled to −20°C, and 4 ml of 2.5 N aqueous hydrochloric acid are then added. This mixture is stirred at −20°C until the hydrazide has completely dissolved. 2.0 ml of 1.0 N sodium nitrite solution are then added dropwise and the reaction mixture is warmed to −10°C and left for 20 minutes at −10°C. A solution of 1.50 g of H-Thr(tBu)-Phe-Pro-Gln-Thr(tBu)-Ala-Ile-Gly-OH (acetic acid salt) in 25 ml of 80 % strength dimethylformamide, cooled to −10°C, and 1.11 g of N-methylmorpholine, are then added. The reaction mixture is left for 16 hours at 0°C. It is then evaporated in a high vacuum to a volume of about 8 ml and precipitated by adding ice-cold 1 % strength acetic acid. After filtering off and drying in a vacuum desiccator, the crude product is twice reprecipitated from dimethylformamide-ethyl acetate in order to purify it. The yield of protected dodecapeptide is 2.1 g.

48. H-Asn-Lys(BOC)-Phe-His-Thr(tBu)-Phe-Pro-Cln-Thr(tBu)-Ala-Ile-Gly-OH 1.85 g of the above protected dodecapeptide are dissolved in 50 ml of 90 % strength acetic acid and hydrogenated in the usual manner in the presence of 0.4 g of palladium on charcoal (10 % Pd). The acetic acid salt of H-Asn-Lys(BOC)-Phe-His-Thr(tBu)-Phe-Pro-Gln-Thr(tBu)-Ala-Ile-Gly-OH which remains after filtering off the catalyst, evaporating the solution and drying in a high vacuum is further processed without further purification.

49. Z-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-OH 2.30 g of Z-Thr(tBu)-Tyr(tBu)-Thr(tBu)-Gln-Asp(OtBu)-Phe-NH-NH₂ are dissolved in 35 ml of dimethylformamide and 3.5 ml of 3 N aqueous hydrochloric acid are added to the solution cooled to −20°C. 2.7 ml of 0.9 N sodium nitrate solution are then added and the reaction mixture is allowed to stand for 20 minutes at −10°C. Thereafter a solution of 1.72 g of H-Asn-Lys(BOC)-Phe-His-Thr(tBu)-Phe-Pro-Gln-Thr(tBu)-Ala-Ile-Gly-OH (acetic acid salt) in 30 ml of 90 % strength dimethylformamide, cooled to −10°C, and 1.0 g of N-methylmorpholine are added dropwise. The mixture is allowed to stand for 18 hours at 0°c, concentrated in a high vacuum to an oily consistency, and the product precipitated by adding 100 ml of icecold 2 % strength citric acid solution. The precipitate is thoroughly triturated, centrifuged off, rinsed four times with small portions of ice water and dried in a vacuum desiccator over sodium hydroxide. In order to purify it, it is repeatedly reprecipitated from dimethylformamide-ethyl acetate.

50. Z-Ala-Pro-NH₂

2.28 g of H-Pro-NH₂ and 7.57 g of Z-Ala-ONP are dissolved in 20 ml of dimethylformamide and the yellow solution is allowed to stand for 18 hours at room temperature. It is then evaporated to dryness in a high vacuum, the residue is mixed with ethyl acetate and the resulting powder is thoroughly triturated. After filtering off and drying, 5.5 g of Z-Ala-Pro-NH₂ of melting point 164°–165°C are obtained.

51. Z-Gly-Ala-Pro-NH₂

5.1 g of the above dipeptide derivative are dissolved in 200 ml of a pre-hydrogenated t-butanol-water (9:1) mixture whilst warming. The solution is cooled to room temperature and hydrogenated in the presence of 1 g of palladium on charcoal (10 % Pd). After completion of the hydrogenation the solution is immediately evaporated to dryness at 30°C bath temperature and 0.01 mm Hg, the residue of H-Ala-Pro-NH₂ is dissolved in 300 ml of dimethylformamide cooled to −20°C, and a solution of the mixed anhydride of Z-Gly-OH prepared as below is then added: 3.7 g of Z-Gly-OH and 2.65 ml of absolute triethylamine are dissolved in 25 ml of absolute tetrahydrofurane and 1.85 g of chlorocarbonic acid ethyl ester are added dropwise to the solution, cooled to −10°C, whilst stirring and cooling, in such a way that the temperature does not exceed −5°C. Thereafter the mixture is cooled to −10°C, allowed to stand for 5 minutes, and then added, regardless of the triethylamine H-Ala-Pro-NH which has separated out, to the above solution of H-Ala-Pro-NH₂ After 1 hour at − 10°C and 18 hours at 0°C the solution is filtered and the filtrate is evaporated to dryness, in vacuo and then in a high vacuum. The residue is then mixed with 1 litre of chloroform, triethylamine hydrochloride is filtered off, and the chloroform solution is twice washed with 20 ml at a time of half-saturated sodium chloride solution, dried with sodium sulphate and evaporated. The resulting tripeptide derivative shows Rf = 0.58 (in methanol) on thin layer chromatography on silica gel.

52. H-Gly-Ala-Pro-NH₂

3.8 g of the crude tripeptide derivative obtained under 51 are hydrogenated as described under 51. The residue remaining after filtering off the catalyst and evaporating the solvent mixture shows Rf = 0.15 on thin layer chromatography on silica gel 'in methanol; yield 2.2 g.

53. Z-Val-Gly-Ala-Pro-NH₂

The crude tripeptide-amide obtained under 52 is dissolved in 30 ml of dimethylformamide. 4.1 g of Z-Val-p-nitrophenyl ester are added to the solution. After 18 hours at room temperature the yellow solution is evaporated to dryness, the residue is mixed with ethyl acetate, triturated and filtered off, the jelly-like powder is dissolved in 2 litres of chloroform, and the solution is twice washed with 20 ml in each case of 5 % strength citric acid and twice washed with half-saturated sodium chloride solution. The chloroform solution is then dried with sodium sulphate and evaporated. The evaporation residue is mixed with 100 ml of ethyl acetate whilst warming and after standing at 0°C the tetrapeptide derivative which has separated out as a solid powder is filtered off; melting point 205°–210°C, Rf-value on silica gel plates = 0.80 in chloroform-methanol (1:1).

54. H-Val-Gly-Ala-Pro-NH₂

1.1 g of Z-Val-Gly-Ala-Pro-NH₂ are dissolved in 50 ml of dimethylformamide and the solution is hydrogenated in the presence of 0.3 g of palladium on charcoal (10 % Pd). After completion of the hydrogen uptake the catalyst is filtered off, the solution is evaporated and the residue is dried in a high vacuum at 35°C bath temperature. Hereupon the tetrapeptide H-Val-Ala-Pro-NH₂ is obtained as a colourless substance, Rf-value = 0.20. (Silica gel plates, system chloroform-methanol=1:1).

55.
Z-Thr(tBu)-Tyr(tBu)-Thr(tBu)-Gln-Asp(OtBu)-Phe-Asn-Lys-(BOC)-Phe-His-Thr(tBu)-Phe-Pro-Gln-Thr(tBu)-Ala-Ile-Glv-Val-Gly-Ala-Pro-NH₂

800 mg of Z-Thr(tBu)-Tyr(tBu)-Thr(tBu)-Gln-Asp(OtBu)-Phe-Asn-Lys-(BOC)-Phe-His-Thr(tBu)-Phe-Pro-Gln-Thr(tBu)-Ala-Ile-Gly-Val-Gly-Ala-Pro-NH₂

800 mg of Z-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-OH, 510 mg of H-Val-Gly-Ala-Pro-NH₂ and 120 mg of N-hydroxysuccinimide are dissolved in 9 ml of dimethylformamide at 45°C whilst stirring and 120 mg of dicyclohexylcarbodiimide are thereafter added. The reaction mixture is stirred at 45°C for a total of 12 hours, with a further 20 mg of dicyclohexylcarbodiimide and 20 mg of N-hydroxysuccinimide being added after 3 hours and again after 7 hours. The mixture is then poured into 200 ml of ether and the fine precipitate is filtered off. In order to purify it, the product is subjected to a countercurrent distribution in the system methanol-buffer-chloroform-carbon tetrachloride (10:3:5:6, buffer as under 18).

56.
H-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-Val-Gly-Ala-Pro-NH₂

227 mg of the docosapeptide-amide obtained under 55 are dissolved in 10 ml of 90 % strength acetic acid and the solution is hydrogenated in the presence of 100 mg of palladium on charcoal (10 % Pd) with intensive stirring. After completion of the hydrogen uptake the catalyst is filtered off and the filtrate evaporated to dryness. The residue is dissolved in n-butanol saturated with water and extracted by shaking three times with small portions of 5 % strength sodium carbonate solution and twice with a little water. The butanol solution is then evaporated, without prior drying, in a high vacuum at 35°C bath temperature and the residue is dried in a high vacuum. 185 mg of the decarbobenzoxylated docosapeptide are thus obtained as a colourless resin.

57.

BOC-Cys-Gly-Asn-Leu-Ser(tBu)-Thr(tBu)-Cys-Met-Leu-Gly-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-Val-Gly-Ala-Pro-NH₂

181 mg of BOC-Cys-Gly-Asn-Leu-Ser(tBu)-Thr(tBu)-Cys-Met-Leu-Gly-OH, 288 mg of H-Thr(tBu)-Tyr(tBu)-Thr(tBu)-Gln-Asp-(OtBu)-Phe-Asn-Lys(BOC)-Phe-His-Thr(tBu)-Phe-Pro-Glu-Thr-(tBu)-Ala-Ile-Gly-Val-Gly-Ala-Pro-NH₂ and 23 mg of N-hydroxy-succinimide are dissolved in 2 ml of absolute dimethylformamide whilst warming and are mixed with 31 mg of dicyclohexylcarbodiimide after cooling to room temperature. The small glass vessel is then flushed with nitrogen, closed and left to stand for 15 hours at 45°C. The resulting crystalline dicyclohexylurea is filtered off, twice washed with 0.5 ml of dimethylformamide at a time, the filtrate concentrated to half its volume in a high vacuum and the crude product precipitated by adding 20 ml of benzene and 120 ml of petroleum ether. In order to purify it, the product is once again reprecipitated from methanol-benzene-hexane, filtered off and dried to constant weight at 45°C. The protected dotriacontapeptide-amide is thus obtained as an amorphous powder which on thin layer chromatography has a main spot and various by-products. It can, in this state, be employed for the splitting off of the protective groups.

EXAMPLE 2

H-Cys-Gly-Asn-Leu-Ser-Thr-Cys-Met-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala-Pro-NH₂ (Calcitonin M)

0.6 ml of concentrated hydrochloric acid are poured at 0°C over 23 mg of BOC-Cys-Gly-Asn-Leu-Ser(tBu)-Thr(tBu)-Cys-Met-Leu-Gly-Thr(tBu)-Tyr(tBu)-Thr(tBu)-Gln-Asp(OtBu)-Phe-Asn-Lys-(BOC)-Phe-His-Thr(tBu)-Phe-Pro-Gln-Thr(tBu)-Ala-Ile-Gly-Val-Gly-Ala-ProNH₂ and the vessel is flushed with nitrogen, closed and stirred at 0°C for 10 minutes. It is then cooled to about −60°C, evacuated in a high vacuum, and the solution concentrated to a syrup whilst slowly raising the temperature up to 0°C. After adding 0.4 ml of water the mixture is lyophilised, the residue dissolved in 0.2 ml of 0.1 N acetic acid, and the solution filtered through a column ($\phi = 6$ mm; $l = 100$ mm) of weakly basic ion exchanger (for example Merck No. II) which has been equilibrated with 0.1 N acetic acid, in order to convert the product to the acetate. The eluate is concentrated to a volume of 0.5 ml, lyophilised, post-dried at 40°C in a high vacuum and finally equilibriated with atmospheric humidity by allowing it to stand in an open vessel. The acetate on Calcitonin M is thus obtained as a water-soluble white powder.

The protected dotriacontapeptide-amide used as the starting material can be manufactured as follows:

1. H-Gly-Asn-Leu-OMe 2.0 g of Z-Gly-Asn-Leu-OMe (of melting point 158°–159°C after recrystallisation from methanol-water) are dissolved in 20 ml of methanol whilst warming and hydrogenated with 200 ml of palladium on charcoal (10 % Pd) until the hydrogen uptake has ended. The catalyst is filtered off and the filtrate concentrated to dryness at 40°C bath temperature, whereupon the tripeptide methyl ester is directly obtained in a crystalline pure form (1.34 g; melting point 138°–139°C). It can, if necessary, be recrystallised from methanol-ethyl acetate-petroleum ether. $Rf_{52}$ = 0.22 (on silica gel).

2. BOC-Cys-(TRI)-Gly-Asn-Leu-OMe 5.7 g of H-Gly-Asn-Leu-OMe, 9.2 g of BOC-Cys(-TRI)-OH and 4.16 g of N-hydroxysuccinimide are dissolved in 200 ml of dimethylformamide, cooled to 0°C, and mixed with 5.57 g of dicyclohexylcarbodiimide in the solid form whilst stirring. The mixture is stirred for a further 1 hour at 0°C, allowed to stand overnight at about 20°C and concentrated in a high vacuum to a volume of about 100 ml, and the dicyclohexylurea which has separated out is filtered off. The filtrate is then further concentrated in a high vacuum until a sticky mass forms, and this is dissolved in 200 ml of n-butanol and the solution successively washed with water, 5 % strength tartaric acid solution 1 N sodium bicarbonate and again with water. The solution is now concentrated to a volume of about 50 ml and the tetrapeptide derivative is precipitated therefrom by adding 300 ml of petroleum ether. The product is purified by reprecipitation from dimethylformamide-water and from methanol-ethyl acetate-petroleum ether and the tetrapeptide derivative is thus obtained as an amorphous powder of melting point 145°–148°C. It shows the following Rf-values in a thin layer chromatogram on silica gel: Rf 115 = 0.68; Rf (acetone) = 0.59; Rf (chloroform-methanol 8:2) = 0.60.

3. BOC-Cys-(TRI)-Gly-Asn-Leu-NHNH₂

2.7 g of BOC-Cys(TRI)-Gly-Asn-Leu-OMe are dissolved in 22 ml of methanol, cooled to 0°C and mixed with 2.2 ml of hydrazine hydrate. After about 30 minutes at 0°C the solution is allowed to stand overnight at about 20°C, again cooled to 0°C, and then mixed with 102 ml of 3 % strength ice-cold acetic acid. The precipitate is well homogenised, filtered off and washed on the filter with ice-cold 3 % strength acetic acid until the wash liquid gives a Folin-negative reaction and subsequently dried. 2.2 g of chromatographically pure tetrapeptide-hydrazide of decomposition point about 195°C are obtained. It shows the following Rf-values in a thin layer chromatogram on silica gel: Rf (chloroform-methanol 8:2) = 0.30; Rf (acetone-methanol 9:1) = 0.53.

4. BOC-Met-Leu-Gly-OMe 6.72 g of Z-Leu-Gly-OMe in 50 ml of methanol are hydrogenated with 500 mg of palladium on charcoal (10 % Pd) until the hydrogen uptake has ended. The solution is freed of catalyst by filtration and is concentrated in vacuo to about 10 ml, diluted with 30 ml of dimethylformamide and again concentrated in a high vacuum to about 20 ml. 7.7 g of BOC-Met-OCP are added thereto whilst cooling in ice, the clear solution is allowed to stand at 20°C for 6 hours and the solvent is evaporated in a high vacuum. The oily residue is dissolved in ethyl acetate and successively washed at 0°C with 5 % strength potassium hydroxide solution, 0.2 N hydrochloric acid and finally with water; the organic phase is dried over sodium sulphate and concentrated to dryness. The oily residue is crystallised from benzene-petroleum ether; melting point 126–127°C; on silica gel Rf 43 C = 0.66; Rf (toluene-acetone 1:1) = 0.58.

5. H-Met-Leu-Gly-OMe. Hydrochloride 3.24 g of BOC-Met-Leu-Gly-Ome are dissolved in 13 ml of 3.8 N hydrogen chloride in ethyl acetate and allowed to stand for 30 minutes at 20°C. On adding 100 ml of petroleum ether the tripeptide ester hydrochloride is precipitated as a sticky mass, and the supernatant solution is decanted off. On triturating with 100 ml of peroxide-free ether at 0°C a finely powdered produce is obtained which is filtered off and dried to constant weight over potassium hydroxide at room temperature in a desiccator. The compound is chromatographically pure but amorphous and strongly hygroscopic. It shows the following Rf-values on silica gel; Rf 43 C = 0.48; Rf (toluene-acetone 1:1) = 0.35.

6. TRI-Cys(TRI)-Met-Leu-Gly-OMe 3.22 g of TRI-Cys(TRI)-OH, 1.97 g of H-Met-Leu-Gly-OMe-hydrochloride and 0.74 ml of triethylamine are dissolved in 32 ml of acetonitrile and 1.54 g of dicyclohexylcarbodiimide are added in the solid form. The initially clear solution from which dicyclohexylurea separates out is allowed to stand for 16 hours at 20°C. It is then cooled to 0°C, 100 ml of water are added, the mixture is homogenised and the white precipitate is filtered off. It is washed with water, dried and then finely triturated with 50 ml of ethyl acetate for 5 minutes at 40°C. The insoluble dicyclohexylurea is filtered off at room temperature and washed with 20 ml of ethyl acetate. The tetrapeptide derivative is precipitated as a jelly-like precipitate from the filtrate by adding 300 ml of petroleum ether and is filtered off and dried. On reprecipitating this crude product from methanol-ethyl acetate-petroleum ether a chromatographically homogeneous product of melting point about 215°C is obtained. It shows the following Rf-values on silica gel: in the system: CHCl$_3$-methanol (97:3) Rf = 0.57; in n-butyl acetate Rf = 0.51.

7. H-Cys(TRI)-Met-Leu-Gly-OMe. Acetate 4 ml of water are added dropwise to a solution of 1.862 g of TRI-Cys(TRI)-Met-Leu-Gly-OMe in 16 ml of glacial acetic acid in such a way that the precipitate which forms always redissolves. The clear solution is stirred for 1 hour at room temperature and is then mixed with 12 ml of water at 0°C and filtered, and the precipitate is washed with cold 50 % strength acetic acid. The filtrate is evaporated in a high vacuum at 30°C to give an oil and the latter is triturated with water and lyophilised. The resulting white powder is dried for 15 hours over potassium hydroxide in a high vacuum. The product proves to be homogeneous in a thin layer chromatogram on silica gel. In toluene-acetone (7:3) Rf = 0.28 and in chloroform-methanol (95:5) Rf = 0.48.

8. DPC-Ser(tBu)-Thr(tBu)-Cys(TRI)-Met-Leu-Gly-OMe 2.284 g of DPC-Ser(tBu)-Thr(tBu)-NH-NH$_2$ (compare Example 1, subsection 13) in 15 ml of dimethylformamide are mixed at −20°C with 6.5 ml of 1.53 N hydrogen chloride in ethyl acetate and 0.51 ml of t-butyl nitrite and the mixture is stirred for 15 minutes at −10°C. After adding 1.4 ml of triethylamine a solution of 1.406 g of H-Cys(TRI)-Met-Leu-Gly-OMe-acetate in 10 ml of dimethylformamide, cooled to −10°C, is added dropwise. The pH of the reaction solution is then ~5. A pH of 7–8 is established by adding 2 drops of triethylamine in dimethylformamide [2.8 ml of triethylamine made up to 10 ml with dimethylformamide]. After 5, 10 and 20 minutes the pH is again raised to 7–8 by means of 2 drops of triethylamine solution at a time. Thereafter this value remains constant. The reaction solution is kept for 1 hour at −10°C and for 15 hours at 0°C. The triethylamine hydrochloride which has separated out is then filtered off and the filtrate evaporated at 30°C in a high vacuum to give an oil. On trituration with water a powder is obtained which is washed with water and then triturated with water and lyophilised. The hexapeptide derivative is obtained pure by twice triturating with 10 ml of benzene-petroleum ether (1:2). In a thin layer chromatogram on silica gel in toluene-acetone (7:3) Rf = 0.42.

8a. DPC-Ser(tBu)-Thr(tBu)-Cys(TRI)-OH 5.7 g of DPC-Ser(tBu)-Thr(tBu)-NH-NH$_2$ in 50 ml of dimethylformamide are mixed at −15°C with 16.35 ml of 1.53 N hydrogen chloride in ethyl acetate and 1.4 ml of t-butyl nitrite and allowed to stand for 15 minutes at −10°C. After adding 3.5 ml of triethylamine a solution, cooled to −10°C, of 3.63 g of H-Cys(TRI)-OH and 1.4 ml of triethylamine in 40 ml of dimethylformamide and 16 ml of water is added dropwise and the mixture is stirred for one hour at −10°C and kept for 15 hours at 0°C. The clear solution is evaporated at 40°C in a high vacuum, the residue is taken up in ethyl acetate and water and the organic phase is washed with 50 % saturated sodium chloride solution. The oil obtained after evaporation of the solvent is dissolved in a little ethyl acetate and added dropwise to 300 ml of petroleum ether (stirred at 0°C). The product precipitates as a slightly yellowish powder. In a thin layer chromatogram on silica gel in the system chloroform-methanol (7:3) Rf = 0.62.

8b. H-Ser(tBu)-Thr(tBu)-Cys(TRI)-OH 909 mg of DPC-Ser(tBu)-Thr(tBu)-Cys(TRI)-OH are dissolved in 10 ml of methylene chloride, mixed with 12 ml of monochloracetic acid in water [obtained from 75 g of chloracetic acid and 25 ml of water] and stirred for 15 minutes at room temperature. The solution is then cooled to 0°C, mixed with 50 ml of water and brought to pH 6.5 with concentrated ammonia. Hereupon the product precipitates as an oil. This is triturated 2 more times with water and is then taken up in t-butanol and lyophilised. Trituration of the lyophilised product with petroleum ether yields a homogeneous product. In a thin layer chromatogram on silica gel in chloroformmethanol (1:1) Rf = 0.40; in methanol Rf = 0.50.

9. H-Ser(tBu)-Thr(tBu)-Cys(TRI)-Met-Leu-Gly-OMe 2 g of DPC-Ser(tBu)-Thr(tBu)-Cys(TRI)-Met-Leu-Gly-Ome are dissolved in 40 ml of 80 % strength glacial acetic acid at 45°C and the solution is thereafter allowed to stand for 1 hour at 45°C. It is then concentrated to a volume of about 10 ml in vacuo and lyophilised. In order completely to remove the acetic acid, the residue is dissolved in 15 ml of tert. butanol and 1.5 ml of water and again lyophilised. A powdery residue is obtained which is dissolved in 5 ml of methanol and 20 ml of ethyl acetate and again precipitated by adding 150 ml of petroleum ether. After briefly allowing the mixture to stand at 0°C, the product is filtered off, washed with petroleum ether and dried. An amorphous powder of melting point 180°C is obtained which only retains traces of 2-(p-biphenylyl)-propanyl(-2) as the sole impurity. The hexapeptide is used in this form for further processing. It shows the following Rf-values in a thin layer chromatogram on silica gel: in chloroform-acetone (1:1) Rf = 0.48; in chloroformmethanol (9:1) Rf = 0.54; in toluene-acetone (1:1) Rf = 0.49.

1.4 g of hexapeptide methyl ester from 9) are dissolved at 45°C in 16 ml of 90 % strength methanol, and the solution is cooled to 20°C (whereupon the peptide partially again precipitates) and mixed with 4.32 ml of 1 N sodium hydroxide solution. The suspension is stirred for 25 minutes at 22°C (after about 15 minutes everything has dissolved to give a clear solution) and the hexapeptide is then precipitated as a finely flocculent precipitate by adding 4.32 ml of 1 N hydrochloric acid and 30 ml of water. The mixture is allowed to stand for a further 15 minutes at 0°C and is filtered, and the product is washed with water until the filtrate is free of chloride ions. After drying over potassium hydroxide and phosphorus pentoxide 1.3 g of crude product are obtained and this is purified by homogenizing for 5 minutes at 80°C with a mixture of 25 ml of dimethylformamide and 60 ml of benzene and precipitating by adding 120 ml of petroleum ether. After standing for 10 minutes at 0°C the product is filtered off, washed with benzene and petroleum ether and dried. The chromatographically pure hexapeptide derivative thus obtained shows a decomposition point of about 210°C and is very sparingly soluble in many solvents. On thin layer chromatography on silica gel Rf 45 = 0.39, Rf 52 = 0.77 and Rf 100 = 0.47.

10. H-Ser(tBu)-Thr(tBu)-Cys(TRI)-Met-Leu-Gly-OH

11.
BOC-Cys(TRI)-Gly-Asn-Leu-Ser(tBu)-Thr(tBu)-Cys(TRI)-Met-Leu-Gly-OH 1.04 g of BOC-Cys(TRI)-Gly-ASn-Leu-NH-NH$_2$ are dissolved in 8 ml of absolute dimethylformamide, cooled to −25°C, and 0.92 ml of 3.6 N hydrochloric acid in dioxane are slowly added dropwise thereto followed by 0.179 ml of tert.butyl nitrite. This mixture is stirred for 15 minutes at −10°C, cooled to −15°C and pipetted into a solution, cooled to −15°C, of 878 mg of H-Ser(tBu)-Thr(tBu)-Cys(TRI)-Met-Leu-Gly-OH and 0.588 ml of triethylamine in 12 ml of absolute dimethylformamide. The mixture is stirred for about 10 minutes at −10°C and for 3 hours at 0°C. In order to maintain a weakly basic reaction (pH about 8) 0.065 ml of triethylamine at a time are initially still added twice. The mixture is left to stand for 15 hours at 0°C and is then concentrated in a high vacuum until it assumes a pasty consistency. The decapeptide derivative is precipitated by adding 50 ml of methanol. The suspension is warmed for 5 minutes to 40°C, allowed to stand for 10 minutes at 0°C, and the precipitate is filtered off and washed with 20 ml of methanol. On drying in a high vacuum over potassium hydroxide and phosphorus pentoxide, the pure decapeptide derivative having an unsharp decomposition point at about 220°–230°C is obtained. It shows the following Rf-values in a thin layer chromatogram on silica gel: in the system chloroform-methanol (8:2) Rf = 0.28; in the system 70, Rf = 0.55; in the system 104, Rf = 0.75; in the system 121 A, Rf = 0.59.

12.
BOC-Cys-Gly-Asn-Leu-Ser(tBu)-Thr(tBu)-Cys-Met-Leu-Gly-OH 1.7 g of BOC-Cys(TRI)-Gly-Asn-Leu-Ser(tBu)-Thr(tBu)-Cys(TRI)-Met-Leu-Gly-OH are dissolved in 170 ml of hot dimethylformamide and after cooling to room temperature the solution is added, over the course of 1 hour, to an intensively stirred solution of 2.5 g of iodine in 500 ml of methanol. Thereafter the mixture is stirred for a further hour and the solution, cooled to 0°C, is the decolourised almost completely with 1 N sodium thiosulphate. After concentration of the solution in vacuo, finally in a high vacuum at 40°C, to about 100 ml the product is completely precipitated with ether, whereupon the oil which precipitates rapidly solidifies. After decanting the ether solution the residue is briefly dried in vacuo and then triturated with water. The precipitated decapeptide derivative is filtered off, washed with water and dried. In order to purify it it is dissolved in 25 ml of chloroform, a small amount of insoluble material is filtered off, and the filtrate is concentrated to about one-half and precipitated with hexane. The pure decapeptide derivative is obtained, and this shows Rf 100 = 0.48 in a thin layer chromatogram on silica gel.

13. Z-Asp(OtBu)-Phe-OCH$_3$ 30.3 g of Z-Asp(OtBu)-ONP and 18.3 g of H-Phe-OCH$_3$. HCl are together dissolved in 150 ml of dimethylformamide and 11.8 ml of triethylamine are added dropwise to the clear solution. The resulting suspension is stirred for 20 hours at room temperature, whereupon it turns deep yellow. Thereafter the mixture is concentrated to about 100 ml in vacuo, dissolved in 1 liter of ethyl acetate/chloroform (4:1) and three times extracted by shaking with 5 % strength citric acid, 19 times with about 2 N sodium carbonate, and with saturated sodium chloride solution until it gives a neutral reaction. The crude product, a yellow oil, in ether is treated with active charcoal and after seeding is crystallised from 650 ml of ether/hexane (1:1) in a refrigerator. Colourless needles of melting point 74.5° – 76.5°C form. In a thin layer chromatogram on silica gel the Rf-value in the system chloroformmethanol (95:5) = 0.74 and in chloroform-acetone (75:25) = 0.65.

14. H-Aps(tBu)-Phe-OCH$_3$ 48.6 g of Z-Asp(OtBu)-Phe-OCH$_3$ in 700 ml of methanol are decarbobenzoxylated in a duck-shaped flask at room temperature after adding 33.5 ml of 3 N hydrogen chloride in dioxane and 5 g of 10 % strength palladium catalyst on charcoal. After the hydrogen uptake has ended the mixture is filtered and the filtrate evaporated. 38.7 g of a white foam are obtained. In a thin layer chromatogram on silica gel in chloroformmethanol (9:1) Rf = 0.60; in chloroform-acetone (1:1) Rf = 0.58; Rf$_{102E}$ = 0.42. The product is employed for the subsequent condensation without additonal purification.

15. Z-Gln-Asp(OtBu)-Phe-OCH$_3$ 38.6 g of the H-Asp(OtBu)-Phe-OCH$_3$. HCl obtained are dissolved, together with 42.0 g of Z-Gln-ONP in 170 ml of dimethylformamide to give a clear slightly yellow solution and slowly mixed with 13.9 ml of triethylamine whilst stirring. An orange suspension is produced which is stirred for 24 hours at 30°–35°C bath temperature. During this time a further 40 ml of dimethylformamide and additionally also 1.39 ml of triethylamine are added.

In order to work up the mix, it is dissolved in 4 liters of chloroform and successively washed, in a 20-stage counter-current distribution apparatus (phase volumme: lower phase 400 ml, upper phase 200 ml per vessel) successively with 1 liter of 5 % strength citric acid solution, 400 ml of saturated sodium chloride solution, 6 liters of approximately 2 N soda and 2.8 liters of saturated sodium chloride solution. After drying and evaporating the tripeptide derivative slowly crystallises out from 1.8 l of ethanol in a refrigerator. Z-Gln-Asp(OtBu)-Phe-OCH$_3$ of melting point 186°–188°C is obtained.

In a thin layer chromatogram on silica gel the following Rf-values are obtained: in chloroform-methanol (9:1) Rf = 0.39; in chloroform-acetone (1:1) Rf = 0.24; Rf 102E = 0.69, Rf 89 = 0.46, Rf 43A = 0.65 $[\alpha]_D^{20}$ = −28°±1° (c =1.3 % in dimethylformamide).

16. H-Gln-Asp(OtBu)-Phe-OCH$_3$ 7.55 g of Z-Gln-Asp(OtBu)-Phe-OCH$_3$ are dissolved in 400 ml of methanol, mixed with 4.1 ml of 3 N hydrogen chloride in dioxane and hydrogenated in the presence of 2 g of palladium on charcoal (10 % Pd). After filtering off the catalyst and evaporating, H-Gln-Asp(OtBu)-Phe-OCH$_3$. HCl is obtained as a colourless foam. The following Rf-values are obtained in a thin layer chromatogram on silica gel: in chloroform-methanol (9:1) Rf = 0.13; in chloroform-acetone (25:75) Rf = 0.14; Rf$_{102E}$ = 0.22.

17. Z-Thr(tBu)-Gln-Asp(OtBu)-Phe-OCH$_3$

The entire amount of the hydrochloride from 16) together with 7.4 g of Z-Thr(tBu)-OSU is dissolved in 14 ml of dimethylformamide at room temperature and 1.72 ml of triethylamine are added dropwise to this solution whilst cooling in an ice bath. Thereafter the brownish suspension is stirred for 20 hours at room temperature. After the usual working up in a large amount of ethyl acetate (washing three times each with 5 % strength citric acid and approximately 2 N sodium carbonate, washing until neutral with saturated sodium chloride solution, drying over sodium sulphate and evaporating in vacuo at 30°–40°C) the crude product, in ethanol, is treated with active charcoal and crystallised from 90 ml of ethanol in a refrigerator. Melting point 155°–161°C. In a thin layer chromatogram on silica gel the following Rf-values are found: in chloroform-methanol (9:1) Rf = 0.52; in cyclohexane-acetone (3:7) Rf = 0.48; Rf$_{89}$ = 0.48, Rf$_{121A}$ = 0.76 $[\alpha]_D^{20}$ = −4°±0.5° (c = 2.3 % in dimethylformamide).

18. H-Thr(tBu)-Gln-Asp(OtBu)-Phe-OCH$_3$ 478 mg of Z-Thr(tBu)-Gln-Asp(OtBu)-Phe-OCH$_3$ in 150 ml of methanol are hydrogenated with 100 mg of palladium on charcoal (10 % strength) at room temperature under neutral conditions. 395 mg of a colourless foam of H-Thr(tBu)-Gln-Asp(OtBu)-Phe-OCH$_3$ are obtained and this is used without further purification for the subsequent condensation.

The following Rf-values are obtained in a thin layer chromatogram on silica gel: in chloroform-methanol (1:1) Rf = 0.75; in chloroform-methanol (9:1) Rf = 0.17; in acetone = 0.18; Rf$_{102E}$ = 0.23; Rf$_{89}$ = 0.12.

19. Z-Tyr(tBu)-Thr(tBu)-Gln-Asp(OtBu)-Phe-OCH$_3$ 687 mg of Z-Tyr(tBu)-OH-dicyclohexylammonium salt dissolved in chloroform are extracted by shaking with aqueous citric acid and the resulting free acid, a clear oil, dissolved in 6.5 ml of tetrahydrofurane is mixed with 0.139 ml of N-methylmorpholine. 0.170 ml of chloroformic acid isobutyl ester are added at −22°C and the mixture is stirred for half an hour at −22° to −10°C. The H-Thr(tBu)-Gln-Asp(OtBu)-Phe-OCH$_3$ described above, dissolved in 15 ml of tetrahydrofurane and pre-cooled, is then added dropwise and rinsed down with 5 ml of the same solvent. After half an hour at −10°C the mixture is stirred for a further 15 hours at room temperature. Thereafter it is concentrated in vacuo and worked up in ethyl acetate in the usual manner (compare 17 ). The crude product is dissolved in 15 ml of ethyl acetate, precipitated with 40 ml of ether and subsequently crystallised from methanol in a refrigerator. Short thick needles which disintegrate on drying in a high vacuum at 50°C. Melting point 169°–173°C. In a thin layer chromatogram on silica gel the following Rf-values are obtained: in chloroform-methanol (9:1) Rf = 0.46; in chloroform-methanol (1:1) Rf = 0.95; in chloroformacetone (1:1) Rf = 0.44; Rf$_{89}$ = 0.61; Rf$_{acetone}$ = 0.68; Rf$_{102E}$ = 0.73. $[\alpha]_D^{21}$ = −54° ± 0.5°(c = 2.0 % in dimethylformamide).

20. H-Tyr(tBu)-Thr(tBu)-Gln-Asp(OtBu)-Phe-OCH$_3$ 2.36 g of Z-Tyr(tBu)-Thr(tBu)-Gln-Asp(OtBu)-Phe-OCH$_3$ in 450 ml of methanol are hydrogenated with 500 mg of 10 % strength palladium on charcoal in the usual manner at room temperature. A colourless foam is obtained which is homogeneous according to a thin layer chromatogram and is further employed as such. The following Rf-values are obtained in a thin layer chromatogram on silica gel: in chloroform-methanol (95:5) Rf = 0.22; Rf$_{89}$ = 0.42.

21. Z-Thr(tBu)-Tyr(tBu)-Thr(tBu)-Gln-Asp(OtBu)-Phe-OCH$_3$

The product from 20) together with 1.48 g of Z-Thr(tBu)-OSU is dissolved in 3 ml of dimethylformamide and stirred for 21 hours at room temperature. After diluting the reaction solution with a large amount of ethyl acetate it is worked up in the usual manner (compare 17). The crude product is dissolved in 30 ml of warm ethyl acetate-methanol (9:1) and after cooling in an ice bath is precipitated with 80 ml of ether. The product obtained is a colourless amorphous powder of melting point 146°–148°C. The following Rf-values are obtained in a thin layer chromatogram on silica gel: in chloroform-methanol (9:1) Rf = 0.55; in chloroform-acetone (1:1) Rf = 0.60; Rf$_{89}$ = 0.43; $[\alpha]_D^{21}$ = +6 ± 0.5° (c = 2.0 in dimethylformamide).

22. Z-Thr(tBu)-Tyr(tBu)-Gln-Asp(OtBu)-Phe-NH-NH$_2$ 1.91 g of Z-Thr(tBu)-Tyr(tBu)-Thr(tBu)-Gln-Asp(OtBu)-Phe-OCH$_3$ are dissolved in 80 ml of methanol and mixed with 8 ml of hydrazine hydrate. After allowing to stand for 22 hours at room temperature, the product which has precipitated is isolated and dried in a high vacuum at 60°C. The microcrystalline hydrazide of melting point 226°–229°C (decomposition) is obtained. The following Rf-values are found in a thin layer chromatogram on silica gel: in chloroformmethanol (9:1) Rf = 0.32; in cyclohexane-acetone (3:7) Rf = 0.23; Rf$_{H9}$ = 0.34. [α]$_D^{20}$ = +4° ± 1° (c = 1.0 in dimethylformamide).

23. Z-Asn-Lys(BOC)-Phe-His-OMe 5.4 g of H-Lys(BOC)-Phe-His-OMe (compare Example 1) and 4.5 g of Z-Asn-ONP in 20 ml of dimethylformamide are stirred for 20 hours at room temperature. The peptide derivative is precipitated by adding ethyl acetate, filtered off and washed with ether. After recrystallisation from methanol the product melts at 182°–183°C. In a thin layer chromatogram RF$_{100}$ = 0.57 (on silica gel). [α]$_D^{20}$ = −28° (c = 1 in dimethylformamide).

24. Z-Asn-Lys(BOC)-Phe-His-NH-NH$_2$ 3.97 g of Z-Asn-Lys(BOC)-Phe-His-OMe are dissolved in 8 ml of warm dimethylformamide and 12 ml of methanol. 2.5 ml of hydrazine hydrate are added to the solution whilst it is still at about 30°C and the mixture is allowed to stand for 20 hours at room temperature. The peptide-hydrazide is precipitated by adding water, filtered off and washed with water until free of hydrazine. The product is recrystallised from ethanol, melting point = 200°–201°C. In a thin layer chromatogram on silica gel RF$_{43C}$ = 0.5.

25. H-Phe-Pro-OH

Z-Phe-Pro-OH is converted to the free dipeptide by catalytic reduction (Pd-charcoal) in methanol-water (4:1). After concentrating the hydrogenation solution which has been freed of catalyst to a small volume, the free dipeptide is obtained in a crystalline form by adding acetone, and in fact as the dipeptide monohydrate of melting point 125°–128°C.

26. Z-Thr(tBu)-Phe-Pro-OH 20.2 g of Z-Thr(tBu)-OSU, 13.3 g of H-Phe-Pro-OH (monohydrate) and 6.54 ml of triethylamine are dissolved in 80 ml of dimethylformamide, allowed to stand overnight at about 20°C and then concentrated in a high vacuum until a sticky mass forms. The latter is dissolved in 500 ml of ethyl acetate and washed five times with 100 ml at a time of 5 % strength tartaric acid solution and subsequently with water until neutral. The organic phase is concentrated to dryness and the remaining solid foam is powdered and dried in a high vacuum at 40°C. On twice reprecipitating from ethyl acetate-peptroleum ether 13.3 g of amorphous chromatographically pure tripeptide derivative having an unsharp melting range at about 75°–85°C are obtained. In a thin layer chromatogram on silica gel RF$_{115}$ = 0.68; Rf$_{121A}$ = 0.57.

27. Z-Thr(tBu)-Ala-Ile-Gly-OMe 1.36 g of H-Ala-Ile-Gly-OMe (compare Example 1) and 2.5 g of Z-Thr(tBu)-OSU in 3 ml of dimethylformamide are stirred for 20 hours at room temperature. The tetrapeptide derivative is precipitated by ether, filtered off and washed with ether. After recrystallisation from ethanol the melting point is 229°–230°C. [α]$_D^{20}$ = −43° (c = 1 in methanol). Rf = 0.55 in the system chloroform-methanol (95:5) on silica gel.

28. H-Thr(tBu)-Ala-Ile-Gly-OMe 5.66 g of the above carbobenzoxy compound are dissolved in 400 ml of warm methanol and hydrogenated in the presence of 1 g of Pd-charcoal (10 %). After filtering off the catalyst the methanol is evaporated in vacuo at 40°C. The solid residue is immediately further processed. Rf = 0.2 in the system chloroform-methanol (95:5) on silica gel.

29. H-Thr(tBu)-Ala-Ile-Gly-OH 4.3 g of the tetrapeptide-methyl ester are dissolved in 43 ml of methanol with gentle warming. After cooling to 20°C, 12 ml of 1 N sodium hydroxide solution are added. After 5 minutes 20 ml of water are added and after a further 10 minutes 12 ml of 1 N hydrochloric acid and 20 ml of methanol are added. The crystalline precipitate is filtered off and washed with 90 % strength ethanol. It melts from 240°C onwards, with decomposition. Rf$_{100}$ = 0.15 on silica gel.

30a. Z-Gln-Thr(tBu)-Ala-Ile-Gly-OH

The tetrapeptide derivative described under 29) (4.2 g) is suspended in 110 ml of 90 % strength dimethylformamide, mixed with 1.4 ml of triethylamine and warmed to 70°C until the greater part has dissolved. After cooling to 25°C, 4.8 g of Z-Gln-ONP are added, the mixture is stirred for 18 hours at room temperature, a further 2.4 g of Z-Gln-ONP and 0.7 ml of triethylamine are added and the mixture stirred for a further 20 hours at 50°C. The product which has precipitated is filtered off, the mother liquor is mixed with ether and the product which has precipitated is also isolated. Both fractions are together suspended in 60 ml of t-butanol, thoroughly triturated after adding 2 N hydrochloric acid until a pH of 2 is reached, and then precipitated by portion-wise addition of a total of 600 ml of water. The product is centrifuged off, washed two more times with 200 ml of water at a time and lyophilised. It can be recrystallised from a large amount of methanol. Melting point from 230°C onwards with decomposition. The product contains 5 mols of water. In a thin layer chromatogram on silica gel RF$_{100}$ = 0.4.

30b. Z-Gln-Thr(tBu)-Ala-Ile-Gly-OMe 4.6 g of the H-Thr(tBu)-Ala-Ile-Gly-OMe described under 28), in 30 ml of dimethylformamide, are mixed with 3.5 g of Z-Gln-ONP and stirred at room temperature until the mixture becomes solid. After allowing to stand overnight the mixture is diluted with ether and the precipitate is filtered off and washed with ether until free of nitrophenol. The protected pentapeptide shows Rf = 0.14 in the system chloroform-methanol (95.5) in a thin layer chromatogram on silica gel. Melting point: >250°C.

31a. H-Gln-Thr(tBu)-Ala-Ile-Gly-OH . HCl 3.7 g of Z-Gln-Thr(tBu)-Ala-Ile-Gly-OH are suspended in 150 ml of 80 % strength methanol and 5.5 ml of 1 N hydrochloric acid and hydrogenated in the presence of 2 g of Pd-charcoal (10 %) until the substance has dissolved and no further hydrogen uptake can be detected. After filtering off the catalyst the filtrate is extensively concentrated in vacuo at 30°C, diluted with t-butanol and lyophilised. In a thin layer chromatogram on silica gel RF$_{101}$ = 0.48.

31b. H-Gln-Thr(tBu)-Ala-Ile-Gly-OMe . HCl 14.4 g of the pentapeptide derivative described under 30b) are suspended in 800 ml of 80 % strength methanol and warmed to 50°C for some time. The suspension is cooled to room temperature, mixed with 20.8 ml of hydrochloric acid and 3 g of Pd-charcoal (10 % strength) and hydrogenated until the hydrogen uptake has ended and the starting material has dissolved. After filtering off the catalyst the filtrate is evaporated in vacuo at 40°C and the residue dehydrated by twice evaporating with dimethylformamide in a high vacuum. The residue is used without further purification. $Rf_{100} = 0.33$ in a thin layer chromatogram on silica gel.

32.
Z-Thr(tBu)-Phe-Pro-Gln-Thr(tBu)-Ala-Ile-Gly-OMe 12.0 g of the pentapeptide-methyl ester hydrochloride described under 31b) are dissolved in 80 ml of dimethylformamide. 13.3 g of Z-Thr(tBu)-Phe-Pro-OH and 5.75 g of N-hydroxysuccinimide are successively added at room temperature whilst stirring, followed at 0°C by 2.76 ml of triethylamine and 6.2 g of dicyclohexylcarbodiimide. The mixture is stirred at 0°C until it has become thick and is then allowed to stand overnight at 0°C. After concentrating in a high vacuum to about 50 ml, the product is precipitated with 300 ml of ether. The isolated material is washed with 0.05 M citric acid and water and is dried in a high vacuum at 40°C. The product is purified by recrystallisation from about 1 l of isopropanol. 18;2 g of the protected octapeptide derivative are obtained. $Rf_{89} = 0.27$ in a thin layer chromatogram on silica gel.

33. Z-Thr(tBu)-Phe-Pro-Gln-Thr(tBu)-Ala-Ile-Gly-OH 10.9 g of the octapeptide-methyl ester described under 32) are dissolved in 190 ml of 90 % strength methanol whilst warming to 70°C. After cooling at room temperature, 30 ml of 1 N sodium hydroxide solution are added, followed 10 minutes later by 160 ml of water added in small portions. The mixture is then clarified by filtration and the product is precipitated from the filtrate by pouring into 600 ml of 0.05 N icecold hydrochloric acid. The precipitate is filtered off and washed with water until neutral. The product, which is homogeneous in a thin layer chromatogram on silica gel ($Rf_{100} = 0.45$) can be recrystallised from methanol-water.

34.
H-Thr(tBu)-Phe-Pro-Gln-Thr(tBu)-Ala-Ile-Gly-OH 3.6 g of the Z-Thr(tBu)-Phe-Pro-Gln-Thr(tBu)-Ala-Ile-Gly-OH obtained under 33) are dissolved in 100 ml of 80 % strength acetic acid and the solution is hydrogenated in the presence of 0.5 g of palladium on charcoal (10 % Pd). After the hydrogen uptake has ended the catalyst is filtered off and the solution is evaporated to dryness. The acetic acid salt of the octapeptide derivative, which is obtained as a colourless firn, is dried in a high vacuum. In a thin layer chromatogram on silica gel, $Rf_{100} = 0.21$.

35.
Z-Asn-Lys(BOC)-Phe-His-Thr(tBu)-Phe-Pro-Gln-Thr(tBu)Ala-Ile-Gly-OH 11.25 g of Z-Asn-Lys(BOC)-Phe-His-hydrazide dissolved in 65 ml of dimethylformamide are mixed at −20°C to −25°C, over the course of 2 minutes, with 8.4 ml of 4.2 N hydrogen chloride in dioxane. Thereafter 2.1 ml of tert.-butyl nitrite are added at −15°C to −20°C and the mixture is allowed to stand for 15 minutes at −15°C. After cooling to −20°C 4.8 ml of triethylamine are added followed by a solution of 9.0 g of the product described under 34) in 210 ml of 90 % strength dimethylformamide. The internal temperature is kept at −15°C by vigorous cooling. The mixture is warmed to 0°C over the course of one hour, with the pH being kept at 7–8 by occasionally adding triethylamine. In total, a further 3.5 ml of triethylamine are added. After stirring overnight at 0°C the mixture is poured into 3 l of ether and the flocculent precipitate is filtered off and twice washed with ether and once with water. The crude product is dissolved in 500 ml of warm methanol and again precipitated by pouring into 1.5 l of 1 % strength acetic acid. The product is filteref off, twice washed with water, and again reprecipitated in the same manner. $RF_{100} = 0.33$ (on silica gel plates).

36.
H-Asn-Lys(BOC)-Phe-His-Thr(tBu)-Phe-Pro-Gln-Thr(tBu)-Ala-Ile-Gly-OH 1.7 g of the above protected dodecapeptide are dissolved in 100 ml of 80 % strength acetic acid and hydrogenated in the usual manner in the presence of 0.5 g of palladium on charcoal (10 % Pd). After filtering off the catalyst, the filtrate is extensively concentrated in a high vacuum at 30°C and the residue is lyophilised with tert.butanol. The product which is obtained in quantitative yield and is homogeneous in a thin layer chromatogram ($Rf_{100} = 0.1$ on silica gel) is immediately processed further.

37.
Z-Thr(tBu)-Tyr(tBU-Thr(tBu)-Gln-Asp(OtBu)-Phe-Asn-Lys-(BOC)-Phe-His-Thr(tBu)-Phe-Pro-Gln-Thr(tBu)-Ala-Ile-Gly-OH 1.73 g of the peptide derivative described under 22) are dissolved in 10 ml of dimethylformamide at 50°C. After cooling to −20°C 0.9 ml of 4.2 N hydrogen chloride in dioxane are added dropwise. 0.22 ml of tert.butyl nitrite are then added at −15°C and the mixture is allowed to react for 15 minutes at −15°C. It is again cooled to −20°C and 0.53 ml of triethylamine are added dropwise followed by a solution of 1.6 g of the peptide derivative described under 36) in 40 ml of 90 % strength dimethylformamide. The temperature is raised at 0°C over the course of one hour, in the course of which the pH is kept at 7–8 by adding triethylamine in portions. In total 0.25 ml of triethylamine are added. After a further 15 hours stirring at 0°C the product is precipitated by pouring into ether and the precipitate is filtered off and washed with ether and water. In order to purify it, it is once reprecipitated from dimethylformamideethyl acetate and once from dimethylformamide-0.02 N hydrochloric acid. The pure material shows $Rf_{100} = 0.40$ in a thin layer chromatogram on silica gel.

38. Z-Ala-Pro-NH$_2$ 2.28 g of H-Pro-NH$_2$ and 7.57 g of Z-Ala-ONP are dissolved in 20 ml of dimethylformamide and the yellow solution is left standing at room temperature for 18 hours. It is then evaporated to dryness in a high vacuum, the residue is mixed with ether and the resulting powder is thoroughly triturated. After filtering off and drying, 5.5 g of Z-Ala-Pro-NH$_2$ of melting point 167.5°–168.5°C are obtained. $[\alpha]_D^{20} = -74°$ (c =1 in methanol).

39. Z-Gly-Ala-Pro-NH$_2$ 27.1 g of the above dipeptide derivative are dissolved in 425 ml of ethanol and after adding 85 ml of 1.0 N aqueous hydrochloric acid are hydrogenated in the presence of 4.25 g of palladium-charcoal (10 % Pd). After completion of the hydrogenation the solution is evaporated at 40°–50°C bath temperature in vacuo. The residue is dissolved in 40 ml of dimethylformamide at 40°C and the solution is cooled to 20°C. 29.1 g of Z-Gly-ONP are then added and after solution 11.2 ml of absolute triethylamine are added dropwise, whilst stirring, over the course of 45 minutes. Thereafter the mixture is stirred for 20 hours at room temperature. The suspension is evaporated at 40°C and 0.01 mm Hg and the residue is partitioned between 600 ml of water and 300 ml of ether. The aqueous layer is twice extracted with 300 ml of ether at a time and the ether layer is twice extracted with 300 ml of water at a time. The aqueous fractions are together evaporated in vacuo at 40°–50°C and repeatedly freed of water by adding chloroform and evaporating. The well-dried residue is taken up in 500 ml of ethyl acetate at 40°–50°C, insoluble triethylamine hydrochloride is filtered off and the filtrate is mixed at 30°–40°C with 10 ml of ether, whereupon crystallisation occurs. After standing for about 20 hours at +5°C to +10°C the crystals are isolated, washed and dried. Melting point: 105°–106°C. The product contains 3 % of triethylamine hydrochloride. It can be further reacted in this form. In order to purify it, 5.0 g of the above crude crystalline material are dissolved in 10 ml of water and after adding 20 ml of methylene chloride are mixed with 15 ml of saturated potassium carbonate solution. The organic layer is separated off, extracted with 10 ml of saturated potassium carbonate solution, and the aqueous layer extracted with 15 ml of methylene chloride. The combined methylene chloride solutions are dried by means of anhydrous sodium sulphate and evaporated. The residue is crystallised from 50 ml of ethyl acetate. 4.4 g of tripeptide derivative of melting point 109°–112°C are obtained. After crystallisation from acetone-methanol-ether (10:4:6) crystals of melting point 144.5°–145.5°C are obtained (crystal polymorphism). $[\alpha]_D^{20} = -93°$ (c = 1.0 in methanol). On thin layer chromatography on silica gel in chloroform + methanol (8:2) Rf = 0.38.

40. H-Gly-Ala-Pro-NH₂Z-Val-Gly-Ala-Pro-NH 18.8 g of the crude tripeptide-amide derivative obtained under 39) are dissolved in 400 ml of dimethylformamide and hydrogenated in the presence of 1.0 g of palladium on charcoal (10 % Pd). After completion of the hydrogenation the mixture is filtered and after brief degassing the solution is employed in the next stage.

41. Z-Val-Gly-Ala-Pro-NH₂

20.1 g of Z-Val-P-nitrophenyl ester are added to the solution of the tripeptide-amide (550 ml) obtained under 40) and the mixture is allowed to stand for 18 hours at room temperature. It is then evaporated to dryness at 50°–60°C and 0.01 mm Hg and the residue is triturated with 300 ml of ether and filtered. The filter residue is dried and stirred in 210 ml of absolute ethanol for 15 minutes at 70°–80°C, cooled to 0°C and filtered. The residue is crystallised from a mixture of 170 ml of absolute tetrahydrofurane, 25 ml of water and 110 ml of ether. Melting point = 209°–211°C. Rf-value on silica gel plates = 0.42 in chloroform-methanol (8:2).

42. H-Val-Gly-Ala-Pro-NH₂

1.1 g of Z-Val-Gly-Ala-Pro-NH₂ are dissolved in 50 ml of 80 % strength methanol and the solution is hydrogenated in the presence of 0.3 g of palladium on charcoal (10 % Pd). When the hydrogen uptake has ended the catalyst is filtered off, the solution evaporated and the residue dried in a high vacuum at 35°C bath temperature. Hereupon the tetrapeptide H-Val-Gly-Ala-Pro-NH₂ is obtained as a colourless substance, Rf-value = 0.20 (silica gel plates, system chloroform-methanol = 1:1).

43. Z-Thr(tBu)-Tyr(tBu)-Thr(tBu)-Gln-Asp(OtBu)-Phe-Asn-Lys-(BOC)-Phe-His-Thr(tBu)-Phe-Pro-Gln-Thr(tBu)-Ala-Ile-Gly-Val-Gly-Ala-Pro-NH₂

800 mg of the peptide derivative described under 37), 500 mg of H-Val-Gly-Ala-Pro-NH₂ and 170 mg of N-hydroxysuccinimide are dissolved in 10 ml of dimethylformamide, concentrated to about one-half in a high vacuum and mixed with 250 mg of dicyclohexylcarbodiimide. After stirring overnight at room temperature the product is precipitated with ether and the material isolated. It is purified by Craig distribution in a mixture of methanol-buffer (as in Example 3, 12)-chloroformcarbo-tetrachloride (10:3:5:6), K = 0.29. The pure product isolated from the distribution shows Rf₁₀₇ = 0.62 in a thin layer chromatogram (on silica gel plates).

44. H-Thr(tBu)-Tyr(tBu)-Thr(tBu)-Gln-Asp(OtBu)-Phe-Asn-Lys-(BOC)-Phe-His-Thr(tBu)-Phe-Pro-Gln-Thr(tBu)-Ala-Ile-Gly-Val-Gly-Ala-Pro-NH₂

300 mg of the above peptide derivative are dissolved in 30 ml of 80 % strength acetic acid and hydrogenated in the presence of 100 mg of palladium on charcoal (10 % Pd). After complete decarbobenzoxylation the catalyst is filtered off, the filtrate extensively concentrated in a high vacuum at 30°C and the residue lyophilised from tert.butanol. The residue is dissolved in 10 ml of methanol, rendered weakly alkaline by adding 1 N sodium bicarbonate and precipitated by adding dropwise to 0.1 N sodium carbonate. The isolated product is again reprecipitated in the same manner. In a thin layer chromatogram on silica gel Rf₁₀₀ = 0.34.

45. BOC-Cys-Gly-Asn-Leu-Ser(tBu)-Thr(tBu)-Cys-Met-LeuGly-Thr(tBu)-Tyr(tBu)-Thr(tBu)-Gln-Asp(OtBu)-PheAsn-Lys(BOC)-Phe-His-Thr(tBu)-Phe-Pro-Gln-Thr(tBu)Ala-Ile-Gly-Val-Gly-Ala-Pro-NH₂

288 mg of the above product, 181 mg of the peptide derivative described under 12) and 46 mg of N-hydroxysuccinimide are dissolved in 2 ml of dimethylformamide at 45°C whilst passing nitrogen over it. After adding 52 mg of dicyclohexylcarbodiimide the mixture is stirred for a further 3 hours at 45°C, then precipitated with peroxide-free ether, and the product isolated. It is purified by a Craig distribution in the system methanol-buffer (as described in Example 3, under 12) -chloroform-carbon-tetrachloride (11:3:6:7); K = 0.74. In a thin layer chromatogram the pure product isolated from the distribution shows Rf₅₂A = 0.4; Rf₁₀₀ = ₀.₃₅ (on silica gel).

EXAMPLE 3

H-Cys-Gly-Asn-Leu-Ser-Thr-Cys-Met-Leu-Gly-Thr-
Tyr-Thr-Gln-Asn-Phe-Asn-Lys-Phe-His-Thr-Phe-Pro-
Gln-Thr-Ala-Ile-Gly-Val-Gly-Ala-Pro-NH$_2$
(Asn$^{15}$-Calcitonine M)

53 mg of very finely powdered BOC-Cys-Gly-Asn-LeuSer(tBu)-Thr(tBu)-Cys-Met-Leu-Gly-Thr(tBu)-Tyr(tBu)-Thr(tBu)Gln-Asn-Phe-Asn-Lys(BOC)-Phe-His-Thr(tBu)-Phe-Pro-Gln-Thr (tBu)-Ala-Ile-Gly-Val-Gly-Ala-Pro-NH$_2$ are dissolved in 2 ml of concentrated hydrochloric acid at 0°C and the solution shaken for 5 minutes. The dissolved hydrogen chloride gas is then expelled under a high vacuum in the course of 5 minutes, the batch is diluted with 4 ml of ice-cold water, and the product converted into the acetic acid salt on a small column of "Amberlite" CG-45 (slightly basic ion exchange resin in acetate form) and the product is lyophilized. The product is a colorless lyophilisate.

UV spectrum in 10% acetic acid $\lambda_{max} = 275$ nm ($\epsilon =$ 1700). In the thin-layer chromatogram on cellulose ("Selecta") Rf$_{45}$ = 0.48, Rf$_{101}$A = 0.49; on alumina ("Alox", Camag) Rf$_{79}$ = 0.57.

On electrophoresis on cellulose ("Selecta") plates at 280 V and at pH 1.9 (acetic acid-formic acid buffer) the substance travels 3.5 cm in the direction of the cathode in the course of an hour and a half.

The starting material can be prepared as follows:

1. Z-Gln-Asn-Phe-OCH$_3$ 14.5 of Z-Gln-ONP and 10.8 g of H-Asn-Phe-OCH$_3$, hydrochloride (Ann. 688, 259 [1965]) are dissolved together in 100 ml of dimethylformamide and to the solution 4.55 ml of triethylamine are added slowly. A thick paste forms which is diluted with 50 ml of dimethylformamide. After a reaction period of 24 hours at room temperature, the batch is filtered and the residue washed with dimethylformamide. The resulting Z-Gln-Asn-Phe-OMe can be recrystallized from much hot dimethylformamide. Melting point, 261°–265°C (decomp.). [$\alpha$]$^{20}_D$ = + 11° (c = 0.94 in hexamethylphosphoric acid triamide).

2. H-Gln-Asn-Phe-OCH$_3$ hydrochloride 14.1 g of Z-Gln-Asn-Phe-OCH$_3$ are hydrogenated at 45°C in 800 ml of methanol with the addition of 8.5 ml of 3N-hydrogen chloride in dioxan and 2.4 g of 10% palladium carbon. When the hydrogen uptake ceases, the batch is filtered and evaporated. The residue is processed without purification.

In the thin-layer chromatogram on silica gel Rf$_{52A}$ = 0.27, Rf$_{45}$ = 0.31; Rf$_{43E}$ = 0.50.

3. Z-Thr(tBu)-Gln-Asn-Phe-OCH$_3$ 9.3 g of H-Gln-Asn-Phe-OCH$_3$ hydrochloride and 11.9 g of Z-Thr(tBu)-OSU are dissolved in 150 ml of dimethylformamide to form a clear solution. 2.85 ml of triethylamine in 10 ml of dimethylformamide are added and the batch is stirred for 21 hours at room temperature. The batch is then concentrated under reduced pressure and taken up in much ethylacetate+λ chloroform (9:1), and extracted with 2 × 200 ml of 5% citric acid and 1 × 100 ml of water. The insoluble precipitate is then filtered off, the filtrate extracted with 2 × 200 ml of 2N-sodium carbonate solution and 3 × 100 ml of water, dried over sodium sulfate, and evaporated. The residue is recrystallized, together with the filter residue mentioned above, from dimethylformamide+ether (1:1). Melting point, 237°–241°C (decomp.); [$\alpha$]$^{20}_D$ = + 8° (c = 1% in dimethylformamide).

In the thin-layer chromatogram on silica gel Rf$_{52}$ = 0.59; Rf$_{102E}$ = 0.59; on alumina ("Alox") Rf$_{43A}$ = 0.59.

4. H-Thr(tBu)-Gln-Asn-Phe-OCH$_3$ 6.31 g of Z-Thr(tBu)-Gln-Asn-Phe-OCH$_3$ and 700 mg of palladium carbon are hydrogenated together at room temperature in 600 ml of methanol in a shaking vessel. The substance gradually passes into solution. The amorphous evaporation residue is used for the next condensation as it is.

In the thin-layer chromatogram on silica gel Rf$_{52}$ = 0.21, Rf$_{102A}$ = 0.21; on alumina Rf$_{43A}$ = 0.19.

5. Z-Tyr(tBu)-Thr(tBu)-Gln-Asn-Phe-OCH$_3$

A solution of 5.9 g of Z-Tyr(tBu)-OH (liberated from 8.8 g of Z-Tyr(tBu)-OH-dicyclohexylammonium salt) in 85 ml of tetrahydrofuran is mixed with 1.84 ml of N-methylmorpholine and caused to react at −33°C with 2.28 ml of chlorocarbonic acid-isobutyl ester. The batch is stirred for half an hour at −20 to −12°C, and then the solution, cooled to −10°C, of the tetrapeptide derivative H-Thr(tBu)-Gln-Asn-Phe-OCH$_3$ in 25 ml of dimethylformamide is run in, the vessel being flushed with 15 ml of aimethylformamide. After a reaction period of 19 hours at room temperature, the batch is concentrated under reduced pressure, suspended in ethyl acetate, and extracted three times with 5% citric acid solution, and 5 times with semi-saturated sodium chloride solution. The suspended residue is filtered off and dried under a high vacuum. The product can be crystallized from methanol. Melting point, 216-219°C; [$\alpha$]$^{20}_D$ = + 4° (c = 1.0 in dimethylformamide).

In the thin layer chromatogram on silica gel Rf$_{52}$ = 0.64; Rf$_{102A}$ = 0.70; on alumina ("Alox"), Rf$_{43A}$ = 0.65; Rf$_{89}$ = 0.17.

6. H-Tyr(tBu)-Thr(tBu)-Gln-Asn-Phe-OCH$_3$ 5.1 g of Z-Tyr(tBu)-Thr(tBu)-Gln-Asn-Phe-OCH$_3$ are decarbobenzoxylated as usual in 600 ml of methanol at room temperature with 800 mg of 10% palladium carbon. In the thin-layer chromatogram on silica gel the resulting H-Tyr(tBu)-Thr(tBu)-Gln-Asn-Phe-OCH$_3$ shows the following Rf values: Rf$_{89}$ = 0.15; Rf$_{102E}$ = 0.28; Rf in chloroform+methanol (9:1) =0.11.

7. Z-Thr(tBu)-Tyr(tBu)-Thr(tBu)-Gln-Asn-Phe-OCH$_3$

The pentapeptide derivative H-Tyr(tBu)-Thr(tBu)-Gln-Asn-Phe-OCH$_3$ is dissolved, together with 4.3 g of Z-Thr(tBu)-OSU, in 40 ml of dimethylformamide and the solution stirred at room temperature for 18 hours. Working up is performed as described under 5. above. The residue which is sparingly soluble in ethyl acetate is recrystallized from methanol. Melting point 206°–208°C; [$\alpha$]$^{20}_D$ = + 15°(c = 1.7% in dimethylformamide); in the thin-layer chromatogram on silica gel Rf$_{102E}$ = 0.69; Rf$_{89}$ = 0.28; Rf in chloroform+methanol (9:1) = 0.30.

8. Z-Thr(tBu)-Tyr(tBu)-Thr(tBu)-Gln-Asn-Phe-NH-NH$_2$ 2.0 g of Z-Thr(tBu)-Tyr(tBu)-Thr(tBu)-Gln-Asn-Phe-OCH$_3$ are dissolved in 150 ml of methanol and caused to react with 10.7 ml of hydrazine hydrate for 6 hours at room temperature. The precipitate is filtered off, washed with methanol, and dried in a high vacuum over concentrated sulfuric acid.

Melting point 231° (decomp); $[\alpha]^{20}_D = +4°$ (c = 0.89 in dimethylformamide).

In the thin-layer chromatogram on silica gel $Rf_{43}C = 0.57$; $Rf_{45} = 0.60$; $Rf_{102E} = 0.58$.

9.

Z-Thr(tBu)-Tyr(tBu)-Thr(tBu)-Gln-Asn-Phe-Asn-Lys(BOC)-Phe-His-Thr(tBu)-Phe-Pro-Gln-Thr(tBu)-Ala-Ile-Gly-OH 800 mg of Z-Thr(tBu)-Tyr(tBu)-Thr(tBu)-Gln-Asn-Phe-NH-NH₂ are dissolved in 18 ml of dimethylformamide, the solution treated at −20°C with 0.58 ml of 3N-hydrogen chloride in dioxan, and the batch then mixed with 0.16 ml of t-butylnitrite. The batch is then stirred for 15 minutes at −20° to −15°C, 0.30 ml of N,N-diisopropyl-ethylamine and 855 mg of H-Asn-Lys(BOC)-Phe-His-Thr(tBu)-Phe-Pro-Gln-Thr(tBu)-Ala-Ile-Gly-OH (acetate) in 20 ml of dimethylformamide (90% strength) are added, followed by stirring at 0°C. After one hour and after another hour, 0.075 ml of N,N-di-isopropylethylamine (a total of 0.15 ml) is added each time, and the batch is stirred at 0°C for 15 hours. The whole is then stirred into 600 ml of ether, the precipitate is allowed to settle, and then filtered. For purification, the crude product is recrystallized once from dimethylformamide+ethyl acetate and once from dimethylformamide+aqueous 0.002N-hydrochloric acid.

In the thin-layer chromatogram on silica gel $Rf_{43E} = 0.62$; $Rf_{100} = 0.32$; $Rf_{45} = 0.53$; $Rf_3 = 0.27$.

10.

Z-Thr(tBu)-Tyr(tBu)-Thr(tBu)-Gln-Asn-Phe-Asn-Lys(BOC)-Phe-His-Thr(tBu)-Phe-Pro-Gln-Thr(tBu)-Ala-Ile-Gly-Val-Gly-Ala-Pro-NH₂

786 mg of Z-Thr(tBu)-Tyr(tBu)-Thr(tBu)-Gln-Asn-Phe-Asn-Lys(BOC)-Phe-His-Thr(tBu)-Phe-Pro-Gln-Thr(tBu)-Ala-Ile-Gly-OH and 251 mg of H-Val-Gly-Ala-Pro-NH₂ are slurried, together with 82 mg of N-hydroxysuccinimide, in 10 ml of dimethylformamide and treated with 90 mg of dicyclohexylcarbodiimide in 1 ml of dimethylformamide at 40°C. The batch is stirred at 40°C for 3 hours before another 65 mg of dicyclohexylcarbodiimide are added, and then stirred for a total of 21 hours at 40°C. The mixture is diluted with 10 ml of methanol, then stirred into 350 ml of ether, the precipitate is allowed to settle, and then filtered off. The precipitate is purified by a Craig distribution in the system methanol+buffer+chloroform+λ carbon tetrachloride (10:3:5:6, buffer as under 18, Example 1).

After 450 stages, the substance which is unitary according to thin-layer chromatography is isolated (K = 0.66).

In the thin-layer chromatogram on silica gel $Rf_3 = 0.40$; $Rf_{45} = 0.42$; $Rf_{100} = 0.32$.

11.

H-Thr(tBu)-Tyr(tBu)-Thr(tBu)-Gln-Asn-Phe-Asn-Lys(BOC)-Phe-His-Thr(tBu)-Phe-Pro-Gln-Thr(tBu)-Ala-Ile-Gly-Val-Gly-Ala-Pro-NH₂

64 mg of Z-Thr(tBu)-Tyr(tBu)-Thr(tBu)-Gln-Asn-Phe-Asn-Lys(BOC)-Phe-His-Thr(tBu)-Phe-Pro-Gln-Thr(tBu)-Ala-Ile-Gly-Val-Gly-Ala-Pro-NH₂ are hydrogenated in a shaking vessel for 15 hours at room temperature in 100 ml of 80% acetic acid in the presence of 16 mg of 10% palladium carbon. The catalyst is filtered off and washed with the same solvent mixture, and this operation is followed by lyophilization. There are obtained 54 mg of the docosapeptide-amide-acetate. This substance is dissolved in 10 ml of warm methanol, the solution adjusted to a pH value of about 7.5 with a few drops of N-sodium bicarbonate solution, and then stirred into 50 ml of an 0.1N-sodium carbonate solution at 0°C.

The milky precipitate is allowed to settle, then filtered off, washed with water and dried.

In the thin-layer chromatogram on silica gel $Rf_{43E} = 0.50$; $Rf_{110} = Rf_{52} = 0.21$.

12.

Boc-C̄ys-Gly-Asn-Leu-Ser(tBu)-C̄ys-Met-Leu-Gly-Thr(tBu)-Tyr(tBu)-Thr(tBu)-Gln-Asn-Phe-Asn-Lys(BOC)-Phe-His-Thr(tBu)-Phe-Pro-Gln-Thr(tBu)-Ala-Ile-Gly-Val-Gly-Ala-Pro-NH₂

93 mg of Boc-C̄ys-Gly-Asn-Leu-Ser(tBu)-Thr(tBu)-C̄ys-Met-Leu-Gly-OH, 95 mg H-Thr(tBu)-Tyr(tBu)-Thr(tBu)-Gln-Asn-Phe-Asn-Lys(BOC)-Phe-His-Thr(tBu)-Phe-Pro-Gln-Thr(tBu)-Ala-Ile-Gly-Val-Ala-Pro-NH₂, 14 mg of N-hydroxysuccinimide and 10 ml of dimethylformamide are stirred under nitrogen with 15 mg of dicyclohexylcarbodiimide. The reaction mixture is stirred at 40°C for a total of 20 hours, another 15 mg of dicyclohexylcarbodiimide being added after the second hour. The batch is then poured into 300 ml of absolute ether, the mixture kept in a refrigerator for 2 hours, the precipitate filtered off with suction, and washed with ether. For purification, the crude product is distributed multiplicatively over 220 stages in the system methanol+buffer+chloroform+carbon tetrachloride (11:3:6:7, buffer as under 18 in Example 1). The pure fractions (vessels 104 – 121; K = 1.0) are combined, evaporated and freed from ammonium acetate under a high vacuum at 40°C.

In the thin-layer chromatogram on silica gel $Rf_{45} = 0.60$; $Rf_{96} = 0.59$; $Rf_{100} = 0.32$.

EXAMPLE 4

Ac-C̄ys-Gly-Asn-Leu-Ser-Thr-C̄ys-Met-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala-Pro-NH₂

(N -acetyl-Calcitonin M)

100 mg of Ac-C̄ys-Gly-Asn-Leu-Ser(tBu)-Thr(tBu)-C̄ys-Met-Leu-Gly-Thr(tBu)-Tyr(tBu)-Gln-Asp(OtBu)-Phe-Asn-Lys(BOC)-Phe-His-Thr(tBu)-Phe-Pro-Gln-Thr(tBu)-Ala-Ile-Gly-Val-Gly-Ala-Pro-NH₂ are taken up in 3 ml of 95% strength trifluoracetic acid at 0°C whilst flushing with nitrogen and after complete solution the mixture is allowed to stand for 90 minutes at room temperature. The product is precipitated with 50 ml of cold ether at 0°C, the suspension is centrifuged and the precipitate is additionally twice triturated with ether. The product, dried over sodium hydroxide in a high vacuum, is, in order to convert it to the acetate form, taken up in 3 ml of water, applied to a column of weakly basic ion exchanger (for example Merck; 7.5 mm; 20 cm) which has been equilibriated with 0.02 N acetic acid, and eluted with 0.02 N acetic acid. The eluate is evaporated in a high vacuum at 25°C and the residue is taken up in water and lyophilised. In order to purify it, the white powder is subjected to a Craig distribution in the system n-butanol-glacial acetic acid-water (4:1:5) (3 ml phase volume). After 600 stages the fractions which according to a thin layer chromatogram contain a homogeneous product as combined, evaporated in a high vacuum at 25°C, and the residue taken up in water and lyophilised. Drying over sodium hydroxide in a high vacuum at room temperature yields an amorphous powder.

In electrophoresis on "Selecta" (at pH 1.9; 1 1/2 hours; 280 V) the product migrates −1.8 cm, at pH 4.8 −1.2 cm. In a thin layer chromatogram "Alox" $Rf_{52}$ = 0.65; $Rf_{79}$ = 0.60; $Rf_{45}$ = 0.72; on "Selecta" $Rf_{45}$ = 0.55; $Rf_{101A}$ = 0.63; $Rf_{52}$=0.38.

The starting material can be manufactured as follows:

1. TRI-Cys(TRI)-Gly-Asn-Leu-OMe 9.1 g of TRI-Cy(TRI)-OH and 3.2 g of H-Gly-Asn-Leu-OMe are dissolved in 60 ml of dimethylformamide and treated, while stirring at 0°C, with 3.7 g of dicyclohexylcarbodiimide. The batch is kept at 0°C for 15 hours and the dicyclohexylurea then filtered off. The filtrate is evaporated to dryness and the residue crystallized from a mixture of chloroform and petroleum ether. Melting point 126°–130°C. In the thin layer chromatogram on silica gel Rf = 0.27 in the system chloroform+methanol (95:5).

2. H-Cys(TRI)-Gly-Asn-Leu-OMe, Acetate 1.8 g of TRI-Cys(TRI)-Gly-Asn-Leu-OMe are dissolved in 16 ml of glacial acetic acid and treated dropwise at room temperature with 4 ml of water. The batch is kept at room temperature for 1 hour, then 12 ml of water are added, the precipitated tritylcarbinol is filtered off, and the filtrate evaporated to dryness in a high vacuum at 40°C. The oily residue is dissolved in tertiary butanol and lyophilized. A white powder is obtained which in the thin-layer chromatogram on silica gel has an Rf value of 0.45 in the system chloroform+methanol (8 : 2).

3. Ac-Cys(TRI)-Gly-Asn-Leu-OMe

At 0°C, 1.9 g of dry dicyclohexylcarbodiimide are added to 1.02 g of H-Cys(TRI)-Gly-Asn-Leu-OMe, acetate, and 0.9 ml of glacial acetic acid in 15 ml of chloroform. After about 10 minutes the reaction mixture has solidified to a magma. It is diluted with 10 ml of chloroform and the mixture is stirred for 4 hours at 0°C. After the addition of 30 ml of petroleum ether the precipitate is filtered off and recrystallized from hot chloroform. Melting point, 156°– 158°C. In the thin-layer chromatogram on silica gel Rf = 0.25 in the system chloroform+methanol (9:1).

4. Ac-Cys(TRI)-Gly-Asn-Leu-NH-NH₂

3.75 mg of hydrazine hydrate are added to 2.42 g of Ac-Cys(TRI)-Gly-Asn-Leu-OMe in 21 ml of dimethylformamide, and the clear solution is allowed to stand at room temperature for 2 hours. The batch is cooled to 0°C, and 150 ml of water are stirred in. The precipitate is filtered off, washed with cold water, and dried over phosphorus pentoxide. For purification it is reprecipitated from hot methanol. $Rf_{53}$= 0.55 in the thin-layer chromatogram on silica gel.

5.
Ac-Cys(TRI)-Gly-Asn-Leu-Ser(tBu)-Thr(tBu)-Cys(-TRI)-Met-Leu-Gly-OH 1.44 g of Ac-Cys(TRI)-Gly-Asn-Leu-NH-NH₂ are dissolved in 10 ml of dimethylformamide and the solution admixed with 2.5 ml of 2.0N-hydrogen chloride in ethyl acetate and 0.26 ml of t-butylnitrite while flushing with nitrogen at −10°C. The batch is allowed to stand at −10°C for 15 minutes, then a solution, cooled to −10°C, of 1.02 g of H-Ser(tBu)-Thr(tBu)-Cys(TRI)-Met-Leu-Gly-OH (acetic acid salt) and 0.84 ml of triethylamine in 12 ml of dimethylformamide are added dropwise in such manner that the temperature does not rise above −10°C. The mixture is stirred for a further hour at −10°C and left to stand at 0°C for 24 hours. The product precipitates as a gel. The reaction mixture is concentrated to about 5 ml, completely precipitated by adding 20 ml of methanol, and the product filtered off and washed with cold dimethylformamide-methanol (1:1). After triturating three times with cold water and drying over sodium hydroxide, the product is reprecipitated once from dimethylformamide-methanol, whereby the sparingly soluble product is obtained in the pure form. Rf = 0.25 in the system chloroform-methanol (8:2) on silica gel.

6.
Ac-C⌐ys-Gly-Asn-Leu-Ser(tBu)-Thr(tBu)-C⌐ys-Met-Leu-Gly-OH

A solution of 410 mg of Ac-Cys(TRI)-Gly-Asn-Leu-Ser(tBu)-Thr(tBu)-Cys(TRI)-Met-Leu-Gly-OH in 35 ml of dimethylformamide is added dropwise at room temperature, over the course of 15 minutes, to a vigorously stirred solution of 1.0 g of iodine in 150 ml of methanol. After completion of the addition the mixture is stirred for a further hour, then cooled to 0°C, and the reaction solution decolorised by dropwise addition of 1.0 N sodium thiosulfate solution. Methanol is first of all evaporated off in a waterpump vacuum at 30°C, and the residue then concentrated to about 10 ml in a high vacuum (30°C) and mixed with 200 ml of ether. The precipitated resin is decanted off, three times triturated with ether and three times with water, and dried over sodium hydroxide in a high vacuum. In order to purify it, the product is dissolved in chloroform, the solution filtered and the product precipitated from the filtrate by means of hexane. $Rf_{70}$ = 0.50; $Rf_{43C}$ = 0.35 on silica gel.

7.
Ac-C⌐ys-Gly-Asn-Leu-Ser(tBu)-Thr(tBu)-C⌐ys-Met-Leu-Gly-Thr(tBu)-Tyr(tBu)-Thr(tBu)-Gln-Asp(Ot-Bu)-Phe-Asn-Lys(BOC)-Phe-His-Thr(tBu)-Phe-Pro-Gln-Thr(tBu)-Ala-Ile-Gly-Val-Gly-Ala-Pro-NH₂

116 mg of Ac-C⌐ys-Gly-Asn-Leu-Ser(tBu)-Thr(tBu)-C⌐ys-Met-Leu-Gly-OH, 250 mg of H-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-Val-Ala-Pro-NH₂ and 16 mg of N-hydroxy-succinimide are dissolved in 2 ml of dimethylformamide, 30 mg of dry dicyclohexylcarbodiimide are added thereto at room temperature and the mixture is allowed to stand for 24 hours at 40°C whilst flushing with nitrogen. The mix is then, without filtering off the dicyclohexylurea, concentrated in a high vacuum to give an oil and this is triturated with methanol-ether (1:1) to give a powder and filtered off. The product is purified by two reprecipitations from methanol-ether. On silica gel is $Rf_{43E}$ = 0.50; $Rf_{52A}$ = 0.30; $Rf_{100}$ = 0.32; $Rf_{107}$ = 0.65.

EXAMPLE 5

Bmp-Gly-Asn-Leu-Ser-Thr-Cys-Met-Leu-Gly-Thr-Tyr-
Thr-Gln-Asp-
Phe-Asn-Lys-Phe-His-Thr-Phe-Pro-Gln-Thr-Ala-Ile-
Gly-Val-Gly-Ala-Pro-NH₂ (Desamino-Calcitonine M)

50 mg of Bmp-Gly-Asn-Leu-Ser(tBu)-Thr(tBu)-Cys-Met-Leu-Gly-Thr(tBu)-Tyr(tBu)-Thr(tBu)-Gln-Asp(OtBu)-Phe-Asn-Lys(BOC)-Phe-His-Thr-(tBu)-Phe-Pro-Gln-Thr(tBu)-Ala-Ile-Gly-Val-Gly-Ala-Pro-NH₂ are mixed at 0°C with 0.95 ml of concentrated hydrochloric acid while flushing with nitrogen. The reaction is allowed to proceed for 5 minutes, then while stirring, the reaction vessel is connected with a high vacuum, and 5 minutes later, 40 ml of tertiary butanol are added, and the batch is lyophilized. A voluminous white powder is obtained. In the thin-layer chromatogram on cellulose, $Rf_{45} = 0.54$, $Rf_{52} = 0.34$, on alumina $Rf_{45} = 0.47$, $Rf_{52} = 0.61$ and $Rf_{79} = 0.66$. In electrophoresis on cellulose "Selecta" 1440 (pH 1.9; 1½ hours, 280 V), the product has a migration distance at pH 4.8 of 1.2 cm towards the cathode.

The starting material can be prepared as follows:

1. Bmp(TRI)-OH 25.1 g of triphenylchloromethane are added in portions at 0°C, while flushing with nitrogen, to a solution of 6.37 g of freshly distilled β-mercapto-propionic acid in 100 ml of benzene. When the introduction is complete the ice cooling is removed. The product begins to precipitate from the initially clear solution. After 2 hours the mixture is cooled to 0°C, filtered and the product washed with cold methanol. Recrystallization from methylene chloride+methanol yields the pure product of melting point 200°–201°C.

2. Bmp(TRI)-Gly-Asn-Leu-OMe 1.85 g of dicyclohexylcarbodiimide are added to a solution, stirred at 0°C, of 2.62 g of Bmp(TRI)-OH and 1.58 g of H-Gly-Asn-Leu-OMe in 30 ml of dimethylformamide. After 24 hours at 0°C the dicyclohexylurea is filtered off and the filtrate evaporated to dryness at 40°C. The product is purified by recrystallization from methanol. In the thin-layer chromatogram on silica gel $Rf_{45} = 0.67$.

3. Bmp(TRI)-Gly-Asn-Leu-NH-NH₂

1.06 of Bmp(TRI)-Gly-Asn-Leu-OMe are mixed with 3 ml of hydrazine hydrate in 30 ml of methanol. After two hours at room temperature the hydrazide crystallizes on inoculation. It is recrystallized from hot methanol. Melting point, 190-194°C. Rf = 0.35 in the system chloroform+methanol (8:2).

4. Bmp(TRI)-Gly-Asn-Leu-Ser(tBu)-Thr(tBu)-Cys(-TRI)-Met-Leu-Gly-OH 926 mg of Bmp(TRI)-Gly-Asn-Leu-NH-NH₂ are mixed in 8 ml of dimethylformamide at −15°C with 2.21 ml of 2.21N-hydrogen chloride in ethyl acetate and 0.18 ml of t-butylnitrite. After 15 minutes at −10°C a solution, cooled to −10°C of 1.38 g of H-Ser(tBu)-Thr(tBu)-Cys(TRI)-Met-Leu-Gly-OH and 0.7 ml of triethylamine in 10 ml of dimethylformamide is added dropwise. Stirring is continued for another hour at −10°C and the mixture then allowed to stand at 0°C for 15 hours. After the addition of 20 ml of methanol, the batch is filtered, the precipitate is washed with cold methanol, then triturated in water, filtered and dried over sodium hydroxide solution. 40% of the product, which is unitary according to thin-layer chromatography, is in the form of the triethylammonium salt. In the thin-layer chromatogram on silica gel Rf = 0.55 in the system chloroform+methanol (7:3).

5. Bmp-Gly-Asn-Leu-Ser(tBu)-Thr(tBu)-Cys-Met-Leu-Gly-OH 0.3 ml of 1.0N-hydrochloric acid is added at room temperature to a solution of 1.4 g. of Bmp(TRI)-Gly-Asn-Leu-Ser(tBu)-Thr(tBu)-Cys(TRI)-Met-Leu-Gly-OH in 150 ml of dimethylformamide. The solution is added dropwise in the course of 30 minutes to a strongly stirred solution of 2.25 g of iodine in 500 ml of methanol. The mixture is stirred for another hour at room temperature, then cooled to 0°C and decolorized by the dropwise addition of 1.0N-aqueous sodium thiosulfate solution. After the addition of 1.6 ml of 0.5N-sodium hydroxide solution, the mixture is concentrated to about 20 ml, 400 ml of ether added, and decanted. The residue is triturated with 20 ml of water, filtered, washed with cold water and dried over caustic soda. The product is purified by reprecipitation from chloroform+ether. In the thin-layer chromatogram on silica gel $Rf_{121A} = 0.43$; $Rf_{100} = 0.34$; $Rf_{43} = 0.28$.

6. Bmp-Gly-Asn-Leu-Ser(tBu)-Thr(tBu)-Cys-Met-Leu-Gly-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-Val-Gly-Ala-Pro-NH₂

46 mg of Bmp-Gly-Asn-Leu-Ser(tBu)-Thr(tBu)-Cys-Met-Leu-Gly-OH, 81 mg of H-Thr(tBu)-Tyr(tBu)-Thr(tBu)-Gln-Asp-(OtBu)-Phe-Asn-Lys(BOC)-Phe-His-Thr(tBu)-Phe-Pro-Gln-Thr(tBu)-Ala-Ile-Gly-Val-Gly-Ala-Pro-HN₂, 9.7 mg of N-hydroxysuccinimide and 13 mg of dicyclohexylcarbodiimide in 2ml of dimethylformamide are maintained at 45°C for 3 hours and a half. The clear solution is then added dropwise to 40 ml of absolute ether at 0°C and the precipitated product is filtered off. The product is purified by reprecipitation from aqueous methanol. $Rf_{45} = 0.38$ in the thin-layer chromatogram on silica gel.

EXAMPLE 6

H-Cys-Gly-Asn-Leu-Ser-Thr-Cys-Met-Leu-Gly-Thr-
Tyr-Thr-Gln-Asp-Phe-Asn-Lys-Phe-His-Thr-Phe-Pro-
Gln-Thr-Ala-Ile-Gly-Val-Gly-Ala-Pro-OH 120 mg of BOC-Cys-Gly-Asn-Leu-Ser(tBu)-Thr(tBu)-Cys-Met-Leu-Gly-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-Val-Gly-Ala-Pro-OtBu together with 3 ml of 95 % strength trifluoracetic acid are stored for 1½ hours under nitrogen at room temperature and then precipitated with peroxide-free ether. The product is filtered off, washed with ether until free of acid, then dissolved in 0.02 N acetic acid, filtered through a column of Merck ion exchanger No. II (weakly basic, acetate form) and the eluate lyophilised. The resulting dotriacontapeptide migrates 3.0 cm towards the cathode in 1½ hours on electrophoresis on "Selecta" at pH 1.9 and 280 V, at pH 4.8–1.5 cm. On "Alox" is $Rf_{79} = 0.45$; $Rf_{52} = 0.42$;

$Rf_{45} = 0.40$; on "Selecta" $Rf_{52} = 0.28$; $Rf_{48} = 0.42$; $Rf_{101A} = 0.50$.

The starting material can be manufactured as follows:

1. H-Pro-OtBu 9.15 g of Z-Pro-OtBu are hydrogenated in 100 ml of methanol and 1.0 g of Pd on charcoal (10 %) at room temperature. The hydrogen uptake has ended after 30 minutes. The solution is freed of catalyst by filtration and evaporated in a waterpump vacuum at 30°C. The resulting oil is homogeneous in a thin layer chromatogram on silica gel. Rf = 0.55 in the system chloroform-methanol (1:1).

2. Z-Ala-Pro-OtBu 10.32 g of Z-Ala-ONP and 5.0 g of H-Pro-OtBu in 10 ml of ethyl acetate are allowed to stand for one hour at 0°C and 15 hours at room temperature. The mixture is then diluted with 100 ml of ethyl acetate, washed with 50 % saturated potassium carbonate solution and water, dried over sodium sulphate and evaporated. The resulting oil is homogeneous according to a thin layer chromatogram on silica gel (Rf = 0.65 in the system chloroform-methanol (9:1)) and is directly used further.

3. H-Ala-Pro-OtBu 9.36 g of Z-Ala-Pro-OtBu are hydrogenated in 100 ml of methanol in the presence of 500 mg of Pd on charcoal (10 %) at room temperature. The hydrogen uptake has ended after 90 minutes. The solution is freed of catalyst by filtration and evaporated in a waterpump vacuum at 30°C to give an oil. This proves to be homogeneous in a thin layer chromatogram on silica gel. Rf = 0.35 in the system chloroform-methanol (1:1).

4. Z-Gly-Ala-Pro-OtBu 1.65 g of Z-Gly-ONP and 1.09 g of H-Ala-Pro-OtBu in 20 ml of ethyl acetate are allowed to stand for 1 hour at 0°C and 20 hours at room temperature. The mix is then diluted with ethyl acetate, washed with 50 % saturated potassium carbonate solution and with water, dried over sodium sulphate and evaporated. 2.06 g of an oil which is homogeneous according to thin layer chromatography result. Rf = 0.8 in the system chloroform-methanol (1:1) on silica gel.

5. H-Gly-Ala-Pro-OtBu 2.06 g of Z-Gly-Ala-Pro-OtBu are hydrogenated in 30 ml of methanol in the presence of 300 mg of Pd on charcoal (10 %) at room temperature. The hydrogen uptake has ended after 90 minutes. The catalyst is filtered off and the filtrate is concentrated to about 5 ml. 10 ml of ether are added. The product crystallises out overnight. Melting point 132°–134°C; Rf = 0.3 in the system chloroform-methanol (1:1) on silica gel.

6. Z-Val-Gly-Ala-Pro-OtBu 3.73 g of Z-Val-ONP and 2.99 g of H-Gly-Ala-Pro-OtBu in 12 ml of ethyl acetate are stirred for one hour at 0°C and 20 hours at room temperature. After dilution with ethyl acetate the mixture is washed with 50 % saturated potassium carbonate solution and water, dried over sodium sulphate and evaporated at 30°C in a waterpump vacuum. The oil is crystallised from methanol-water. Melting point 73°–75°C. In a thin layer chromatogram on silica gel Rf = 0.42 in the system tolueneacetone (1:1) and Rf = 0.46 in the system chloroform-methanol (9:1).

7. H-Val-Gly-Ala-Pro-OtBu 533 mg of Z-Val-Gly-Ala-Pro-OtBu are hydrogenated in 10 ml of methanol in the presence of 300 mg of Pd on charcoal (10%) at room temperature. The hydrogen uptake has ended after 20 minutes. The catalyst is filtered off and the filtrate evaporated in a waterpump vacuum at 30°C to give an oil. Rf = 0.52 in the system chloroform-methanol (1:1) on silica gel.

8. H-Thr(tBu)-Tyr(tBu)-Thr(tBu)-Gln-Asp(OtBu)-Phe-Asn-Lys-(BOC)-Phe-His-Thr(tBu)-Phe-Pro-Gln-Thr(tBu)-Ala-Ile-Gly-OH 270 mg of Z-Thr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-OH are dissolved in 30 ml of 80 % strength acetic acid and hydrogenated in the presence of 50 mg of Pd on charcoal (10%) until the splitting-off of the carbobenzoxy group is complete. After filtering off the catalyst, the solution is extensively concentrated in a high vacuum at 30°C and then lyophilised from t-butanol. The yield is quantitative.

9. BOC-Cys-Gly-Asn-Leu-Ser(tBu)-Thr(tBu)-Cys-Met-Leu-Gly-Thr(tBu)-Tyr(tBu)-Thr(tBu)-Gln-Asp(OtBu)-Phe-Asn-Lys-(BOC)-Phe-His-Thr(tBu)-Phe-Pro-Gln-Thr(tBu)-Ala-Ile-Gly-OH 181 mg of BOC-Cys-Gly-Asn-Leu-Ser(tBu)-Thr(TBU)-Cys-Met-Leu-Gly-OH are dissolved in 1.8 ml of peroxide-free tetrahydrofurane and mixed at −10°C to −15°C with 0.017 ml of N-methylmorpholine and 0.019 ml of chloroformic acid isobutyl ester whilst passing nitrogen over the mixture. After 10 minutes at this temperature, a solution of 255 mg of the octadecapeptide derivative obtained under 8) in 5 ml of 95 % strength dimethylformamide and 0.02 ml of N-methylmorpholine is added. The mixture is stirred for a further 30 minutes at −10°C and 2 hours at 0°C. The crude product is precipitated by adding peroxide-free ether and is again dissolved in dimethylformamide and precipitated by dropwise addition to ice-cold 0.02 N hydrochloric acid. A double reprecipitation from dimethylformamide-ethyl acetate yields a pure product. In a thin layer chromatogram on silica gel $Rf_{52A} = 0.43$.

10. BOC-Cys-Gly-Asn-Leu-Ser(tBu)-Thr(tBu)-Cys-Met-Leu-Gly-Thr(tBu)-Tyr(tBu)-Thr(tBu)-Gln-Asp(OtBu)-Phe-Asn-Lys-(BOC)-Phe-His-Thr(tBu)-Phe-Pro-Gln-Thr(tBu)-Ala-Ile-Gly-Val-Gly-Ala-Pro-OtBu 374 mg of the peptide derivative described under 9), 160 mg of H-Val-Gly-Ala-Pro-OtBu, 46 mg of hydroxysuccinimide and 3 ml of dimethylformamide are mixed with 62 mg of dicyclohexylcarbodiimide under nitrogen at room temperature and allowed to stand overnight at room temperature. The product is precipitated by mixing with ether, filtered off and well washed with ether and ethyl acetate. The product is again dissolved in dimethylformamide and precipitated by dropwise addition to ice-cold 0.05 M citric acid.

EXAMPLE 7

N$^\epsilon$-Acetyl-Calcitonine M

A solution of 100 mg of calcitonine M acetate (or hydrochloride) in 5 ml of water+dimethylformamide (2:1) is treated with 77 µl of a 10% solution of para-nitrophenylacetate in dimethylformamide, and the pH adjusted to 9.1 by the addition of 0.5-molar aqueous triethylamine solution. At this pH the reaction sets in and is completed within about 1 hour by the continuous addition of triethylamine while keeping the pH constant. There are then added 150 µl of glacial acetic acid and the batch is extracted with 3 × 10 ml of ethyl acetate. The aqueous phase is concentrated to dryness and the residue purified by Craig distribution over 170 stages in the system n-butanol/glacial acetic acid/water (4:1:5). From the distribution elements Nos. 109–138 ($r_{max} = 122$; K = 2.5) there is obtained on concentration to dryness pure N$^\epsilon$-acetyl-calcitonine M as an amorphous, water-soluble powder.

In the thin-layer chromatogram on cellulose ("Selecta") $Rf_{101A} = 0.67$; on alumina ("Alox" of Messrs. Camag) $Rf_{52} = 0.68$.

In electrophoresis on cellulose ("Selecta") thin-layer plates, the substance migrates at 17 Volt/cm in an hour and a half at pH 1.9 2.6 cm in the direction of the cathode, and at pH 8.0 0.6 cm towards the anode.

EXAMPLE 8

Mono- and diacetylated calcitonine M

A solution of 10 mg of calcitonine M acetate in 2 ml of absolute dimethylformamide is treated with 0.5 ml of a 1% solution of para-nitrophenylacetate in dimethylformamide, rinsed with nitrogen, and allowed to stand in the closed test tube at 40°C for 30 minutes. 5 ml of 2N-acetic acid are then added, the excess para-nitrophenyl acetate and the para-nitrophenol formed are extracted with ethyl acetate (2 × 30 ml), the aqueous phase is evaporated to dryness under reduced pressure, the residue dissolved in 0.5 ml of 95% acetic acid, and the solution lyophilized. The product consists of a mixture of mono- and diacetyl derivative and some starting material. The monoacetyl derivative itself is a mixture of the N$^\alpha$- and N$^\epsilon$-derivatives as evidenced by electrophoresis at pH 8.

The separation of starting material, mono- and diacetyl compound is performed by Craig distribution in the system n-butanol/glacial acetic acid/water (4:1:5), or by preparative thin-layer electrophoresis on cellulose ("Selecta") plates at pH 1.9 (1½ hours at 17 Volt/cm); for migration distances, see below. The mixture of the two mono-acetyl derivatives obtained in this manner is in turn resolved by preparative thin-layer electrophoresis at pH 8 (buffer: 0.1-molar triethylamine solution adjusted to pH 8 with carbon dioxide; 3 hours at 17 Volt/cm). For larger quantities of substance, the continuous, carrier-free electrophoresis is employed, likewise at pH 8. In either case, N$^\alpha$-acetyl-calcitonine M shows a neutral behavior, electrically, whereas the N$^\epsilon$-acetyl derivative migrates to the anode.

The compounds have the following Rf values: N$^\alpha$-acetyl-calcitonine M on cellulose ("Selecta"): $Rf_{101A} = 0.67$; on alumina ("Alox" of Messrs. Camag): $Rf_{52} = 0.68$. N$^\epsilon$-acetyl-calcitonine has in both systems the same Rf values as N$^\alpha$-acetyl-calcitonine M (calcitonine M has in these systems $Rf_{101A} = 0.56$ and $Rf_{52} = 0.62$); N$^\alpha$,N$^\epsilon$-diacetyl-calcitonine M has the following Rf values in these two systems: $Rf_{101A} = 0.75$ and $Rf_{52} = 0.73$. In electrophoresis on cellulose ("Selecta") thin-layer plates, the migration distance of both N$^\alpha$- and N$^\epsilon$-monoacetyl-calcitonine M = −2.6 cm at pH 1.9; 90 minutes; 17 Volt/cm; and that of N$^\alpha$,N$^\epsilon$-diacetyl-calcitonine M under the same conditions is −1.3 cm (that of calcitonine M is −3.7 cm). At pH 8.0 N$^\epsilon$-acetyl-calcitonine M migrates in 90 minutes at 17 Volt/cm + 0.6 cm, whereas N$^\alpha$-acetyl-calcitonine M (as also calcitonine M) remains in place.

EXAMPLE 9

The starting material
BOC-Cys-Gly-Asn-Leu-Ser-Thr-Cys-Met-Leu-Gly-OH
described in Example 1 can also be manufactured as follows:

1. BOC-Ser-Thr-OBzl 47.0 g of H-Thr-OBzl. HCl in 300 ml of methylene chloride are added to a solution of 73.8 g of BOC-Ser-OH. Dicyclohexylammonium salt in 500 ml of methylene chloride and the mixture stirred for 10 minutes at room temperature and then cooled to −5°C. A solution of 40.1 g of dicyclohexylcarbodiimide in 90 ml of methylene chloride is added dropwise at this temperature. The mixture is stirred for 3 hours at −5°C and overnight at room temperature. After filtering off the dicyclohexylurea and dicyclohexylamine hydrochloride the solution is extracted by shaking three times with 0.1 N hydrochloric acid, twice with 20 % strength sodium chloride solution, once with 10 % strength sodium bicarbonate solution and twice with 20 % strength sodium chloride solution and is dried over sodium sulphate. The solution is concentrated to about 600 ml, cooled to 5°C and further dicyclohexylurea is filtered off. After evaporation to dryness, the residue is crystallised from ethyl acetate-hexane in order to purify it.

Melting point 110–111°C; $[\alpha]_D = -8.5°$ (c = 2 in dimethylformamide); $Rf_2 = 0.33$ (on silica gel).

2. H-Ser-Thr-OBzl. TFA 65.7 g of BOC-Ser-Thr-OBzl are dissolved in 100 ml of 90 % strength trifluoracetic acid and the solution is left for 1 hour at 20°C. It is then added dropwise to 1000 ml of dry ether whilst stirring and the mixture is stirred for one hour and left to stand overnight at −10°C. The resulting precipitate is filtered off and washed 3 times with dry ether and dried in vacuo over sodium hydroxide; melting point 128°–129°C; $Rf_7 = 0.65$; $Rf_4 = 0.50$ (on silica gel).

3. BOC-Leu-Ser-Thr-OBzl 52.5 g of H-Ser-Thr-OBzl. TFA are dissolved in 145 ml of dimethylformamide and mixed at 0°C with a solution of 48.0 g of BOC-Leu-ONP. 21 ml of triethylamine and 0.75 ml of glacial acetic acid are then added. The reaction mixture is stirred for 3 hours at 0°C and overnight at room temperature. After adding 2.1 liters of ethyl acetate the solution is extracted by shaking twice with water, twice with 0.1 N hydrochloric acid, twice with 10 % strength sodium chloride solution, eight times with 20 % strength potassium carbonate solution, twice with 10 % strength sodium chloride solution and once with 30 % strength sodium chloride solution. After drying over sodium sulphate the solution is concentrated to about 1.4 liters. The protected tripeptide of melting point 114°–116°C crystallises overnight in the refrigerator; $[\alpha]_D = -14°$ (c = 2 in dimethylformamide); $Rf_2 = 0.25$ (on silica gel).

4. H-Leu-Ser-Thr-OBzl. TFA 46.1 g of BOC-Leu-Ser-Thr-OBzl are dissolved in 92.5 ml of 90 % strength trifluoracetic acid and left for 1 hour at 20°C. Thereafter dry ether (925 ml) is added whilst stirring, and the mixture is stirred for 1 hour at 0°C and left to stand overnight at −10°C. The resulting precipitate is filtered off, washed three times with dry ether and dried in vacuo over sodium hydroxide. Melting point 168°–171°C; $Rf_7 = 0.80$ (on silica gel).

5. BOC-Asn-Leu-Ser-Thr-OBzl 20.8 g of BOC-Asn-OH are suspended in 208 ml of acetonitrile, mixed with 22.7 g of Woodward's Reagent K and the mixture stirred for 30 minutes at 20°C. 12.6 ml of triethylamine are then added dropwise, whilst stirring, in such a way that the internal temperature does not exceed +32°C, and the mixture is cooled to 20°C and stirred for a further 50 minutes at this temperature. The almost clear solution is cooled to 0°C and is mixed with a solution, also cooled to 0°C, of 39.1 g of H-Leu-Ser-Thr-OBzl.TFA and 10.5 ml of triethylamine in 257 ml of dimethylformamide. The reaction mixture, which soon solidifies, is stirred overnight at room temperature, cooled to −10°C and stirred for a further 2 hours at −10°C. Thereafter the crystalline precipitate is filtered off and the tetrapeptide derivative is washed once with cold acetonitrile, once with ethyl acetate and three times with water it is free of chloride. The resulting product is crystallised from 370 ml of dimethylformamide, 3.7 ml of glacial acetic acid and 370 ml of acetonitrile. Melting point 225–226°C; $[\alpha]_D = -36°$ c = 2 in dimethylformamide); $Rf_6 = 0.85$ (on silica gel).

6. H-Asn-Leu-Ser-Thr-OBzl. TFA 32 g of BOC-Asn-Leu-Ser-Thr-OBzl are dissolved in 192 ml of 90 % strength trifluoracetic acid and the solution left for 45 minutes at 20°C. Thereafter the solution is concentrated to about 40 ml, mixed with 400 ml of ether whilst stirring and stirred for 20 minutes at 35°C under reflux. The crystal suspension is then cooled to −10°C and is left to stand overnight at −10°C. The precipitate is filtered off, washed three times with ether and dried in vacuo over sodium hydroxide. Melting point 125°–127°C; $Rf_4 = 0.33$ (on silica gel).

7. BOC-Gly-Asn-Leu-Ser-Thr-OBzl 26.3 g of H-Asn-Leu-Ser-Thr-OBzl.TFA are dissolved in 100 ml of dimethylformamide, the solution is cooled to 0°C and successively mixed with 7.5 ml of triethylamine, 0.54 ml of glacial acetic acid and a solution of 14.4 g of BOC-Gly-ONP in 100 ml of dimethylformamide, stirred at room temperature until the mixture solidifies and left to stand for 2 days. Thereafter 300 ml of ethyl acetate are added whilst stirring and the mixture left to stand overnight at −10°C. The precipitate is filtered off, washed twice with ethyl acetate and twice with ether, stirred for half an hour with 200 ml of water, filtered off, washed with water and dried in vacuo. Melting point 227–228°C; $[\alpha]_D = -23°$ (c = 2 in dimethylformamide); $Rf_9 = 0.50$ (on silica gel).

8. BOC-Gly-Asn-Leu-Ser-Thr-OH 17.0 g of BOC-Gly-Asn-Leu-Ser-Thr-OBzl are dissolved in 340 ml of dimethylformamide whilst warming. After cooling to room temperature, 3.4 g of 10 % strength palladium on charcoal are added and the product is hydrogenated. The reduction is complete after 4 hours. After filtering off the catalyst the solution is concentrated in a high vacuum. Triturating three times with ether yields a pentapeptide which is homogeneous according to a thin layer chromatogram. Melting point 181°–183°C; $[\alpha]_D = -16.5°$ (c = 2 in dimethylformamide); $Rf_7 = 0.65$ (on silica gel).

9. BOC-Gly-Asn-Leu-Ser-Thr-Cys(Bzl)-$N_2H_2$-Z 9.2 g of H-Cys(Bzl)-$N_2H_2$-Z.HCl are dissolved in 300 ml of freshly distilled dimethylformamide, mixed with 12.2 g of BOC-Gly-Asn-Leu-Ser-Thr-OH and stirred at room temperature until solution has occurred. The solution is then cooled to 0°C, 3.28 ml of triethylamine and 4.88 g of N-hydroxysuccinimide in 100 ml of dimethylformamide are added, the mixture is further cooled to −22°C and 4.36 g of dicyclohexylcarbodiimide in 30 ml of dimethylformamide are added. The mixture is stirred for 1 hour at −22°C, the internal temperature is then allowed to rise gradually, the mixture stirred for a further 3 days at room temperature, the precipitated dicyclohexylurea filtered off and the filtrate evaporated to dryness in a high vacuum. The residue is stirred with a mixture of ethyl acetate and 5 % strength citric acid solution and the precipitate is filtered off, washed with water, dried in vacuo, stirred with dry ether, filtered and dried in a high vacuum. Melting point 173°–178°C; $[\alpha]_D = -25.5°$ (c = 2 in dimethylformamide); $Rf_1 = 0.21$ (on silica gel).

10. H-Gly-Asn-Leu-Ser-Thr-Cys(Bzl)-$N_2H_2$-Z.TFA 13 g of BOC-Gly-Asn-Leu-Ser-Thr-Cys(Bzl)-$N_2H_2$-Z are dissolved in 130 ml of 90 % strength trifluoracetic acid and the solution is left to stand for 2 hours at 22°C. It is then concentrated and the residue stirred 3 times with ether and dried in vacuo over sodium hydroxide. Melting point 159°–161°C. $Rf_6 = 0.63$ (on silica gel).

11. BOC-Cys(Bzl)-Gly-Asn-Leu-Ser-Thr-Cys(Bzl)-$N_2H_2$-Z 6.69 g of BOC-Cys(Bzl)-OSU and 12.2 g of H-Gly-Asn-Leu-Ser-Thr-Cys(Bzl)-$N_2H_2$-Z. 1.22 TFA are dissolved in 100 ml of dimethylformamide. Triethylamine is added dropwise from a solution of 150 mMols of triethylamine in 100 ml of dimethylformamide, whilst stirring, until the reaction mixture shows a pH value of 6.4 on moist indicator paper. The solution is stirred for 3 days at room temperature and thereafter evaporated to dryness in a high vacuum. The residue is twice stirred with 300 ml of ethyl acetate thereafter stirred three times with a mixture of 150 ml of ethyl acetate and 30 ml of 5 % strength citric acid solution, filtered off, dried in vacuo and crystallised from dimethylformamide-ethyl acetate. Melting point 191–193°C; $[\alpha]_D = -31.5°$ (c = 2 in dimethylformamide); $Rf_8 = 0.35$ (on silica gel).

12. BOC-Cys-Gly-Asn-Leu-Ser-Thr-Cys-$N_2H_3$ 6 g of BOC-Cys(Bzl)-Gly-Asn-Leu-Ser-Thr-Cys(Bzl)-$N_2H_2$-Z are dissolved at −40°C in 700 ml of dry liquid ammonia. 973 mg of sodium are added at the boiling point of the ammonia, whilst stirring, in such a way that the colour of the reaction mixture only becomes light blue. After 25 minutes the reduction is complete. The mixture is stirred for a further 10 minutes with the blue colouration being retained, 2.4 ml of glacial acetic acid are then added and the mixture evaporated to dryness in a high vacuum (about 1 mm). The residue is stirred with 12 ml of water, 3.2 ml of glacial acetic acid and 20 ml of ethyl acetate for 1 hour at 0°C and the precipitate is filtered off, twice washed with 10 ml of 1 % strength acetic acid solution and once with 10 ml of ethyl acetate and dried in a high vacuum. $Rf_5 = 0.65$ (on silica gel).

13. BOC-Cys-Gly-Asn-Leu-Ser-Thr-Cys-N₂H₃

1.0 g of BOC-Cys-Gly-Asn-Leu-Ser-Thr-Cys-N₂H₃ is dissolved in 100 ml of dimethylformamide and 500 ml of water containing 1.23 milliequivalent of hydrogen chloride. The pH-value of the solution is adjusted to 6.8 by means of 3.7 ml of an 0.43 N potassium hydroxide solution. 247 ml of an 0.01 M potassium ferricyanide solution and 4.9 ml of an 0.43 N potassium hydroxide solution are simultaneously added dropwise with stirring over the course of 90 minutes whilst maintaining this pH-value. The mixture is stirred for a further 90 minutes at room temperature and the pH-value of the solution is then brought to 4.0 by means of 0.7 ml of glacial acetic acid. The solution is thereafter stirred with 50 ml of Dowex-2-X8, acetate form and subsequently with 13 ml of Dowex-50W-X8, H⁺ form, the mixture filtered and the filtrate evaporated to dryness. The residue is dissolved in 50 % strength t-butanol, lyophilised and dried in a high vacuum. The product contains about 15 % of potassium acetate. It is homogeneous in a thin layer chromatogram on silica gel: $Rf_5 = 0.63$; $Rf_6 = 0.70$; $Rf_7 = 0.75$.

14. H-Leu-Gly-OEt.HCl 14 g of Z-Leu-Gly-OEt [manufactured according to J. R. Vaughan & R. L. Osato, J.Am.Chem.Soc. 73, 5553 (1951)] are dissolved in 150 ml of absolute ethanol, mixed with 11.5 ml of a 6.9 N hydrogen chloride solution in ethanol and hydrogenated in the presence of 2.8 g of palladium on charcoal (10 % Pd). After 1 hour the catalyst is filtered off and the filtrate evaporated in vacuo at 40°C bath temperature. The residue is an oil and is directly processed further. $Rf_1 = 0.50$ (on silica gel).

15. BOC-Met-Leu-Gly-OEt 10.5 g of BOC-Met-N₂H₃ in 100 ml of dimethylformamide are mixed at 0°C with 14.8 ml of hydrogen chloride in tetrahydrofurane (5.39 N; 80 mMols) and subsequently at −20°C with 5.4 ml of iso-amylnitrite. After 5 minutes at −20°C a pre-cooled solution of 10.1 g of H-Leu-Gly-OEt.HCl and 16.9 ml of triethylamine in 100 ml of dimethylformamide is added. The reaction mixture is left for 3 days at 0°C. The triethylamine hydrochloride which has separated out is then filtered off and the filtrate evaporated to dryness in a high vacuum. The residue is dissolved in ethyl acetate and the solution is successively washed with 3 portions of dilute citric acid solution, 3 portions of dilute sodium bicarbonate solution and with water. The crude product obtained after drying and evaporating the solution is crystallised from ethyl acetatehexane.

Melting point 118°–119°C; $[\alpha]_D = -30°$ (c = 2 in dimethylformamide); $Rf_1 = 0.72$ (on silica gel).

16. BOC-Met-Leu-Gly-OH 9.98 g of BOC-Met-Leu-Gly-OEt are dissolved in 300 ml of methanol. 57 ml of 0.59 N sodium hydroxide solution are added over the course of 45 minutes at room temperature and the mixture is stirred for a further hour. Thereafter the pH-value is adjusted to 7 with 0.68 N hydrochloric acid and the solution is evaporated to dryness. The residue is dissolved in ethyl acetate and water and the pH-value is brought to 2 by means of 0.68 N hydrochloric acid. The aqueous phase is extracted by shaking with ethyl acetate. The combined ethyl acetate phases are washed with sodium chloride solution, dried and evaporated. The residue is crystallised from ethyl acetate-hexane.

Melting point 137°–138°C; $[\alpha]_D = -31°$ (c = 2 in dimethylformamide); $Rf_7 = 0.74$ (on silica gel).

17. H-Met-Leu-Gly-OH 6.9 g of BOC-Met-Leu-Gly-OH are dissolved in 70 ml of 90 % strength trifluoracetic acid and left to stand for one hour at 20°C. Thereafter the solution is concentrated, mixed with 150 ml of ether whilst stirring and left to stand overnight at −10°C. The resulting precipitate is filtered off and again stirred with 100 ml of ether, filtered off, twice washed with ether and dried in vacuo over sodium hydroxide. Melting point 134°–135°C; $Rf_7 = 0.52$ (on silica gel).

18. BOC-Cys-Gly-Asn-Leu-Ser-Thr-Cys-Met-Leu-Gly-Oh 800 mg. of BOC-Cys-Gly-Asn-Leu-Ser-Thr-Cys-N₂H₃ [containing 15 % of potassium acetate] are suspended in 15 ml of dimethylformamide and stirred for 15 minutes at 45°C; a part of the suspension dissolves. The mixture is now cooled to 0°C and 1.45 ml of hydrogen chloride in tetrahydrofurane (2.0 N) are first added, the mixture further cooled to −20°C and 0.114 ml of iso-amyl-nitrite then added. After 10 minutes at −20°C 0.24 ml of triethylamine are added followed by a pre-cooled solution of 431 mg of H-Met-Leu-Gly-OH. 0.57 TFA in 5 ml of dimethylformamide. Triethylamine is added dropwise from a dilute triethylamine solution in dimethylformamide until the reaction mixture shows a pH-value of 6 on moist indicator paper. The cloudy solution is left for 3 days at 0°C and the resulting precipitate is then filtered off. The filtrate is evaporated to dryness in a high vacuum; the residue is stirred three times with 10 % strength citric acid solution and the resulting product is filtered off and dried in a high vacuum. $Rf_6 = 0.68$; $Rf_7 = 0.75$ (on silica gel).

EXAMPLE 10

Nα-Palmitoyl-Cys-Gly-Asn-Leu-Ser-Thr-Cys-Met-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala-Pro-NH₂ (Nα-Palmitoyl-Calcitonine M).

171 mg of Nα Palmitoyl-Cys-Gly-Asn-Leu-Ser-(tBU) - Cys - Met - Leu - Gly - Thr(tBU)- -Tyr - (tBu) - Gln - Aps(OtBu) - Phe - Asn - Lyst(BOC) - Phe - His - Thr(tBu)-Phe - Pro - Gln - Thr(tBu) - Ala-Ile - Gly - Val - Gly - Ala - Pro - NH₂ are admixed with 5 ml of ice-cold concentrated hydrochloric acid, the mixture is stirred at 0°C until dissolution occurs (about 2 minutes), and the solution then allowed to stand at 0°C under nitrogen for another 8 minutes. The batch is then freed from the gaseous, dissolved hydrogen chloride by evacuation for 1 minute under a pressure of 0.01 mm Hg; 100 ml of t-butanol are added and the batch is lyophilized. There are obtained in this manner 138 mg of the hydrochloric acid salt of Nα-palmitoyl-calcitonine M as a colorless powder. In the thin-layer chromatography on alumina ("Alox") the product shows these values: $Rf_{45} = 0.52$, $Rf_{52} = 0.76$. In the test according to Kumar, the product has a markedly longer action than calcitonine M.

The protected $N^\alpha$-palmitoyl-dotriacontapeptide amide used as starting material can be prepared as follows:

1. Palmitic acid-para-nitrophenylester (Pal-ONP = hexadecanoic acid-para-nitrophenylester)

To 5.0 g of para-nitrophenol in 60 ml of chloroform+ether (1:1) are added while cooling with ice first 9.4 g of palmitoyl chloride and then 5.0 ml of triethylamine. After having been refluxed for 2 hours, the batch is dissolved in ethyl acetate, and the organic phase is washed with 0.5N-potassium carbonate and water, dried over sodium sulfate and evaporated. On crystallization from ether+petroleum ether, lamellae are obtained which melt at 64°–65°C.

2. Pal-Cys(TRI)-Gly-Asn-Leu-OMe 1.32 g of H-Cys(TRI)-Gly-Asn-Leu-OMe and 780 mg of palmitic acid-para-nitrophenylester are dissolved in 20 ml of freshly distilled dimethylformamide and allowed to stand at room temperature for 24 hours. From the crude product obtained on evaporation of the solvent, the compound is obtained in the thin-layer chromatographically pure form on recrystallization from methanol.

3. Pal-Cys(TRI)-Gly-Asn-Leu-NH-NH$_2$ 4.0 ml of hydrazine hydrate are added to 1.35 g of Pal-Cys(TRI)-Gly-Asn-Leu-OMe in 40 ml of methanol and the solution maintained at room temperature for 24 hours. It is then evaporated to a volume of about 20 ml in a rotary evaporator at 25°C, and 150 ml of 0.5N-acetic acid are added. The product which precipitates is filtered off, washed with cold water, and dried over caustic soda. In the thin-layer chromatogram on silica gel the product has this value: $Rf_{100} = 0.45$.

4.
Pal-Cys(TRI)-Gly-Asn-Leu-Ser(tBu)-Thr(tBu)-Cys(-TRI)-Met-Leu-Gly-OH 1.08 g of Pal-Cys(TRI)-Gly-Asn-Leu-NH-NH$_2$ in 10 ml of dimethylformamide are treated at −15°C with 1.5 ml of 2.0N-hydrogen chloride in ethyl acetate and 0.17 ml of t-butylnitrite. The batch is allowed to stand at −10°C for 15 minutes, after which a solution, cooled to −10°C of 980 mg of H-Ser(tBu)-Thr(tBu)-Cys(TRI)-Met-Leu-Gly-OH and 0.56 ml of triethylamine in 10 ml of dimethylformamide are added dropwise. The batch is allowed to stand at −10°C for an hour and at 0°C for 15 hours before 30 ml of methanol are added, and the product that precipitates is then filtered off, washed with cold methanol and dried in a high vacuum at 40°C. The resulting powder is triturated with 3 × 10 ml of water and then dried over caustic soda. Reprecipitation from dimethylformamide+methanol gives a product which is pure according to thin-layer chromatography.

5.
Pal-Cys-Gly-Asn-Leu-Ser(tBu)-Thr(tBu)-Cys-Met-Leu-Gly-OH

A solution of 670 mg of Pal-Cys(TRI)-Gly-Asn-Leu-Ser(tBu)-Thr(tBu)-Cys(TRI)-Met-Leu-Gly-OH in 50 ml of dimethylformamide is added dropwise in the course of 20 minutes to a vigorously stirred solution of 1.0 g of iodine in 150 ml of methanol. The batch is stirred for another hour and then decolorized at 0°C by the dropwise addition of 1N-aqueous sodiumthiosulfate. The clear solution is concentrated to about 10 ml first under a water-jet vacuum, then under a high vacuum at 30°C, treated with 200 ml of ether+petroleum ether (1:1), and decanted. The residue is briefly dried under a water-jet vacuum, then triturated with 3 × 10 ml of water, and dried over caustic soda. For purification the product is recrystallized from chloroform+petroleum ether. In the thin-layer chromatogram $Rf_{53} = 0.50$.

6.
$N^\alpha$-Pal-Cys-Gly-Asn-Leu-Ser(tBu)-Thr(tBu)-Cys-Met-Leu-Gly-Thr(tBu)-Tyr(tBu)Thr(tBu)-Gln-Asp(OtBu)-Phe-Asn-Lys(BOC)-Phe-His-Thr(tBu)-Phe-Pro-Gln-Thr(tBu)-Ala-Ile-Gly-Val-Gly-Ala-Pro-NH$_2$ To a solution of 418 mg of $N^\alpha$-Pal-Cys-Gly-Asn-Leu-Ser(tBu)-Thr(tBu)-Cys-Met-Leu-Gly-OH and 290 mg of the protected docosapeptide amide described under 44 in Example 2 and 110 mg of N-hydroxysuccinimide in 15 ml of freshly distilled dimethylformamide are added while stirring and heating to 45°C 135 mg of dicyclohexylcarbodiimide. The mixture is stirred under nitrogen for another 3 hours at 45°C, and another 70 mg of N-hydroxysuccinimide and dicyclohexylcarbodiimide are then added, and stirring is continued for another 4.5 hours at 45°C. The batch is then cooled to 0°C and poured into 300 ml of ice-cold, peroxide-free ether. After 12 hours at 0°C the precipitate is filtered off with suction, washed with ether and dried in vacuo at 40°C. For purification, the product is dissolved in methanol+chloroform (1:1) and chromatographed in this solvent mixture upwards through a column of "Sephadex" LH$_{20}$ measuring 110 × 4.2 cm. Fractions of 3 ml are collected and examined by thin-layer chromatography. In the thin-layer chromatogram on silica gel plates $Rf_{52A} = 0.62$.

EXAMPLE 11

$N^\alpha$-Lauroyl-Cys-Gly-Asn-Leu-Ser-Thr-Cys-Met-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala-Pro-NH$_2$
($N^\alpha$-Lauroyl-Calcitonine M)

7 mg of $N^\alpha$-Lauroyl-Cys-Gly-Asn-Leu-Ser(tBu)-Thr(tBu)-Cys-Met-Leu-Gly-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-Val-Gly-Ala-Pro-NH$_2$ are stirred into 0.42 ml of ice-cold, analytically pure, concentrated hydrochloric acid and stirred under nitrogen at 0°C for 10 minutes. For removal of the gaseous, dissolved hydrogen chloride, the mixture is kept at 0°C under a pressure of 0.01 mm of Hg for 1 minute, then 6 ml of t-butanol are added, and the mixture is lyophilized. 5 mg of the monohydrochloride of $N^\alpha$-lauroyl-calcitonine M are obtained.

In the test arrangement of Kumar et al (J. Endocrinology, 33, 469 [1965]) the product has a longer action than calcitonine.

The starting material can be prepared as follows:

1. Lauric acid-para-nitrophenylester, (Lau-CNP = dodecanoic acid-para-nitrophenylester)

The compound is prepared from 5.0 g of para-nitrophenol and 7.2 g of lauryl chloride by the process described in Example 10 for palmitic acid-para-nitrophenyl ester.

2. Lau-Cys(TRI)-Gly-Asn-Leu-OMe 1.5 g of lauric acid-para-nitrophenylester and 1.65 g of H-Cys(TRI)-Gly-Asn-Leu-OMe in 25 ml of dimethylformamide are allowed to stand at room temperature for 24 hours. Evaporation of the solvent and reprecipitation from methanol yields the product which is unitary according to thin-layer chromatography. $Rf_{53} = 0.60$ on silica gel.

3. Lau-Cys(TRI)-Gly-Asn-Leu-NH-NH$_2$ 1.0 g of Lau-Cys(TRI-Gly-Asn-Leu-Ome are reacted at room temperature for 24 hours in 40 ml of methanol and 4 ml of hydrazine hydrate to form the hydrazide. Isolation is achieved by concentrating the solution and precipitation with 0.5N-acetic acid. $Rf_{100} = 0.40$ on silica gel.

4. Lau-Cys(TRI)-Gly-Asn-Leu-Ser(tBu)-Thr(tBu)-Cys(TRI)-Met-Leu-Gly-OH

A solution of 1.42 g of Lau-Cys(TRI)-Gly-Asn-Leu-NH-NH$_2$ in 10 ml of dimethylformamide is treated at −15°C with 1.38 ml of 2N-hydrogen chloride in ethyl acetate and 0.14 ml of t-butylnitrite. The batch is allowed to stand at −10°C for 15 minutes before a solution, cooled to −10°C, of 965 mg of H-Ser(tBu)-Thr(tBu)-Cys(TRI)-Met-Leu-Gly-OH and 0.525 ml of triethylamine in 10 ml of dimethylformamide is added, and the mixture is then allowed to stand at −10°C for 1 hour and at 0°C for 15 hours. The product which separates out of the reaction solution as a gel is completely precipitated by the addition of 20 ml of methanol, then filtered and triturated with 3 × 10 ml of water, and dried over caustic soda. For purification it is reprecipitated from hot methanol.

5. Lau-C̅y̅s̅-̅G̅l̅y̅-̅A̅s̅n̅-̅L̅e̅u̅-̅S̅e̅r̅(̅t̅B̅u̅)̅-̅T̅h̅r̅(̅t̅B̅u̅)̅-̅C̅y̅s̅-Met-Leu-Gly-OH 700 mg of Lau-Cys(TRI)-Gly-Asn-Leu-Ser(tBu)-Thr(tBu)-Cys(TRI)-Met-Leu-Gly-OH in 50 ml of dimethylformamide are added dropwise in the course of 20 minutes while stirring to a solution of 1.0 g of iodine in 150 ml of methanol at room temperature. For elimination of the excess oxidant 1N-thiosulfate solution is added dropwise at 0°C and the mixture then concentrated to about 10 ml under a water-jet vacuum and then under a high vacuum. By the addition of 200 ml of ether+ petroleum ether (1:1) the product is precipitated. The precipitate is dried and triturated three times with water, dried over caustic soda, and reprecipitated from chloroform+ petroleum ether for purification.

6. N$^\alpha$-Lauroyl-C̅y̅s̅-Gly-Asn-Leu-Ser(tBu)-Thr(tBu)-C̅y̅s̅-Met-Leu-Gly-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-Val-Gly-Ala-Pro-NH$_2$ A mixture of 35 mg of the protected docosapeptide amide described under 44 in Example 2, 24 mg of N$^\alpha$-lauroyl-C̅y̅s̅-Gly-Asn-Leu-Ser(tBu)-Thr(tBu)-C̅y̅s̅-Met-Leu-Gly-OH, 6 mg of N-hydroxysuccinimide and 0.8 ml of dimethylformamide is stirred at 50°C under nitrogen for 1 hour. 6 mg of dicyclohexylcabodiimide are then added and the mixture stirred under nitrogen at 50°C for another 2 hours, another 3 mg of N-hydroxy-succinimide and another 3 mg of dicyclohexyl carbodiimide are added and the mixture is stirred for another 8 hours at 50°C under nitrogen. The whole mixture is then poured into 60 ml of peroxide-free ether, allowed to stand at 0°C for 18 hours, the fine precipitate is filtered off and dried under reduced pressure at 40°C. 30 mg of the crude, protected N$^\alpha$-lauroyl-dotriacontapeptideamide are obtained. For purification, the crude product is dissolved in methanol+λ chloroform (1:1) and chromatographed upwards through a column (1.5 × 30 cm), prepared in the same mixture, of Sephadex LH 20. Fractions of 3 ml each are collected, evaporated separately, and their purity investigated by thin-layer chromatography on silica gel plates ($Rf_{52A} = 0.55$). There are obtained 15 mg of purified, protected dotriacontapeptideamide.

EXAMPLE 12

H-C̅y̅s̅-Gly-Asn-Leu-Ser-Thr-C̅y̅s̅-Met-Ley-Gly-Thr-Tyr-Thr-Gln-Aso-Phe-Asn-Lys-Phe-His-Thr-Phe-Pro-Gln-Thr-Ala-Ile-Gly-Val-Gly-Ala-Pro-NH$_2$ (Calcitonine M)

32 mg of BOC-C̅y̅s̅-Gly-Asn-Leu-Ser(tBu)-Thr(tBu)-C̅y̅s̅-Met-Leu-Gly-Thr(tBu)-Tyr(tBu)-Thr-tBu)-Gln-Asp(OtBu)-Phe-Asn-Lys(BOC)-Phe-His-Thr(tBu)-Phe-Pro-Gln-Thr(tBu)-Ala-Ile-Gly-Val-Gly-Ala-Pro-NH$_2$ are freed from the protective groups in the manner described in Example 2. The resulting acetate of calcitonin M shows the same thin-layer chromatographic and electrophoretic behavior as the product described in Example 2. In thin-layer chromatography on alumina "Alox" (Camag) $Rf_{52} = 0.48$; $Rf_{45} = 0.41$; $Rf_{79} = 0.55$. In thin-layer chromatography on cellulose ("Selecta" plates S+S No.1440) $Rf_{101A} = 0.54$; $Rf_{45} = 0.40$. In electrophoresis on cellulose ("Selecta" plates No.1440) the travelling distance to the cathode at 280 V in 1.5 hours at pH $9.10 = 4.0$ cm, and at pH $4.85 = 4.2$ cm.

The protected dotriacontapeptide used as starting material can be prepared as follows:

1. BOC-Cys(TRI)-Gly-Asn-Leu-Ser(tBu)-Thr(tBu)-Cys(TRI)-Met-Leu-Gly-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-Val-Gly-Ala-Pro-NH$_2$ 125.6 mg of BOC-Cys(TRI)-Gly-Asn-Leu-Ser(tBu)-Thr(tBu)-Cys(TRI)-Met-Leu-Gly-OH and 189.0 mg of H-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-Val-Gly-Ala-Pro-NH$_2$ are slurried together with 31.4 mg of N-hydroxysuccinimide in 2.5 ml of N,N-dimethylformamide in an atmosphere of nitrogen. 37 mg of Dicyclohexylcarbodiimide in 1 ml of dimethylformamide are added and the batch is stirred for 4½ hours at 45°C. The batch is then stirred into 250 ml of absolute ether, the flaky precipitate is filtered off and washed with ether. 314 mg of a product are obtained which are sparingly soluble in methanol.

In the thin-layer chromatogram on silica gel $Rf_{100} = 0.51$; $Rf_{107} = 0.77$; $Rf_{52A} = 0.56$; $Rf_{43F} = 0.65$.

2.

BOC-Cys-Gly-Asn-Leu-Ser(tBu)-Thr(tBu)-Cys-Met-Leu-Gly-Thr(tBu)-Tyr(tBu)-Thr(tBu)-Gln-Asp(OtBu)-Phe-Asn-Lys(tBu)-phe-His-Thr(tBu)-phe-Pro-Gln-Thr(tBu)-Ala-Ile-Gly-Val-Gly-Ala-Pro-NH₂ isolated 219 mg of the protected dotriacontapeptide amide described under 1. above are dissolved in warm dimethylformamide and when the solution has cooled to room temperature, it is added dropwise in the course of 30 minutes to a solution of 124 mg of re-sublimed iodine in 30 ml of methanol. The vessel is flushed twice with 2.5 ml of dimethylformamide each time, and the batch stirred for another hour at room temperature, and then at 0°C 1.25 ml of N-aqueous sodium thiosulfate solution is slowly added dropwise until the solution is nearly colorless. After that, 0.05 ml of aqueous 2N-sodium hydroxide solution are added and the batch concentrated to about one-third its volume under reduced pressure. The solution is stirred into 450 ml of peroxide-free ether, and the precipitate is filtered off. The filter residue is subjected as it is to a counter-current distribution using the system methanol/buffer/chloroform/carbon tetrachloride 11:3:6:7 (buffer as in Example 1, under 18). After 280 stages, the substance is in the vessels 100 to 132. It is isolated and again distributed in the same system over 560 stages. The product localized by means of thin-layer chromatography is isolated (K = 0.69) and freed from ammonium acetate at 40°C under a high vacuum.

In the thin-layer chromatogram on silica gel $Rf_{52A}$ = 0.4; $Rf_{100}$ = 0.35; $Rf_{87}$ = 0.66; $Rf_{43E}$ = 0.59.

EXAMPLE 13

The protected calcitonin M used as starting material in Example 2 can be synthetized from the fragments 1–28+29–32 as follows:

1.

BOC-Cys-Gly-Asn-Leu-Ser(tBu)-Thr(tBu)-Cys-Met-Leu-Gly-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-OH 860 mg of BOC-Cys-Gly-Asn-Leu-Ser(tBu)-Thr(tBu)-Cys-Met-Leu-Gly-OH in 7 ml of dimethylformamide are mixed at 0°C with 0.1 ml of triethylamine and 292 mg of trichloracetic acid-pentachlorophenyl ester and the whole stirred at 0°C for one hour under an atmosphere of nitrogen. There are then added 1.627 g of H-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-OH (obtained from 1.75 g of the carbobenzoxy compound described in Example 1, under 49, by hydrogenation in 80% strength acetic acid), 0.09 ml of triethylamine and 7 ml of dimethylformamide, and the mixture is stirred overnight at room temperature. The mixture is added dropwise to ice-cold 0.02N-hydrochloric acid, and the crude product which precipitates is purified by counter-current distribution in the system methanol/buffer/chloroform/carbon tetrachloride (1:3:6:7, buffer as in Example 1, under 18). Distribution coefficient K = 0.8. The fractions containing the octacosapeptide derivative are combined, the solution concentrated to a great extent, and lyophilized from t-butanol. In the thin-layer chromatogram on silica gel $Rf_{45}$ = 0.33, $Rf_{100}$ = 0.35, and $Rf_{115}$ = 0.48.

2.

BOC-Cys-Gly-Asn-Leu-Ser(tBu)-Thr(tBu)-Cys-Met-Leu-Gly-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-Val-Gly-Ala-Pro-NH₂

40 mg of BOC-Cys-Gly-Asn-Leu-Ser(tBu)-Thr(tBu)-Cys-Met-Leu-Gly-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-OH and 27 mg of H-Val-Gly-Ala-Pro-NH₂ (Example 2, under 42) are dissolved in 1 ml of dimethylformamide. 2.9 mg of N-hydroxysuccinimide and 8.3 mg of dicyclohexylcarbodiimide are added to the solution which is then stirred for 2 hours under nitrogen. Another 1.7 mg of N-hydroxysuccinimide and 5.5 mg of dicyclohexyl-carbodiimide are added (each dissolved in 0.1 ml of dimethylformamide) and stirring is continued for another 3 hours at 45°C. The clear solution is then poured into 50 ml of ether, and the precipitate is filtered off with suction and dried, then triturated in a small amount of water, filtered with suction, and the still moist powder is reprecipitated from aqueous methanol. This causes the excess tetrapeptide derivative to separate from the crude product. The resulting protected Calcitonine M has the Rf values indicated under 45 In Example 2.

The protective groups are split off as described in Example 2. The resulting free calcitonine M contains traces of the sulfoxide derivative, but is pure otherwise. The biological activity of the product is 80 units/mg.

We claim:

1. A peptide of the formula

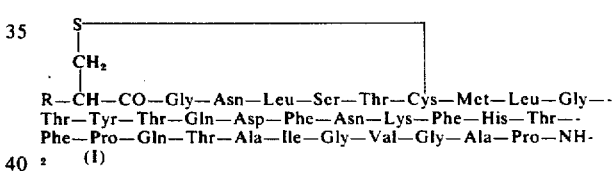

R-CH-CO-Gly-Asn-Leu-Ser-Thr-Cys-Met-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala-Pro-NH₂ 12 in which R is hydrogen or acylamino wherein acyl is a lower monobasic or dibasic alkanoyl, lower alkyloxycarbonyl, benzyloxycarbonyl, pyroglutamyl, carbamoyl, N-lower alkylcarbamoyl, N-phenylcarbamoyl, or N-phenylthiocarbamoyl, and, in addition, compounds of Formula I in which one or more of the asparagine and glutamine residues are exchanged for the aspartic acid or glutamic acid residue, respectively, or the aspartic acid residue is exchanged for the asparagine residue and, in addition, compounds of formula I in which R is amino and one or more of the asparagine and glutamine residues are exchanged for the aspartic acid or glutamic acid residue, respectively, or the aspartic acid residue is exchanged for the asparagine residue; as well as therapeutically acceptable acid addition salts and complexes with a member selected from the group consisting of zinc phosphate, zinc pyrophosphate, zinc hydroxide, gelatine, polyphloretin phosphate, and polyglutamic acid, with the proviso that all amino acid residues other than glycine and β-mercapto-propionic acid are of the L-configuration.

2. A peptide as claimed in claim 1 of the formula

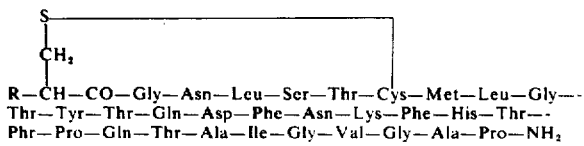

R—CH—CO—Gly—Asn—Leu—Ser—Thr—Cys—Met—Leu—Gly—-
Thr—Tyr—Thr—Gln—Asp—Phe—Asn—Lys—Phe—His—Thr—-
Phr—Pro—Gln—Thr—Ala—Ile—Gly—Val—Gly—Ala—Pro—NH₂ in which R is acylamino, wherein acyl is a lower monobasic or dibasic alkanoyl, lower alkyloxycarbonyl, benzyloxycarbonyl, pyroglutamyl, carbamoyl, N-lower alkylcarbamoyl, N-phenylcarbamoyl, or N-phenylthiocarbamoyl, or R, in addition, is amino in which one or more of the asparagine and glutamine residues are exchanged for the aspartic acid or glutamic acid residue, respectively, or the aspartic acid residue is exchanged for the asparagine residue; as well as therapeutically acceptable acid addition salts and complexes with a member selected from the group consisting of zinc phosphate, zinc pyrophosphate, zinc hydroxide, gelatine, polyphloretin phosphate, and polyglutamic acid, with the proviso that all amino acid residues other than glycine and β-mercaptopropionic acid are of the L-configuration.

3. A peptide as claimed in claim 2, in which R is acetylamino.

4. A peptide as claimed in claim 1 of the formula

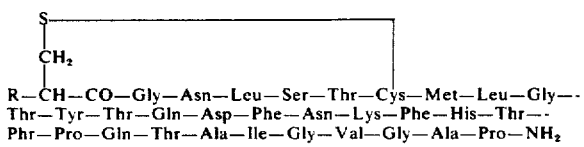

R—CH—CO—Gly—Asn—Leu—Ser—Thr—Cys—Met—Leu—Gly—-
Thr—Tyr—Thr—Gln—Asp—Phe—Asn—Lys—Phe—His—Thr—-
Phr—Pro—Gln—Thr—Ala—Ile—Gly—Val—Gly—Ala—Pro—NH₂ in which R is hydrogen, as well as therapeutically acceptable acid addition salts and complexes with a member selected from the group consisting of zinc phosphate, zinc pyrophosphate, zinc hydroxide, gelatine, polyphloretin phosphate, and polyglutamic acid, with the proviso that all amino acid residues other than glycine and β-mercaptopropionic acid are of the L-configuration.

5. Complexes of peptides as claimed in claim 1 with zinc phosphate, zinc pyrophosphate or zinc hydroxide.

6. Complexes of peptides as claimed in claim 1 with gelatine, polyphloretin phosphate or polyglutamic acid.

7. H-Thr-(tBu)-Tyr(tBu)-Thr(tBu)-Gln-Asp(OtBu)-Phe-Asn-Lys(BOC)-Phe-His-Thr(tBu)-Phe-Pro-Gln-Thr-(tBu)-Ala-Ile-Gly-Val-Gly-Ala-Pro-NH₂ in which all amino acid residues other than glycine are of the L-configuration.

8. A peptide of the formula

CH₂—CO—Gly—Asn—Leu—Ser—Thr—Cys—Met—Leu—Gly—-
Thr—Tyr—Thr—Gln—Asp—Phe—Asn—Lys—Phe—His—Thr—-
Phe—Pro—Gln—Thr—Ala—Ile—Gly—Val—Gly—Ala—Pro—NH₂ with the proviso that all amino acid residues other than glycine and β-mercapto-propionic acid are of the L-configuration.

9. A peptide of the formula Cys-Gly-Asn-Leu-Ser-Thr-Cys-Met-Leu-Gly-Thr-Tyr-Thr-Gln-Asn-Phe-Asn-Lys-Phe-His-Thr-Phe-Pro-Gln-Thr-Ala-Ile-Gly-Val-Gly-Ala-Pro-NH₂ with the proviso that all amino-acid residues other than glycine are of the L-configuration.

10. BOC-Cys-Gly-Asn-Leu-Ser(tBu)-Thr-(tBu)-Cys-Met-Leu-Gly-Thr(tBu)-Tyr(tBu)-Thr(tBu)-Gln-Asp(OtBu)-Phe-Asn-Lys(BOC)-Phe-His-Thr(tBu)-Phe-Pro-Gln-Thr(tBu)-Ala-Ile-Gly-Val-Gly-Ala-Pro-NH₂ in which all amino acid residues other than glycine are of the L-configuration.

11. BOC-Cys-Gly-Asn-Leu-Ser-Thr-Cys-Met-Leu-Gly-Thr-Tyr-Thr-Gln-Asp(OtBu)-Phe-Asn-Lys(BOC)-Phe-His-Thr-Phe-Pro-Gln-Thr-Ala-Ile-Gly-Val-Gly-Ala-Pro-NH₂ in which all amino acid residues other than glycine are of the L-configuration.

12. BOC-Cys-Gly-Asn-Leu-Ser(tBu)-Thr-(tBu)-Cys-Met-Leu-Gly-OH in which all amino acid residues other than glycine are of the L-configuration.

13. BOC-Cys-Gly-Asn-Leu-Ser-Thr-Cys-Met-Leu-Gly-OH in which all amino acid residues other than glycine are of the L-configuration.

14. H-Cys-Gly-Asn-Leu-Ser-Thr-Cys-Met-Leu-Gly-OH and its derivatives in which the amino group is protected by t-butyloxycarbonyl and the mercapto groups are protected by trityl in which all amino acid residues other than glycine are of the L-configuration.

15. BOC-Cys-(TRI)-Gly-Asn-Leu-Ser(tBu)-Thr(tBu)-Cys(TRI)-Met-Leu-Gly-OH in which all amino acid residues other than glycine are of the L-configuration.

16. H-Thr-Tyr-Thr-Gln-Asp(OtBu)-Phe-Asn-Lys(-BOC)-Phe-His-Thr-Phe-Pro-Gln-Thr-Ala-Ile-Gly-Val-Gly-Ala-Pro-NH₂ in which all amino acid residues other than glycine are of the L-configuration.

17. A pharmaceutical composition comprising a hypocalcaemically effective amount of a peptide of claim 1 and a pharmaceutical excipient.

18. A pharmaceutical composition of claim 17, wherein the peptide is a peptide of claim 8.

19. A pharmaceutical composition of claim 17, wherein the peptide is a peptide of claim 9.

* * * * *